United States Patent
Jiang et al.

(10) Patent No.: US 8,680,100 B2
(45) Date of Patent: Mar. 25, 2014

(54) SULFONYLHYDRAZIDE COMPOUNDS FOR TREATING PROLIFERATIVE DISORDERS

(75) Inventors: Jun Jiang, Norwood, MA (US); Teresa Kowalczyk-Przewloka, Tewksbury, MA (US); Stefan M. Schweizer, Memphis, TN (US); Zhi-Qiang Xia, Acton, MA (US); Shoujun Chen, Bedford, MA (US); Christopher Borella, Bedford, MA (US); Lijun Sun, Harvard, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

(21) Appl. No.: 13/132,106

(22) PCT Filed: Dec. 1, 2009

(86) PCT No.: PCT/US2009/066211
§ 371 (c)(1), (2), (4) Date: Nov. 28, 2011

(87) PCT Pub. No.: WO2010/065512
PCT Pub. Date: Jun. 10, 2010

(65) Prior Publication Data
US 2012/0065206 A1    Mar. 15, 2012

Related U.S. Application Data

(60) Provisional application No. 61/200,526, filed on Dec. 1, 2008.

(51) Int. Cl.
| | |
|---|---|
| A61K 31/5375 | (2006.01) |
| A61K 31/4965 | (2006.01) |
| A61K 31/445 | (2006.01) |
| A61K 31/4409 | (2006.01) |
| A61K 31/426 | (2006.01) |
| A61K 31/421 | (2006.01) |
| A61K 31/402 | (2006.01) |
| A61K 31/381 | (2006.01) |
| A61K 31/357 | (2006.01) |
| A61K 31/341 | (2006.01) |
| A61K 31/27 | (2006.01) |
| A61K 31/16 | (2006.01) |
| C07D 295/215 | (2006.01) |
| C07D 241/28 | (2006.01) |
| C07D 211/98 | (2006.01) |
| C07D 213/78 | (2006.01) |
| C07D 277/56 | (2006.01) |
| C07D 263/34 | (2006.01) |
| C07D 207/12 | (2006.01) |
| C07D 333/68 | (2006.01) |
| C07D 317/46 | (2006.01) |
| C07D 307/68 | (2006.01) |
| C07C 333/12 | (2006.01) |
| C07C 327/18 | (2006.01) |
| A61P 35/00 | (2006.01) |

(52) U.S. Cl.
USPC .................. 514/237.5; 514/255.06; 514/327; 514/354; 514/365; 514/374; 514/423; 514/443; 514/465; 514/471; 514/484; 514/599; 544/160; 544/406; 546/243; 546/313; 548/200; 548/236; 548/538; 549/57; 549/436; 549/487; 558/234; 558/238; 564/74

(58) Field of Classification Search
USPC ......... 514/237.5, 255.06, 327, 354, 365, 374, 514/423, 443, 465, 471, 484, 599; 544/160; 546/243, 313; 548/200, 236, 538; 549/57, 436, 487; 558/234, 238; 564/74
See application file for complete search history.

(56) References Cited

U.S. PATENT DOCUMENTS

| | | |
|---|---|---|
| 6,762,204 B2 | 7/2004 | Koya et al. |
| 6,800,660 B2 | 10/2004 | Koya et al. |
| 6,825,235 B2 | 11/2004 | Chen et al. |
| 6,924,312 B2 | 8/2005 | Koya et al. |
| 7,001,923 B2 | 2/2006 | Koya et al. |

(Continued)

FOREIGN PATENT DOCUMENTS

| | | |
|---|---|---|
| JP | 52-15549 A | 8/1993 |
| WO | WO 2008024303 A2 * | 2/2008 |

OTHER PUBLICATIONS

M. Mohan et al., Synthesis, Characterization and Antitumor Properties of Some Metal Complexes of 2,6-Diacetylpyridine Bis(N4-azacyclic Thiosemicarbazones), J. Inorganic Biochem. 34, 41-54 (1998).

(Continued)

*Primary Examiner* — Alicia L Otton
*Assistant Examiner* — Amanda L Aguirre
(74) *Attorney, Agent, or Firm* — McCarter & English, LLP; Steven G. Davis

(57) ABSTRACT

The present invention is directed to compounds represented by structural formula (I), or a pharmaceutically acceptable salt or a transition metal chelate, coordinate or complex thereof or a transition metal chelate, coordinate or complex of a deprotonated form of the compound. Pharmaceutical composition and method of use for these compounds are also included.

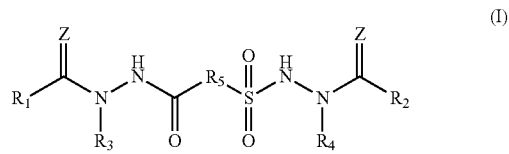

15 Claims, 24 Drawing Sheets

(56) References Cited

U.S. PATENT DOCUMENTS

| | | | |
|---|---|---|---|
| 7,037,940 B2 | 5/2006 | Koya et al. |
| 7,074,952 B2 | 7/2006 | Chen et al. |
| 7,345,094 B2 | 3/2008 | Koya et al. |
| 7,368,473 B2 | 5/2008 | Koya et al. |
| 7,385,084 B2 | 6/2008 | Koya et al. |
| 7,435,843 B2 | 10/2008 | Chen et al. |
| 7,579,503 B2 | 8/2009 | Koya et al. |
| 7,645,904 B2 | 1/2010 | Chen et al. |
| 7,652,168 B2 | 1/2010 | Chen et al. |
| 7,671,092 B2 | 3/2010 | Koya et al. |
| 7,678,832 B2 | 3/2010 | Lunsmann et al. |
| 7,709,683 B2 | 5/2010 | Chen et al. |
| 7,750,042 B2 | 7/2010 | Koya et al. |
| 7,763,658 B2 | 7/2010 | Koya et al. |
| 7,795,313 B2 | 9/2010 | Koya et al. |
| 2006/0142386 A1 | 6/2006 | Barsoum |
| 2006/0142393 A1 | 6/2006 | Sherman et al. |
| 2006/0167106 A1 | 7/2006 | Zhang et al. |
| 2007/0088057 A1 | 4/2007 | Lunsmann et al. |
| 2008/0118562 A1 | 5/2008 | Koya |
| 2008/0119440 A1 | 5/2008 | Koya |
| 2008/0176828 A1 | 7/2008 | Williams et al. |
| 2008/0226588 A1 | 9/2008 | McLeod |
| 2009/0023736 A1 | 1/2009 | Koya et al. |
| 2009/0042991 A1 | 2/2009 | Barsoum et al. |
| 2009/0093538 A1 | 4/2009 | Bertin et al. |
| 2009/0137682 A1 | 5/2009 | Dahl |
| 2010/0068174 A1 | 3/2010 | Jacobson |
| 2010/0081635 A1 | 4/2010 | Chen et al. |
| 2010/0093828 A1 | 4/2010 | Koya et al. |
| 2010/0249239 A1 | 9/2010 | Lunsmann et al. |
| 2010/0280075 A1 | 11/2010 | Koya et al. |
| 2010/0324143 A1 | 12/2010 | Koya et al. |
| 2011/0098476 A1 | 4/2011 | Chen et al. |
| 2011/0196025 A1 | 8/2011 | Kostik et al. |
| 2011/0245262 A1 | 10/2011 | Sun et al. |
| 2011/0245577 A1 | 10/2011 | Koya |
| 2011/0288162 A1 | 11/2011 | Masazumi et al. |
| 2011/0294814 A1 | 12/2011 | Kowalczyk-Prezewloka et al. |
| 2011/0294877 A1 | 12/2011 | Masazumi et al. |
| 2011/0294895 A1 | 12/2011 | Lunsmann et al. |
| 2012/0035266 A1 | 2/2012 | Koya et al. |
| 2012/0065206 A1 | 3/2012 | Jiang et al. |
| 2012/0065235 A1 | 3/2012 | Sun et al. |

OTHER PUBLICATIONS

G. F. de Sousa et al., "Structural and Spectral Studies of a Heterocyclic N(4)-Substituted Bis(thiosemicarbazone), H22,6Achexim.H20, Its Heptacoordinated Tin(IV) Complex [Bu2Sn(2,6Achexim)], and its Binuclear Zinc(II) Complex [Zn(2,6Achexim)]2", Polyhedron, 19, 841-847 (2000).

Yusupov, V.G. et al., "Copper(II) Complexes with Benzoyl-, thiobenzoylhydrazones and thiosemicarbazones of diacetyl and 1,1-diacetylcyclopropane", Koordinatsionnaya Khimiya 16(10), 1350-1354 (1990) (English abstract only).

\* cited by examiner

SULFONYLHYDRAZIDE COMPOUNDS FOR TREATING PROLIFERATIVE DISORDERS

RELATED APPLICATIONS

This application is a 35 U.S.C. §371 national stage filing of International Application No. PCT/US2009/066211 filed Dec. 1, 2009, which is related and claims priority to U.S. Ser. No. 61/200,526, filed Dec. 1, 2008. The entire contents of these applications are explicitly incorporated herein by reference.

BACKGROUND OF THE INVENTION

There is a need to develop new compounds that are effective in treating proliferative disorders, such as cancer and Hsp70 responsive disorders described herein.

SUMMARY OF THE INVENTION

One embodiment of the invention is a compound represented by Structural Formula (I):

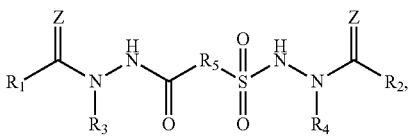

or a pharmaceutically acceptable salt or a transition metal chelate, coordinate or complex thereof or a transition metal chelate, coordinate or complex of a deprotonated form of the compound, wherein:

each Z is independently S, O or Se, provided that Z cannot both be O;

$R_1$ and $R_2$ are each independently selected from the group consisting of an optionally substituted alkyl, an optionally substituted alkenyl, an optionally substituted alkynyl; an optionally substituted cycloalkyl, an optionally substituted cycloalkenyl, an optionally substituted heterocyclic group wherein the heterocyclic group is bonded to the thiocarbonyl carbon via a carbon-carbon linkage, an optionally substituted phenyl, an optionally substituted bicyclic aryl, an optionally substituted five to seven-membered monocyclic heteroaryl, an optionally substituted nine to fourteen-membered bicyclic heteroaryl wherein the heteroaryl group is bonded to the thiocarbonyl carbon via a carbon-carbon linkage, $-NR_{12}R_{13}$, $-OR_{14}$, $-SR_{14}$ and $-S(O)_pR_{15}$;

$R_3$ and $R_4$ are each independently selected from the group consisting of an optionally substituted alkyl, an optionally substituted alkenyl, an optionally substituted alkynyl, an optionally substituted cycloalkyl, an optionally substituted cycloalkenyl, an optionally substituted heterocyclic group, and an optionally substituted five to six-membered aryl or heteroaryl group; or $R_1$ and $R_3$ and/or $R_2$ and $R_4$, taken together with the atoms to which they are attached, form an optionally substituted heterocyclic group or an optionally substituted heteroaryl group. Alternatively, in addition to the values for $R_3$ and $R_4$ recited in this paragraph and the immediately preceding paragraph, $R_3$ and $R_4$ can also be hydrogen;

$R_5$ is $-CR_6R_7-$, $-C(=CHR_8)-$ or $-C(=NR_8)-$;

$R_6$ and $R_7$ are both $-H$ or an optionally substituted lower alkyl;

$R_8$ is selected from the group consisting of $-OH$, an alkyl, an alkenyl, an alkynyl, an alkoxy, an alkenoxy, an alkynoxyl, a hydroxyalkyl, a hydroxyalkenyl, a hydroxyalkynyl, a haloalkyl, a haloalkenyl, a haloalkynyl, an optionally substituted phenyl, an optionally substituted bicyclic aryl, an optionally substituted five to six-membered monocyclic heteroaryl, an optionally substituted nine to fourteen-membered bicyclic heteroaryl, an optionally substituted cycloalkyl or an optionally substituted heterocyclic group; $-NR_{10}R_{11}$, and $-COR_9$;

$R_9$ is an optionally substituted phenyl, an optionally substituted bicyclic aryl, an optionally substituted five or six-membered monocyclic heteroaryl, an optionally substituted nine to fourteen-membered bicyclic heteroaryl, an optionally substituted alkyl, an optionally substituted cycloalkyl or an optionally substituted heterocyclic group;

$R_{10}$ and $R_{11}$ are each independently selected from the group consisting of $-H$, $-OH$, amino, (di)alkylamino, an alkyl, an alkenyl, an alkynyl, an alkoxy, an alkenoxy, an alkynoxyl, a hydroxyalkyl, a hydroxyalkenyl, a hydroxyalkynyl, a haloalkyl, a haloalkenyl, a haloalkynyl, an optionally substituted phenyl, an optionally substituted bicyclic aryl, an optionally substituted five to six-membered monocyclic heteroaryl, an optionally substituted nine to fourteen-membered bicyclic heteroaryl, an optionally substituted cycloalkyl or an optionally substituted heterocyclic group and $-COR_9$, or $R_{10}$ and $R_{11}$, taken together with the nitrogen atom to which they are attached, form a five to six-membered heteroaryl group; and $R_{12}$, $R_{13}$ and $R_{14}$ are each independently $-H$, an optionally substituted alkyl, an optionally substituted phenyl or an optionally substituted benzyl, or $R_{12}$ and $R_{13}$, taken together with the nitrogen atom to which they are attached, form an optionally substituted heterocyclic group or an optionally substituted heteroaryl group;

$R_{15}$ is an optionally substituted alkyl, an optionally substituted aryl or an optionally substituted heteroaryl, and p is 1 or 2;

provided that when both Z are S and $R_3$ and $R_4$ are both methyl, then $R_1$ and $R_2$ are not both unsubstituted phenyl.

Alternatively, for compounds of structural formula (I), $R_{10}$ and $R_{11}$ are not both $-H$.

Another embodiment is a pharmaceutical composition comprising a compound of the invention and a pharmaceutically acceptable carrier or diluent. The pharmaceutical compositions can be used in therapy, for example, as an antiproliferative agent (e.g., anti-cancer agent). In addition, the pharmaceutical compositions can be used in therapy to treat disorders responsive to Hsp70 induction. The pharmaceutical compositions can also be used in therapy to treat, reduce or inhibit angiogenesis in a subject in need thereof.

The present invention also provides for a method of treating a subject with cancer, treating a subject with an Hsp70-responsive disorder or treating, reducing or inhibiting angiogenesis in a subject in need thereof. The method comprises administering to the subject an effective amount of a compound of the invention or a pharmaceutical composition of the invention. In one embodiment, the compound of the invention is administered with paclitaxel (Taxol®) or a paclitaxel analog.

The use of a compound of the invention for the manufacture of a medicament for treating a subject with cancer, for treating a subject with an Hsp70-responsive disorder or for treating, reducing or inhibiting angiogenesis in a subject in need thereof is also provided in the present invention.

The present invention is also directed to the use of a compound of the invention for treating a subject with cancer, for treating a subject with an Hsp70-responsive disorder or for treating, reducing or inhibiting angiogenesis in a subject in need thereof.

DETAILED DESCRIPTION OF THE INVENTION

Figure 1:
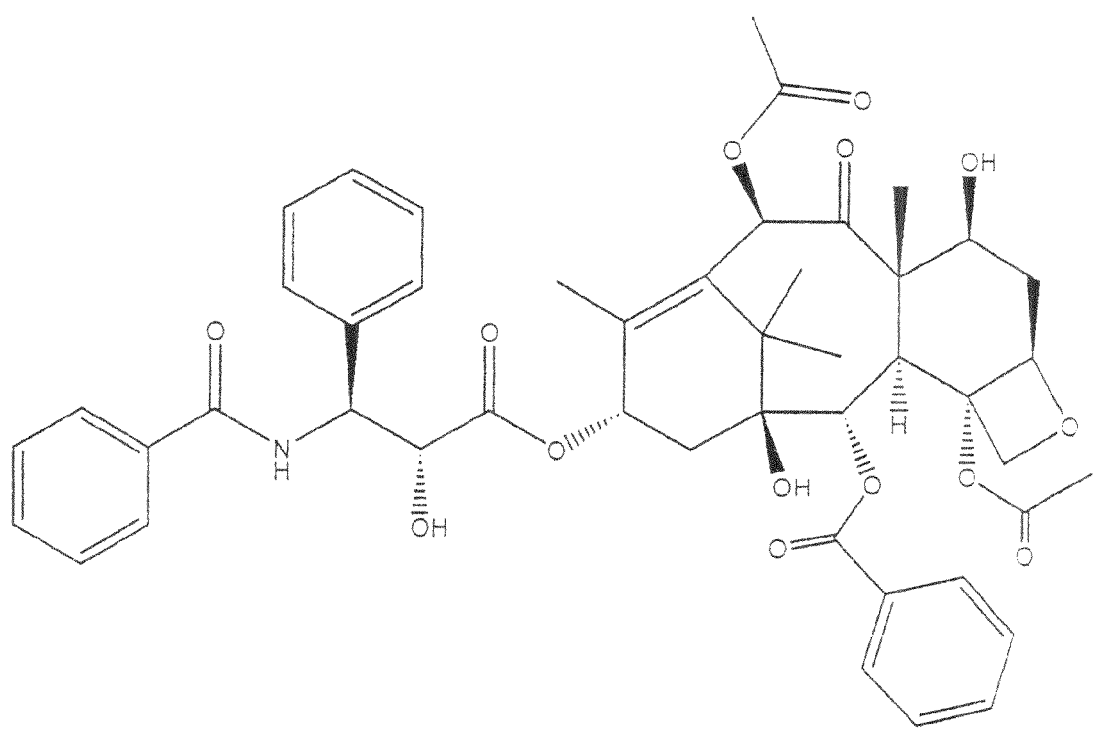
FIG. 1 is the structure of paclitaxel (Taxol®).

The present invention is directed to a compound represented by Structural Formula (I) or a pharmaceutically acceptable salt or a transition metal chelate, coordinate or complex thereof or a transition metal chelate, coordinate or complex of a deprotonated form of the compound. Values and particular values for the variables in Structural Formula (I) or a pharmaceutically acceptable salt or a transition metal chelate, coordinate or complex thereof or a transition metal chelate, coordinate or complex of a deprotonated form of the compound are provided in the following paragraphs. It is understood that the invention encompasses all combinations of the variables (i.e., $R_1$, $R_2$, $R_3$, etc.) defined herein. For Structural Formula (I):

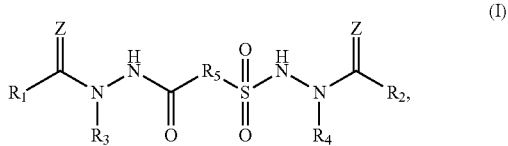

Each Z is independently S, O or Se, provided that Z cannot both be O. In one embodiment, both Z are Se. In another embodiment, one of Z is O or Se and the other Z is S.

$R_1$ and $R_2$ are each independently selected from the group consisting of an optionally substituted alkyl, an optionally substituted alkenyl, an optionally substituted alkynyl; an optionally substituted cycloalkyl, an optionally substituted cycloalkenyl, an optionally substituted heterocyclic group wherein the heterocyclic group is bonded to the thiocarbonyl carbon via a carbon-carbon linkage, an optionally substituted phenyl, an optionally substituted bicyclic aryl, an optionally substituted five to seven-membered monocyclic heteroaryl, an optionally substituted nine to fourteen-membered bicyclic heteroaryl wherein the heteroaryl group is bonded to the thiocarbonyl carbon via a carbon-carbon linkage, —$NR_{12}R_{13}$, —$OR_{14}$, —$SR_{14}$ and —$S(O)_pR_{15}$; or $R_1$ and $R_3$ and/or $R_2$ and $R_4$, taken together with the atoms to which they are attached, form an optionally substituted heterocyclic group or an optionally substituted heteroaryl group.

In one embodiment, $R_1$ and $R_2$ are each independently selected from the group consisting of an optionally substituted alkyl, an optionally substituted alkenyl, an optionally substituted alkynyl; an optionally substituted cycloalkyl, an optionally substituted cycloalkenyl, an optionally substituted heterocyclic group wherein the heterocyclic group is bonded to the thiocarbonyl carbon via a carbon-carbon linkage, an optionally substituted phenyl, an optionally substituted bicyclic aryl, an optionally substituted five to seven-membered monocyclic heteroaryl and an optionally substituted nine to fourteen-membered bicyclic heteroaryl.

In another embodiment, $R_1$ and $R_2$ are each independently selected from the group consisting of pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl, each of which is optionally substituted. In another embodiment, $R_1$ and $R_2$ are each independently optionally substituted phenyl or optionally substituted cyclopropyl.

In another embodiment, one of $R_1$ and $R_2$ is selected from the group consisting of —$NR_{12}R_{13}$, —$OR_{14}$, —$SR_{14}$ and —$S(O)_pR_{15}$.

In one embodiment, $R_1$ and $R_2$ are the same.

In another embodiment, $R_1$ and $R_3$ and/or $R_2$ and $R_4$, taken together with the atoms to which they are attached, form an optionally substituted heterocyclic group or an optionally substituted heteroaryl group.

$R_3$ and $R_4$ are each independently —H, an optionally substituted lower alkyl, an optionally substituted alkenyl, an optionally substituted alkynyl, an optionally substituted cycloalkyl, an optionally substituted phenyl or an optionally substituted benzyl. In one embodiment, $R_3$ and $R_4$ are each independently —H, methyl, ethyl, propyl, butyl, pentyl, hexyl, cyclopropyl, cyclobutyl, phenyl or benzyl, wherein the methyl, ethyl, propyl, butyl, pentyl, hexyl, cyclopropyl, cyclobutyl, phenyl and benzyl represented by $R_3$ and $R_4$ is optionally substituted with —OH, —Br, —Cl, —I, —F, —$R^a$, —$OR^a$, —$COOR^a$, —CN, —$NO_2$, morpholinyl, piperidinyl, and pyrrolidinyl, wherein $R^a$ is a lower alkyl or a lower haloalkyl. In another embodiment, $R_3$ and $R_4$ are both methyl, ethyl or phenyl, or one of $R_3$ and $R_4$ is methyl and the other one of $R_3$ and $R_4$ is ethyl.

$R_5$ is —$CR_6R_7$—, —C(=$CHR_8$)— or —C(=$NR_8$)—. In one embodiment, $R_5$ is —$CH_2$—. In another embodiment, $R_5$ is —C(=CH—$NR_{10}R_{11}$)—. In another embodiment, $R_5$ is —C(=CH—NHOH)—.

$R_{12}$, $R_{13}$ and $R_{14}$ are each independently —H, an optionally substituted alkyl, an optionally substituted phenyl or an optionally substituted benzyl, or $R_{12}$ and $R_{13}$, taken together with the nitrogen atom to which they are attached, form an optionally substituted heterocyclic group or an optionally substituted heteroaryl group. In one embodiment, $R_{12}$, $R_{13}$ and $R_{14}$ are each independently an optionally substituted lower alkyl, an optionally substituted phenyl or an optionally substituted benzyl, or $R_{12}$ and $R_{13}$, taken together with the nitrogen atom to which they are attached, form an optionally substituted five to six-membered heterocyclic group or an optionally substituted five to six-membered heteroaryl group, wherein the alkyl represented by $R_{12}$, $R_{13}$ and $R_{14}$ is optionally substituted with —OH, —Br, —Cl, —I, —F, —$R^a$, —$OR^a$ or —$COOR^a$, and the phenyl and benzyl represented by $R_{12}$, $R_{13}$ and $R_{14}$ and the heterocyclic and heteroaryl group represented by —$NR_{12}R_{13}$ are optionally substituted with —OH, —Br, —Cl, —I, —F, —$R^a$, —$OR^a$, —$COOR^a$, —CN, —$NO_2$, morpholinyl, piperidinyl, and pyrrolidinyl, wherein $R^a$ is a lower alkyl or a lower haloalkyl. In another embodiment, $R_{12}$, $R_{13}$ and $R_{14}$ are each independently —H, ($C_1$-$C_4$) alkyl, or phenyl optionally substituted with —OH, —Br, —Cl, —I, —F, —$R^a$, —$OR^a$, —$COOR^a$, —CN, —$NO_2$, morpholinyl, piperidinyl or pyrrolidinyl; or $R_{12}$ and $R_{13}$ taken together with the nitrogen to which they are attached form a heterocyclic group or a heteroaryl group selected from the group consisting of pyrrolidinyl, piperidinyl, morpholinyl, pyridinyl, pyrazinyl and imidazolyl, each of which is optionally substituted with —OH, —Br, —Cl, —I, —F, —$R^a$, —$OR^a$, —C(O)$OR^a$, —CN and —$NO_2$, wherein $R^a$ is a lower alkyl or a lower haloalkyl. In another embodiment, wherein $R_{12}$ and $R_{13}$ are each independently —H, methyl or ethyl; or $R_{12}$ and $R_{13}$, taken together with the nitrogen atom to which they are attached, form an unsubstituted pyrrolidinyl or piperidinyl; and $R_{14}$ is methyl, ethyl or unsubstituted phenyl.

In a first embodiment, the compound of the invention is represented by the following structural formula:

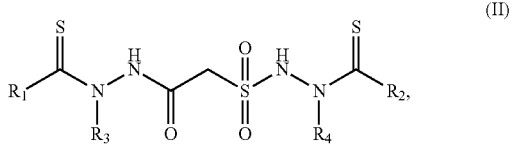
(II)

or a pharmaceutically acceptable salt or a transition metal chelate, coordinate or complex of the compound or a transition metal chelate, coordinate or complex of a deprotonated form of the compound. Values and specific values for the variables are as described above for structural formula (I).

In a second embodiment, for structural formula (II), $R_1$ and $R_2$ are each independently selected from the group consisting of an optionally substituted alkyl, an optionally substituted alkenyl, an optionally substituted alkynyl; an optionally substituted cycloalkyl, an optionally substituted cycloalkenyl, an optionally substituted heterocyclic group wherein the heterocyclic group is bonded to the thiocarbonyl carbon via a carbon-carbon linkage, an optionally substituted phenyl, an optionally substituted bicyclic aryl, an optionally substituted five to seven-membered monocyclic heteroaryl and an optionally substituted nine to fourteen-membered bicyclic heteroaryl.

In a more specific embodiment, $R_1$ and $R_2$ are each independently selected from the group consisting of pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl, each of which is optionally substituted. More specifically, the pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl represented by $R_1$ and $R_2$ are optionally substituted one or more substituents independently selected from the group consisting of —OH, —Br, —Cl, —I, —F, —$R^a$, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—$N(R^aR^b)$, —$NR^d$—C(=NH)—$NH_2$, —$NR^d$—C(=NH)—$NHR^a$, —$NR^d$—C(=NH)—$N(R^aR^b)$, —$NR^d$—C(=$NR^c$)—$NH_2$, —$NR^d$—C(=$NR^c$)—$NHR^a$, —$NR^d$—C(=$NR^c$)—$N(R^aR^b)$, —$NHNH_2$, —$NHNHR^a$, —$NHN(R^aR^b)$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —S(O)$R^a$, —S(O)$_2 R^a$, heterocyclic group, benzyl group and aryl group wherein $R^a$-$R^d$ are each independently a lower alkyl, a lower haloalkyl, a lower alkoxy, a lower hydroxyalkyl, benzyl, aryl, or, —$NR^aR^d$, taken together, can also form an optionally substituted heterocyclic group.

In another more specific embodiment, the pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl represented by $R_1$ and $R_2$ are optionally substituted one or more substituents independently selected from the group consisting of —OH, —Br, —Cl, —I, —F, —$R^a$, —$OR^a$, —$COOR^a$, —CN, —$NO_2$, morpholinyl, piperidinyl, and pyrrolidinyl, wherein $R^a$ is a lower alkyl or a lower haloalkyl. More specifically, the substituent is selected from the group consisting of —Br, —Cl, —I, —F, —$CF_3$, —C(O)$OC_2H_5$ and morpholinyl.

In a third embodiment, for structural formula (II), $R_3$ and $R_4$ are each independently —H, an optionally substituted lower alkyl, an optionally substituted alkenyl, an optionally substituted alkynyl, an optionally substituted cycloalkyl, an optionally substituted phenyl or an optionally substituted benzyl. In a more specific embodiment, $R_3$ and $R_4$ are each independently —H, methyl, ethyl, propyl, butyl, pentyl, hexyl, cyclopropyl, cyclobutyl, phenyl or benzyl, wherein the methyl, ethyl, propyl, butyl, pentyl, hexyl, cyclopropyl, cyclobutyl, phenyl and benzyl represented by $R_3$ and $R_4$ is optionally substituted with —OH, —Br, —Cl, —I, —F, —$R^a$, —$OR^a$, —$COOR^a$, —CN, —$NO_2$, morpholinyl, piperidinyl, and pyrrolidinyl, wherein $R^a$ is a lower alkyl or a lower haloalkyl. In a even more specific embodiment, $R_3$ and $R_4$ are both methyl, ethyl or phenyl, or one of $R_3$ and $R_4$ is methyl and the other one of $R_3$ and $R_4$ is —H, ethyl or propyl.

In a fourth embodiment, for structural formula (II), values and specific values for $R_1$ and $R_2$ are as defined in the second or the third embodiment, and values and specific values for $R_3$ and $R_4$ are as defined in the third embodiment. More specifically, $R_1$ and $R_2$ are the same. Alternatively, $R_1$ and $R_2$ are different.

In a fifth embodiment, the compound is represented by the following structural formulas:

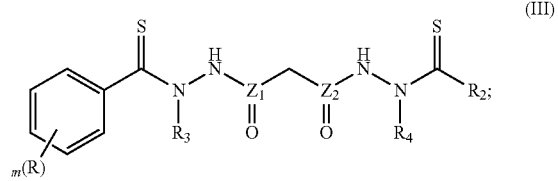
(III)

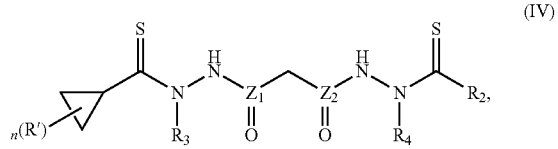
(IV)

or a pharmaceutically acceptable salt or a transition metal chelate, coordinate or complex of the compound or a transition metal chelate, coordinate or complex of a deprotonated form of the compound, wherein:

one of $Z_1$ and $Z_2$ is S=O, the other one of $Z_1$ and $Z_2$ is C;

R for each occurrence is independently selected from the group consisting of —H, —OH, —Br, —Cl, —I, —F, —$R^a$, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHN(R$^a$R$^b$), —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$—CHR$^a$, —CR$^c$=CR$^a$R$^b$, —CCR$^a$, —SH, —SR$^a$, —S(O)R$^a$, —S(O)$_2$R$^a$, heterocyclic group, benzyl group and aryl group;

R' is —H, —OH, —Br, —Cl, —I, —F, —R$^a$, —OR$^a$ or —O—COR$^a$;

R$^a$-R$^d$ are each independently a lower alkyl, a lower haloalkyl, a lower alkoxy, a lower hydroxyalkyl, benzyl, aryl, or, —NR$^a$R$^d$, taken together, can also form an optionally substituted heterocyclic group;

m is 1, 2, 3, 4, or 5;

n is 1, 2, 3, 4 or 5; and values and specific values for R$_2$ are as defined in the second embodiment and values and specific values for R$_3$ and R$_4$ are as defined in the third embodiment. More specifically, R is selected from the group consisting of —H, —OH, —Br, —Cl, —I, —F, —R$^a$, —OR$^a$, —COOR$^a$, —CN, —NO$_2$, morpholinyl, piperidinyl and pyrrolidinyl, wherein R$^a$ is a lower alkyl or a lower haloalkyl; and m is 1 or 2.

In a sixth embodiment, the compound is represented by the following structural formula:

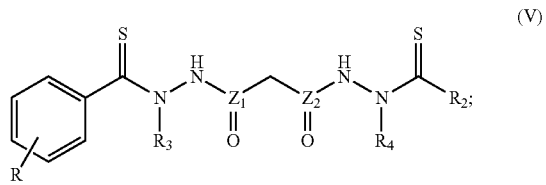

(V)

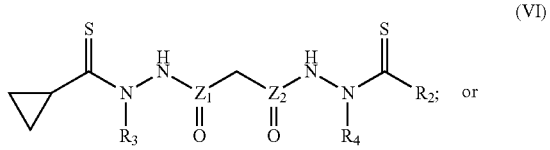

(VI)

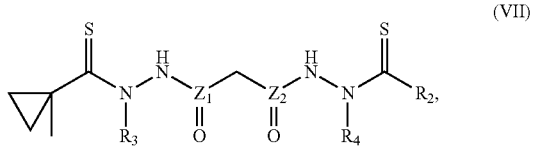

(VII)

or a pharmaceutically acceptable salt or a transition metal chelate, coordinate or complex of the compound or a transition metal chelate, coordinate or complex of a deprotonated form of the compound. Values and specific values for the variables are as defined in the fifth embodiment.

In a seventh embodiment, the compound is represented by the following structural formula:

(VIII)

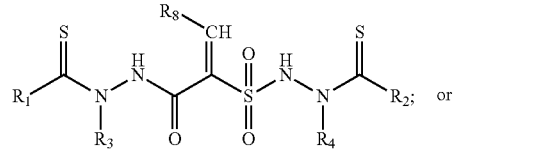

(IX)

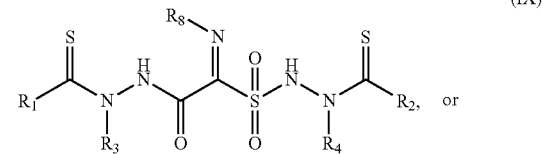

or a pharmaceutically acceptable salt or a transition metal chelate, coordinate or complex of the compound or a transition metal chelate, coordinate or complex of a deprotonated form of the compound, wherein R$_8$ is as described above for structural formula (I). Values and specific values for R$_1$ and R$_2$ are as defined in the second embodiment and values and specific values for R$_3$ and R$_4$ are as defined in the third embodiment.

In a more specific embodiment, R$_1$-R$_4$ are as defined in the previous paragraph; R$_8$ is —OH, —NR$_{10}$R$_{11}$, a lower alkoxy, a lower alkyl, wherein the lower alkyl and the lower alkoxy is optionally substituted with halogen or —OH; R$_{10}$ and R$_{11}$ are each independently —H, —OH or a lower alkyl or a (C$_3$-C$_6$) cycloalkyl. Even more specifically, R$_8$ is —NR$_{10}$R$_{11}$, wherein R$_{10}$ and R$_{11}$ are each independent selected from the group —H, —OH, methyl, ethyl, propyl and cyclopropyl.

In a eighth embodiment, R$_1$ are R$_2$ are the same and values and specific values for the variables are as described in the seventh embodiment, In a ninth embodiment, the compound is represented by the following structural formula:

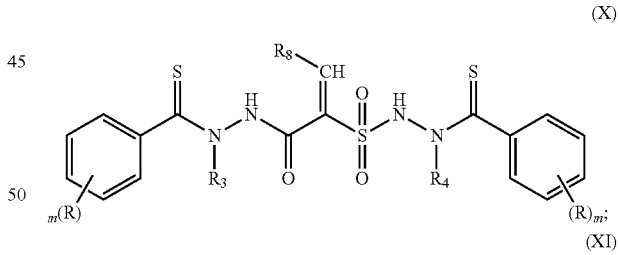

(X)

(XI)

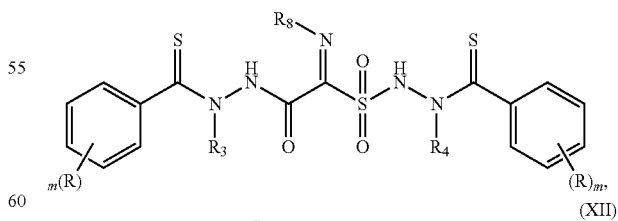

(XII)

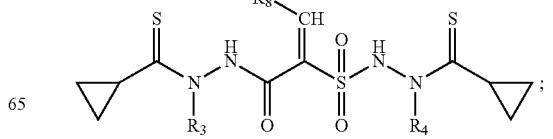

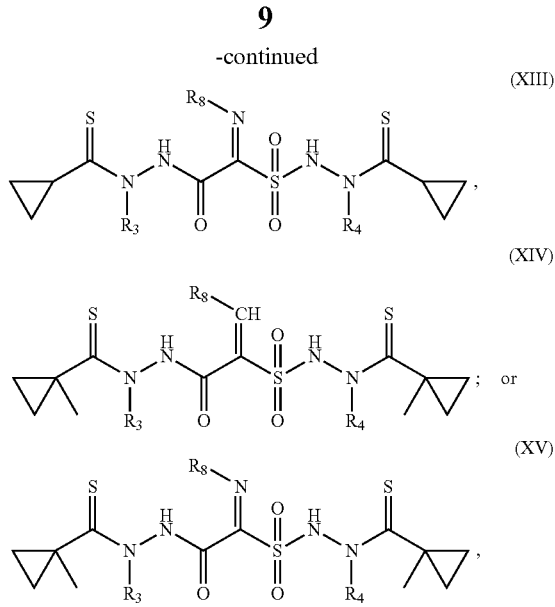

or a pharmaceutically acceptable salt or a transition metal chelate, coordinate or complex of the compound or a transition metal chelate, coordinate or complex of a deprotonated form of the compound. Values and specific values are as described in the seventh embodiment. In a more specific embodiment, R in structural formulas (X) and (XI) are R is OH, —Br, —Cl, —I, —F, —$R^a$, —$OR^a$, —$COOR^a$, —CN, —$NO_2$, morpholinyl, piperidinyl, or pyrrolidinyl; wherein $R^a$ is a lower alkyl or a lower haloalkyl; and m is 1 or 2.

In a tenth embodiment, for structural formula (II), one of $R_1$ and $R_2$ is —$NR_{12}R_{13}$, —$OR_{14}$, —$SR_{14}$ and —$S(O)_pR_{15}$; and the other one of $R_1$ and $R_2$ is selected from the group consisting of an optionally substituted alkyl, an optionally substituted alkenyl, an optionally substituted alkynyl; an optionally substituted cycloalkyl, an optionally substituted cycloalkenyl, an optionally substituted heterocyclic group wherein the heterocyclic group is bonded to the thiocarbonyl carbon via a carbon-carbon linkage, an optionally substituted phenyl, an optionally substituted bicyclic aryl, an optionally substituted five to seven-membered monocyclic heteroaryl, an optionally substituted nine to fourteen-membered bicyclic heteroaryl wherein the heteroaryl group is bonded to the thiocarbonyl carbon via a carbon-carbon linkage, —$NR_{12}R_{13}$, —$OR_{14}$, —$SR_{14}$ and —$S(O)_pR_{15}$. Values and specific values for $R_3$ and $R_4$ are as described in the third embodiment.

In a tenth embodiment, the compound is represented by the following structural formula:

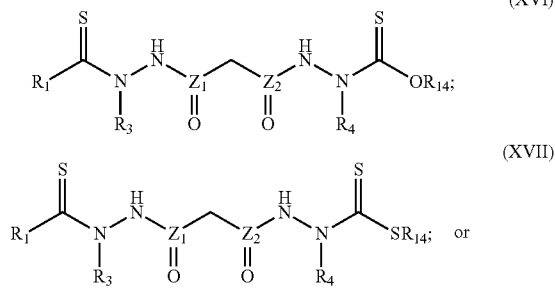

or a pharmaceutically acceptable salt or a transition metal chelate, coordinate or complex of the compound or a transition metal chelate, coordinate or complex of a deprotonated form of the compound, wherein:
one of $Z_1$ and $Z_2$ is S=O, and the other one of $Z_1$ and $Z_2$ is C; and
$R_1$ is selected from the group consisting of an optionally substituted alkyl, an optionally substituted alkenyl, an optionally substituted alkynyl; an optionally substituted cycloalkyl, an optionally substituted cycloalkenyl, an optionally substituted heterocyclic group wherein the heterocyclic group is bonded to the thiocarbonyl carbon via a carbon-carbon linkage, an optionally substituted phenyl, an optionally substituted bicyclic aryl, an optionally substituted five to seven-membered monocyclic heteroaryl, an optionally substituted nine to fourteen-membered bicyclic heteroaryl wherein the heteroaryl group is bonded to the thiocarbonyl carbon via a carbon-carbon linkage, —$NR_{12}R_{13}$, —$OR_{14}$, —$SR_{14}$ and —$S(O)_pR_{15}$. Values and specific values for the remainder of the variables are as described above for structural formula (I).

$R_1$ is selected from the group consisting of pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl, each of which is optionally substituted. More specifically, the pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl represented by $R_1$ and $R_2$ are optionally substituted one or more substituents independently selected from the group consisting of —OH, —Br, —Cl, —I, —F, —$R^a$, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—$N(R^aR^b)$, —$NR^d$—C(=NH)—$NH_2$, —$NR^d$—C(=NH)—$NHR^a$, —$NR^d$—C(=NH)—$N(R^aR^b)$, —$NR^d$—C(=$NR^c$)—$NH_2$, —$NR^d$—C(=$NR^c$)—$NHR^a$, —$NR^d$—C(=$NR^c$)—$N(R^aR^b)$, —$NHNH_2$, —$NHNHR^a$, —$NHN(R^aR^b)$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —$S(O)R^a$, —$S(O)_2 R^a$, heterocyclic group, benzyl group and aryl group wherein $R^a$-$R^d$ are each independently a lower alkyl, a lower haloalkyl, a lower alkoxy, a lower hydroxyalkyl, benzyl, aryl, or, —$NR^aR^d$, taken together, can also form an optionally substituted heterocyclic group.

In another more specific embodiment, the pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl represented by $R_1$ are optionally substituted one or more substituents independently selected from the group consisting of —OH, —Br, —Cl, —I, —F, —$R^a$, —$OR^a$, —$COOR^a$, —CN, —$NO_2$, morpholinyl, piperidinyl, and pyrrolidinyl, wherein $R^a$ is a lower alkyl or a lower haloalkyl. More specifically, the substituent is selected from the group consisting of —Br, —Cl, —I, —F, —$CF_3$, —C(O)$OC_2H_5$ and morpholinyl.

In a eleventh embodiment, for structural formulas (XVI), (XVII) and (XVIII), values and specific values $R_3$ and $R_4$ are as described above in the third embodiment, values and specific values for $R_1$ and $R_2$ are as described in the ten embodiment; and values and specific values for the remainder of the variables are as describe for structural formula (I).

In a twelfth embodiment, for structural formulas (XVI), (XVII) and (XVIII), $R_{12}$, $R_{13}$ and $R_{14}$ are each independently —H, an optionally substituted lower alkyl, an optionally substituted phenyl or an optionally substituted benzyl, or $R_{12}$ and $R_{13}$, taken together with the nitrogen atom to which they are attached, form an optionally substituted five to six-membered heterocyclic group or an optionally substituted five to six-membered heteroaryl group, wherein the alkyl represented by $R_{12}$, $R_{13}$ and $R_{14}$ is optionally substituted with —OH, —Br, —Cl, —I, —F, —$R^a$, —$OR^a$ or —$COOR^a$, and the phenyl and benzyl represented by $R_{12}$, $R_{13}$ and $R_{14}$ and the heterocyclic and heteroaryl group represented by —$NR_{12}R_{13}$ are optionally substituted with —OH, —Br, —Cl, —I, —F, —$R^a$, —$OR^a$, —$COOR^a$, —CN, —$NO_2$, morpholinyl, piperidinyl, and pyrrolidinyl, wherein $R^a$ is a lower alkyl or a lower haloalkyl. Values and specific values for the remainder of the variables are as described in the eleventh embodiment. More specifically, $R_{12}$, $R_{13}$ and $R_{14}$ are each independently —H, ($C_1$-$C_4$)alkyl, or phenyl optionally substituted with —OH, —Br, —Cl, —I, —F, —$R^a$, —$OR^a$, —$COOR^a$, —CN, —$NO_2$, morpholinyl, piperidinyl or pyrrolidinyl; or $R_{12}$ and $R_{13}$ taken together with the nitrogen to which they are attached form a heterocyclic group or a heteroaryl group selected from the group consisting of pyrrolidinyl, piperidinyl, morpholinyl, pyridinyl, pyrazinyl and imidazolyl, each of which is optionally substituted with —OH, —Br, —Cl, —I, —F, —$R^a$, —$OR^a$, —C(O)$OR^a$, —CN and —$NO_2$, wherein $R^a$ is a lower alkyl or a lower haloalkyl.

In a thirteen embodiment, the compound is represented by the following structural formula:

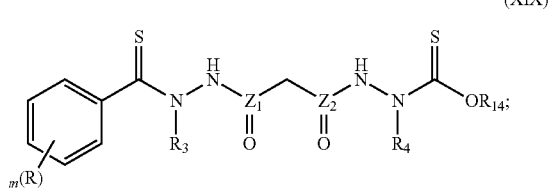

(XIX)

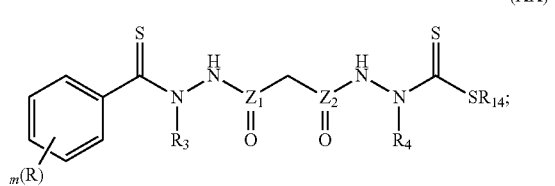

(XX)

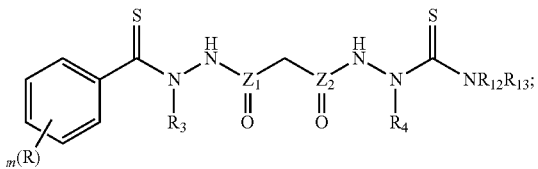

(XXI)

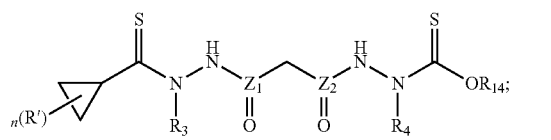

(XXII)

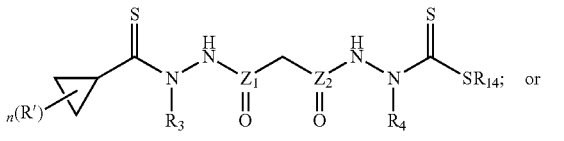

(XXIII)

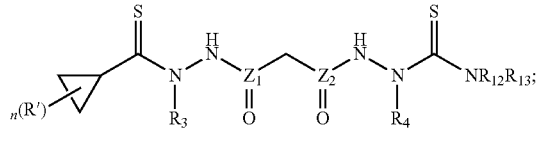

(XXIV)

or a pharmaceutically acceptable salt or a transition metal chelate, coordinate or complex of the compound or a transition metal chelate, coordinate or complex of a deprotonated form of the compound, wherein:

R for each occurrence is independently selected from the group consisting of —H, —OH, —Br, —Cl, —I, —F, —$R^a$, —$OR^a$, —O—$COR^a$, —$COR^a$, —CN, —$NO_2$, —COOH, —$SO_3H$, —$NH_2$, —$NHR^a$, —N($R^aR^b$), —$COOR^a$, —CHO, —$CONH_2$, —$CONHR^a$, —CON($R^aR^b$), —$NHCOR^a$, —$NRCOR^a$, —$NHCONH_2$, —$NHCONR^aH$, —NHCON($R^aR^b$), —$NR^cCONH_2$, —$NR^cCONR^aH$, —$NR^cCON$($R^aR^b$), —C(=NH)—$NH_2$, —C(=NH)—$NHR^a$, —C(=NH)—N($R^aR^b$), —C(=$NR^c$)—$NH_2$, —C(=$NR^c$)—$NHR^a$, —C(=$NR^c$)—N($R^aR^b$), —NH—C(=NH)—$NH_2$, —NH—C(=NH)—$NHR^a$, —NH—C(=NH)—N($R^aR^b$), —NH—C(=$NR^c$)—$NH_2$, —NH—C(=$NR^c$)—$NHR^a$, —NH—C(=$NR^c$)—N($R^aR^b$), —$NR^d$—C(=NH)—$NH_2$, —$NR^d$—C(=NH)—$NHR^a$, —$NR^d$—C(=NH)—N($R^aR^b$), —$NR^d$—C(=$NR^c$)—$NH_2$, —$NR^d$—C(=$NR^c$)—$NHR^a$, —$NR^d$—C(=$NR^c$)—N($R^aR^b$), —$NHNH_2$, —$NHNHR^a$, —NHN($R^aR^b$), —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —S(O)$R^a$, —S(O)$_2$ $R^a$, heterocyclic group, benzyl group and aryl group;

R' is —H, —OH, —Br, —Cl, —I, —F, —$R^a$, —$OR^a$ or —O—$COR^a$;

$R^a$-$R^d$ are each independently a lower alkyl, a lower haloalkyl, a lower alkoxy, a lower hydroxyalkyl, benzyl, aryl, or, —$NR^aR^d$, taken together, can also form an optionally substituted heterocyclic group;

m is 1, 2, 3, 4, or 5; and n is 1, 2, 3, 4 or 5.

Values and specific values for the remainder of the variables are as described above in the twelfth embodiment.

In a fourteenth embodiment, the compound is represented by the following structure formula:

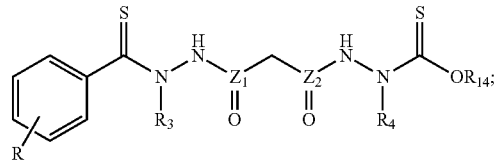
(XXV)

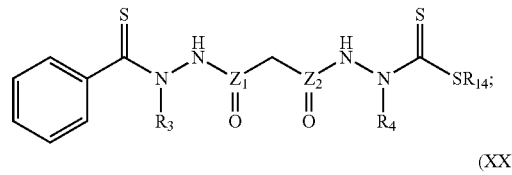
(XXVI)

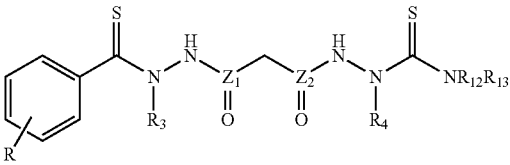
(XXVII)

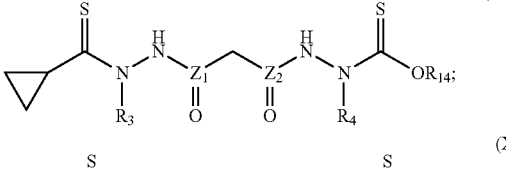
(XXVIII)

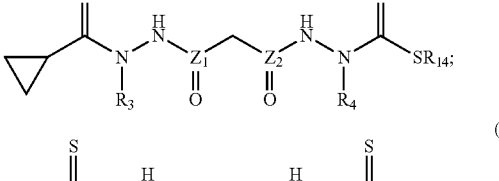
(XXIX)

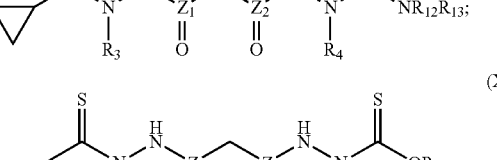
(XXX)

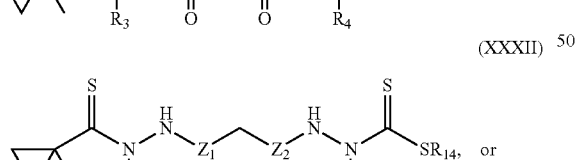
(XXXI)

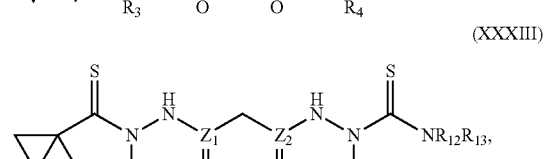
(XXXII) or

(XXXIII)

or a pharmaceutically acceptable salt or a transition metal chelate, coordinate or complex of the compound or a transition metal chelate, coordinate or complex of a deprotonated form of the compound. Values and specific values for the variables are as described in the thirteenth embodiment.

In a fifteenth embodiment, the compound is represented by the following structural formula:

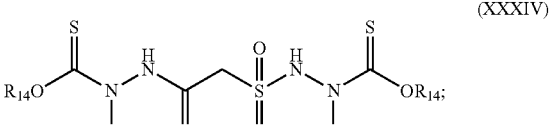
(XXXIV)

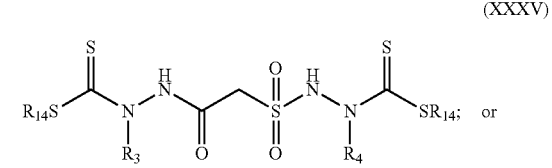
(XXXV) or

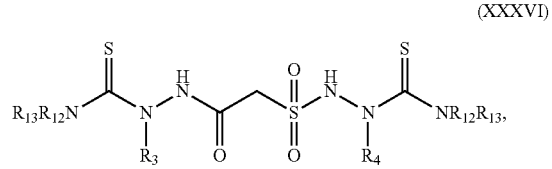
(XXXVI)

or a pharmaceutically acceptable salt or a transition metal chelate, coordinate or complex of the compound or a transition metal chelate, coordinate or complex of a deprotonated form of the compound. Values and specific values for $R_{12}$, $R_{13}$ and $R_{14}$ are as described in the twelfth embodiment and values and specific values for $R_3$ and $R_4$ are as described in the third specific embodiment.

In a sixteenth embodiment, the compound is represented by the following structural formula:

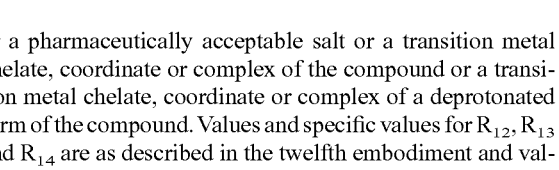
(XXXVII)

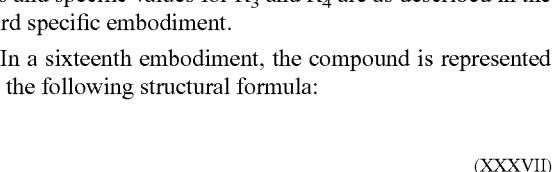
(XXXVIII)

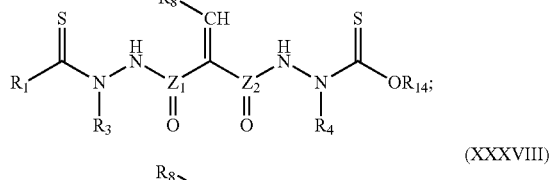
(XXXIX)

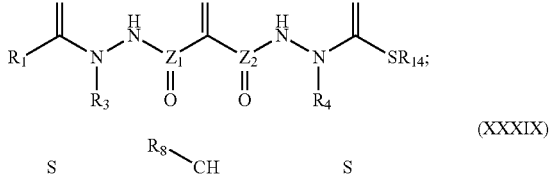
(XL)

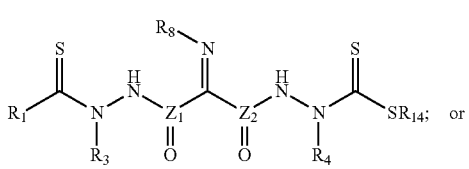

(XLI)

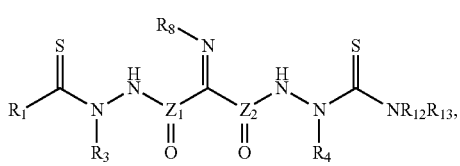

(XLII)

or a pharmaceutically acceptable salt or a transition metal chelate, coordinate or complex of the compound or a transition metal chelate, coordinate or complex of a deprotonated form of the compound, wherein:

one of $Z_1$ and $Z_2$ is S=O, and the other one of $Z_1$ and $Z_2$ is C; and $R_1$ is selected from the group consisting of an optionally substituted alkyl, an optionally substituted alkenyl, an optionally substituted alkynyl; an optionally substituted cycloalkyl, an optionally substituted cycloalkenyl, an optionally substituted heterocyclic group wherein the heterocyclic group is bonded to the thiocarbonyl carbon via a carbon-carbon linkage, an optionally substituted phenyl, an optionally substituted bicyclic aryl, an optionally substituted five to seven-membered monocyclic heteroaryl, an optionally substituted nine to fourteen-membered bicyclic heteroaryl wherein the heteroaryl group is bonded to the thiocarbonyl carbon via a carbon-carbon linkage, $-NR_{12}R_{13}$, $-OR_{14}$, $-SR_{14}$ and $-S(O)_pR_{15}$. Values and specific values for the remainder of the variables are as described above for structural formula (I).

In a more specific embodiment, $R_1$ is selected from the group consisting of phenyl, pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl, wherein each of the phenyl, pyrrolidinyl, pyrazinyl, pyridinyl, dioxolopyridinyl, benzothiophenyl, benzodioxolyl, thiophenyl, furanyl, morpholinyl, piperidinyl, cyclopropyl, cyclobutyl, cyclopentyl, cyclohexyl and (methyl)cyclopropyl represented by $R_1$ is optionally substituted.

In another more specific embodiment, each of the phenyl, pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl represented by $R_1$ is optionally substituted with one or more substituents independently selected from the group consisting of —OH, —Br, —Cl, —I, —F, $-R^a$, $-OR^a$, $-O-COR^a$, $-COR^a$, —CN, $-NO_2$, —COOH, $-SO_3H$, $-NH_2$, $-NHR^a$, $-N(R^aR^b)$, $-COOR^a$, —CHO, $-CONH_2$, $-CONHR^a$, $-CON(R^aR^b)$, $-NHCOR^a$, $-NRCOR^a$, $-NHCONH_2$, $-NHCONR^aH$, $-NHCON(R^aR^b)$, $-NR^cCONH_2$, $-NR^cCONR^aH$, $-NR^cCON(R^aR^b)$, $-C(=NH)-NH_2$, $-C(=NH)-NHR^a$, $-C(=NH)-N(R^aR^b)$, $-C(=NR^c)-NH_2$, $-C(=NR^c)-NHR^a$, $-C(=NR^c)-N(R^aR^b)$, $-NH-C(=NH)-NH_2$, $-NH-C(=NH)-NHR^a$, $-NH-C(=NH)-N(R^aR^b)$, $-NH-C(=NR^c)-NH_2$, $-NH-C(=NR^c)-NHR^a$, $-NH-C(=NR^c)-N(R^aR^b)$, $-NR^d-C(=NH)-NH_2$, $-NR^d-C(=NH)-NHR^a$, $-NR^d-C$ $(=NR^c)-N(R^aR^b)$, $-NHNH_2$, $-NHNHR^a$, $-NHN(R^aR^b)$, $-SO_2NH_2$, $-SO_2NHR^a$, $-SO_2NR^aR^b$, $-CH=CHR^a$, $-CH=CR^aR^b$, $-CR^c=CR^aR^b$, $-CR^c=CHR^a$, $-CR^c=CR^aR^b$, $-CCR^a$, —SH, $-SR^a$, $-S(O)R^a$, $-S(O)_2R^a$, heterocyclic group, benzyl group and aryl group wherein $R^a$-$R^d$ are each independently a lower alkyl, a lower haloalkyl, a lower alkoxy, a lower hydroxyalkyl, benzyl, aryl, or, $-NR^aR^d$, taken together, can also form an optionally substituted heterocyclic group.

In another specific embodiment, each of the phenyl, pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl represented by $R_1$ is optionally substituted with one or more substituents independently selected from the group consisting of —OH, —Br, —Cl, —I, —F, $-R^a$, $-OR^a$, $-COOR^a$, —CN, $-NO_2$, morpholinyl, piperidinyl, and pyrrolidinyl, wherein $R^a$ is a lower alkyl or a lower haloalkyl.

In a seventeenth embodiment, for structural formulas (XXXVII)-(XLII), values and specific values for $R_{12}$, $R_{13}$ and $R_{14}$ are as described in the twelfth embodiment and values and specific values for $R_3$ and $R_4$ are as described in the third embodiment. Values and specific values for the remainder of the variables are as described above in the sixteenth embodiment. More specifically, $R_8$ is selected from the group consisting of —OH, $-NR_{10}R_{11}$, a lower alkoxy, a lower alkyl, wherein the lower alkyl and the lower alkoxy is optionally substituted with halogen or —OH; $R_{10}$ and $R_{11}$ are each independently —H, —OH or a lower alkyl or a $(C_3-C_6)$ cycloalkyl. Even more specifically, $R_8$ is $-NR_{10}R_{11}$, wherein $R_{10}$ and $R_{11}$ are each independent selected from the group —H, —OH, methyl, ethyl, propyl and cyclopropyl.

In a eighteenth embodiment, the compound is represented by the following structural formula:

 (XLIII)

(XLIV)

or a pharmaceutically acceptable salt or a transition metal chelate, coordinate or complex of the compound or a transition metal chelate, coordinate or complex of a deprotonated form of the compound, wherein:

one of $Z_1$ and $Z_2$ is S=O; the other one of $Z_1$ and $Z_2$ is C; $X_1$, $X_2$, $X_3$ and $X_4$ are each independently selected from the group consisting of $=CR_{16}-$, $-CR_{17}R_{18}-$, $=N-$, $-NR_{19}-$, —O— and —S—; or $X_3$ and $X_4$, or $X_2$ and $X_3$, or $X_1$ and $X_2$, taken together form a fused aromatic ring optionally containing one or two heteroatoms and the fused aromatic ring is optionally substituted $X_5$, $X_6$ and $X_7$ are each independently selected from the group consisting of $=CR_{16}-$, $-CR_{17}R_{18}-$, $=N-$, $-NR_{19}-$, —O— and —S—; or $X_6$ and $X_7$, or $X_5$ and $X_6$, taken together to form a fused aromatic ring optionally containing one or two heteroatoms and the fused aromatic ring is optionally substituted;

$R_1$ is selected from the group consisting of an optionally substituted alkyl, an optionally substituted alkenyl, an optionally substituted alkynyl; an optionally substituted cycloalkyl, an optionally substituted cycloalkenyl, an optionally substituted heterocyclic group wherein the heterocyclic group is bonded to the thiocarbonyl carbon via a carbon-carbon linkage, an optionally substituted phenyl, an optionally substituted bicyclic aryl, an optionally substituted five to seven-membered monocyclic heteroaryl, an optionally substituted nine to fourteen-membered bicyclic heteroaryl wherein the heteroaryl group is bonded to the thiocarbonyl carbon via a carbon-carbon linkage, $-NR_{12}R_{13}$, $-OR_{14}$, $-SR_{14}$ and $-S(O)_pR_{15}$, or $R_1$ and $R_3$, taken together with the atoms to which they are attached, form an optionally substituted heterocyclic group or an optionally substituted heteroaryl group; and $R_{16}$, $R_{17}$, $R_{18}$ and $R_{19}$ are each independently selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclic group, an optionally substituted aryl, an optionally substituted heteroaryl, —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHN(R$^a$R$^b$), —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, wherein R$^a$-R$^d$ are each independently a lower alkyl, a lower haloalkyl, benzyl, aryl, or, —NR$^a$R$^d$, taken together, can also form an optionally substituted heterocyclic group.

In a nineteen embodiment, the compound is represented by the following structural formula:

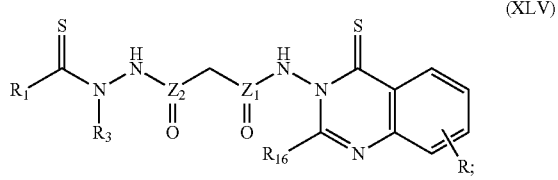

(XLV)

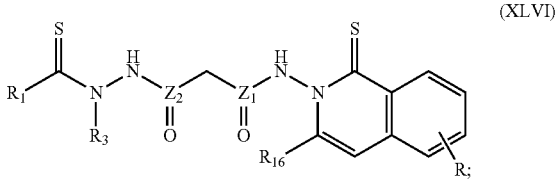

(XLVI)

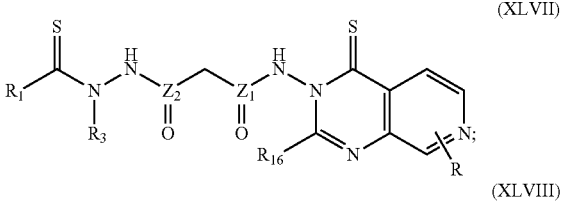

(XLVII)

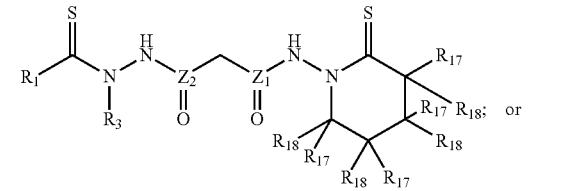

(XLVIII)

(XLIX)

or a pharmaceutically acceptable salt or a transition metal chelate, coordinate or complex of the compound or a transition metal chelate, coordinate or complex of a deprotonated form of the compound, wherein:

R for each occurrence is independently selected from the group consisting of —H, —OH, —Br, —Cl, —I, —F, —R$^a$, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHN(R$^a$R$^b$), —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, heterocyclic group, benzyl group and aryl group. Values and specific values for the remainder of the variables are as described in the eighteen embodiment. More specifically, $R_{16}$, $R_{17}$ and $R_{18}$ are each independently selected from the group consisting of —H, —R$^a$, —OH, —Br, —Cl, —I, —F and —OR$^a$ and R is selected from the group consisting of —H, —R$^a$, —OH, —Br, —Cl, —I, —F, —R$^a$, —OR$^a$.

In a twentieth embodiment, for structural formulas (XLV)-(XLIX), $R_1$ is selected from the group consisting of phenyl, pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl, —OR$_{14}$, —SR$_{14}$, —NR$_{12}$R$_{13}$ and —S(O)$_p$R$_{15}$, wherein each of the phenyl, pyrrolidinyl, pyrazinyl, pyridinyl, dioxolopyridinyl, benzothiophenyl, benzodioxolyl, thiophenyl, furanyl, morpholinyl, piperidinyl, cyclopropyl, cyclobutyl, cyclopentyl, cyclohexyl and (methyl)cyclopropyl represented by $R_1$ is optionally substituted. More specifically, each of the phenyl, pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl represented by $R_1$ is optionally substituted with one or more substituents independently selected from the group consisting of —OH, —Br, —Cl, —I, —F, —$R^a$, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—$N(R^aR^b)$, —$NR^d$—C(=NH)—$NH_2$, —$NR^d$—C(=NH)—$NHR^a$, —$NR^d$—C(=NH)—$N(R^aR^b)$, —$NR^d$—C(=$NR^c$)—$NH_2$, —$NR^d$—C(=$NR^c$)—$NHR^a$, —$NR^d$—C(=$NR^c$)—$N(R^aR^b)$, —$NHNH_2$, —$NHNHR^a$, —$NHN(R^aR^b)$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$—$CHR^a$, —$CR^c$=$CR^aR^b$, —$CCR^a$, —SH, —$SR^a$, —$S(O)R^a$, —$S(O)_2 R^a$, heterocyclic group, benzyl group and aryl group wherein $R^a$-$R^d$ are each independently a lower alkyl, a lower haloalkyl, a lower alkoxy, a lower hydroxyalkyl, benzyl, aryl, or, —$NR^aR^d$, taken together, can also form an optionally substituted heterocyclic group. Even more specifically, each of the phenyl, pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl represented by $R_1$ is optionally substituted with one or more substituents independently selected from the group consisting of —OH, —Br, —Cl, —I, —F, —$R^a$, —$OR^a$, —$COOR^a$, —CN, —$NO_2$, morpholinyl, piperidinyl, and pyrrolidinyl, wherein $R^a$ is a lower alkyl or a lower haloalkyl. Values and specific values for the remainder of the variables are as described above in the nineteenth embodiment.

In a twenty-first embodiment, for structural formulas (XLV-(XLIX), $R_3$ is —H, an optionally substituted lower alkyl, an optionally substituted alkenyl, an optionally substituted alkynyl, an optionally substituted cycloalkyl, an optionally substituted phenyl or an optionally substituted benzyl. More specifically, $R_3$ is —H, methyl, ethyl, propyl, butyl, pentyl, hexyl, cyclopropyl, cyclobutyl, phenyl or benzyl, wherein the phenyl and benzyl represented by $R_3$ and $R_4$ is optionally substituted with —OH, —Br, —Cl, —I, —F, —$R^a$, —$OR^a$, —$COOR^a$, —CN, —$NO_2$, morpholinyl, piperidinyl, and pyrrolidinyl, wherein $R^a$ is a lower alkyl or a lower haloalkyl. Even more specifically, $R_3$ is methyl, ethyl or phenyl. Values and specific values for the remainder of the variables are as described above in the twentieth embodiment.

In a twenty-second embodiment, the compound is represented by the following structural formula:

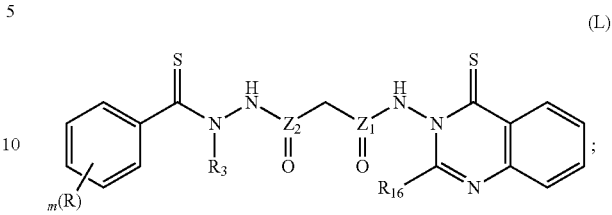
(L)

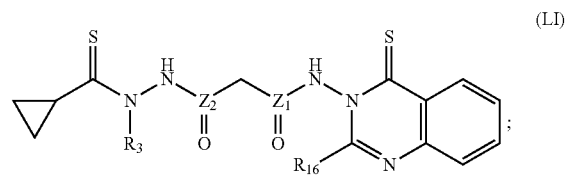
(LI)

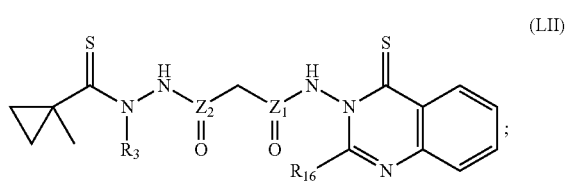
(LII)

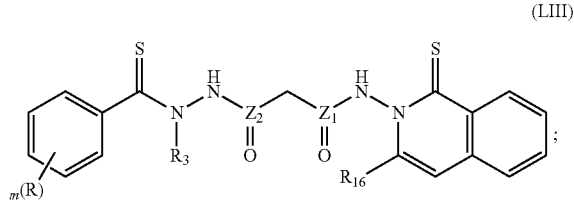
(LIII)

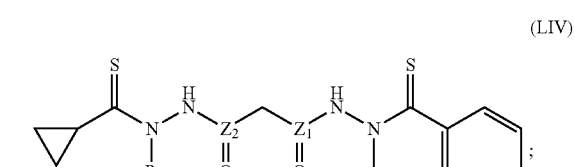
(LIV)

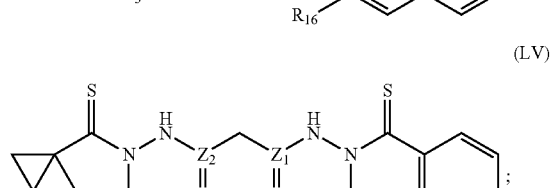
(LV)

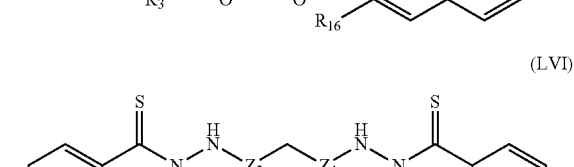
(LVI)

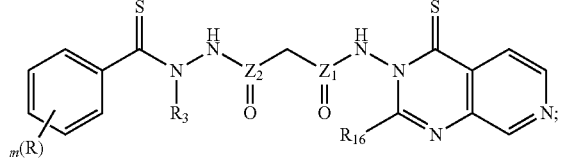

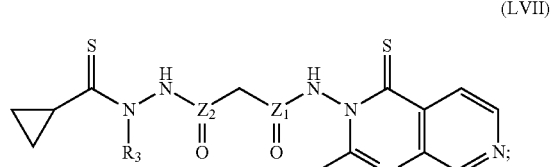
(LVII)

-continued

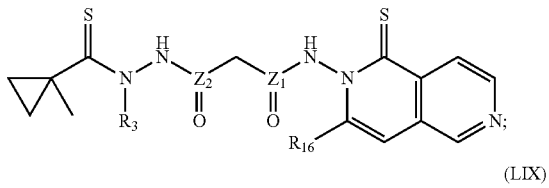
(LVIII)

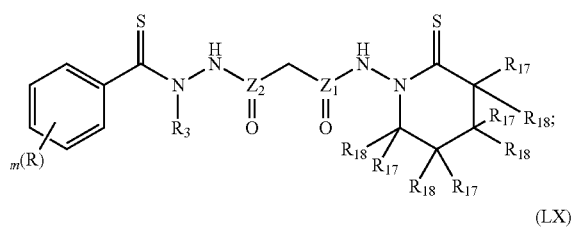
(LIX)

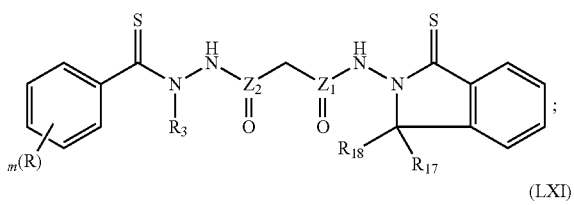
(LX)

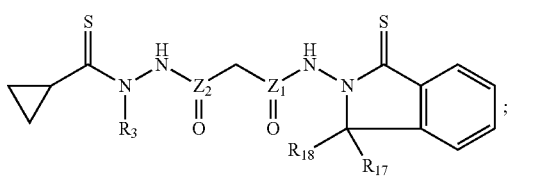
(LXI)

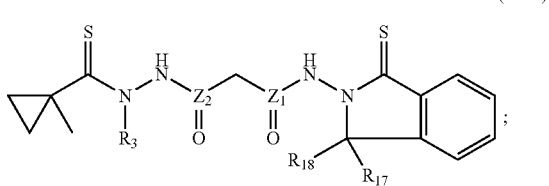
(LXII)

or a pharmaceutically acceptable salt or a transition metal chelate, coordinate or complex of the compound or a transition metal chelate, coordinate or complex of a deprotonated form of the compound, wherein:

R for each occurrence is independently selected from the group consisting of —H, —OH, —Br, —Cl, —I, —F, —$R^a$, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—$N(R^aR^b)$, —$NR^d$—C(=NH)—$NH_2$, —$NR^d$—C(=NH)—$NHR^a$, —$NR^d$—C(=NH)—$N(R^aR^b)$, —$NR^d$—C(=$NR^c$)—$NH_2$, —$NR^d$—C(=$NR^c$)—$NHR^a$, —$NR^d$—C(=$NR^c$)—$N(R^aR^b)$, —$NHNH_2$, —$NHNHR^a$, —$NHN(R^aR^b)$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —$S(O)R^a$, —$S(O)_2 R^a$, heterocyclic group, benzyl group and aryl group;

$R^a$-$R^d$ are each independently a lower alkyl, a lower haloalkyl, a lower alkoxy, a lower hydroxyalkyl, benzyl, aryl, or, —$NR^aR^d$, taken together, can also form an optionally substituted heterocyclic group; and m is 1, 2, 3, 4, or 5.

Values and specific values for the remainder of the variables in structural formulas (L)-(LXII) are as described in the nineteenth or twenty-first embodiment. More specifically, R is selected from the group consisting of —H, —OH, —Br, —Cl, —I, —F, —$R^a$, —$OR^a$, —$COOR^a$, —CN, —$NO_2$, morpholinyl, piperidinyl and pyrrolidinyl, wherein $R^a$ is a lower alkyl or a lower haloalkyl; and m is 1 or 2.

In a twenty-third embodiment, the compound is represented by the following structural formula:

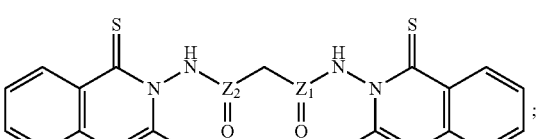
(LXIII)

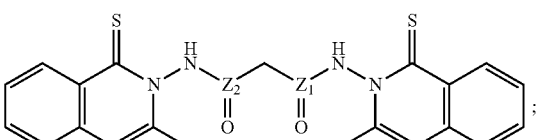
(LXIV)

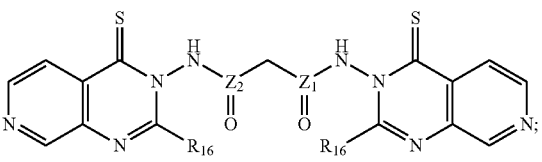
(LXV)

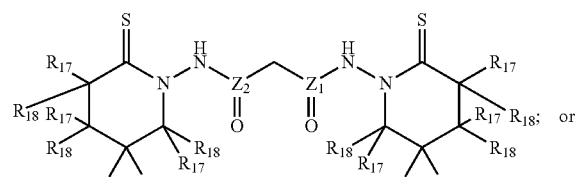
(LXVI)

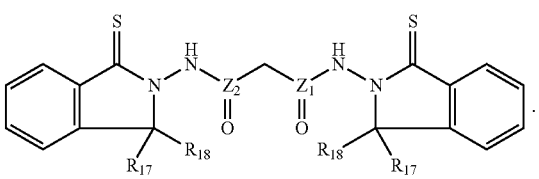
(LXVII)

Values and specific values for the variables in formulas (LXIII)-(LXVII) are as described in nineteenth embodiment. More specifically, $R_{16}$, $R_{17}$ and $R^{18}$ are each independently selected from the group consisting of —H, —$R^a$, —OH, —Br, —Cl, —I, —F and —$OR^a$. Even more specifically, $R_{16}$ is —H or methyl and $R_{17}$ and $R_{18}$ are —H.

In a twenty-fourth embodiment, the compound is represented by the following structural formula:

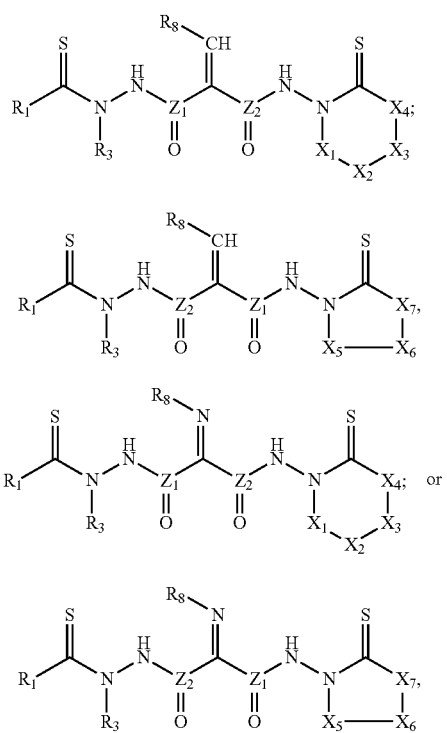

or a pharmaceutically acceptable salt or a transition metal chelate, coordinate or complex of the compound or a transition metal chelate, coordinate or complex of a deprotonated form of the compounds, wherein $R_8$ is as described for structural formula (I) and values and specific values for the remainder of the variables are as described above in the eighteenth embodiment.

In a twenty-fifth embodiment, the compound is represented by the following structural formula:

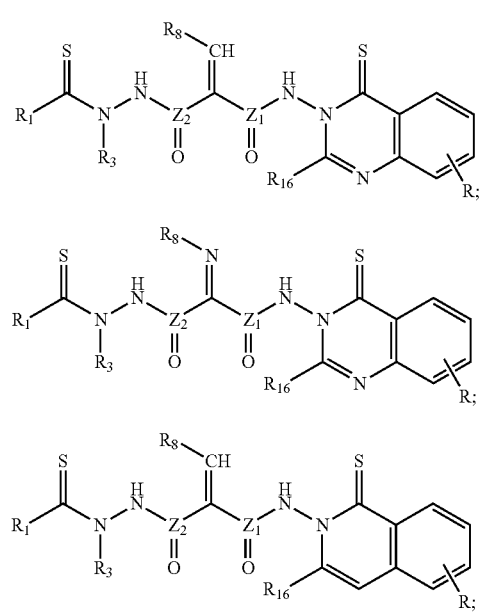

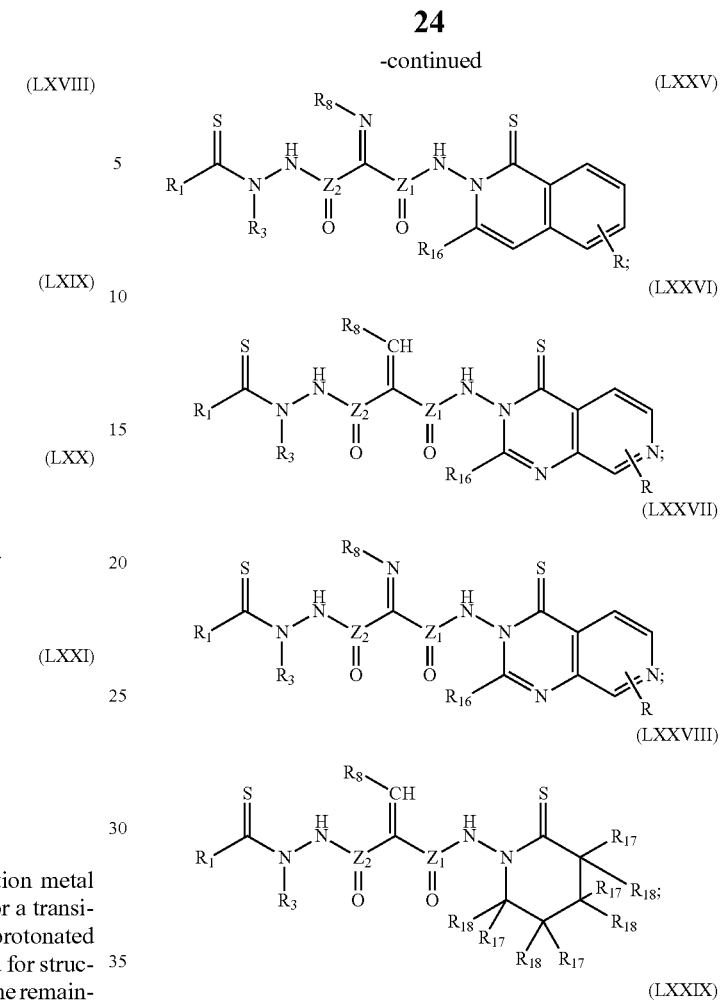

or a pharmaceutically acceptable salt or a transition metal chelate, coordinate or complex of the compound or a transition metal chelate, coordinate or complex of a deprotonated form of the compound. Values and specific values for $R_8$ are as described above for structural formula (I) and values and specific values for the remainder of the variables are as described in the nineteenth embodiment. More specifically, $R_8$ is selected from the group consisting of —OH, —NR$_{10}$R$_{11}$, a lower alkoxy, a lower alkyl, wherein the lower alkyl and the lower alkoxy is optionally substituted with halogen or —OH; $R_{10}$ and $R_{11}$ are each independently —H, —OH or a lower alkyl or a (C$_3$-C$_6$)cycloalkyl. Even more specifically, $R_8$ is —NR$_{10}$R$_{11}$, wherein $R_{10}$ and $R_{11}$ are each independent selected from the group —H, —OH, methyl, ethyl, propyl and cyclopropyl.

In a twenty-sixth embodiment, values and specific values for $R_1$ are as described in the twentieth embodiment and values and specific values for $R_3$ are as described in the twenty-first embodiment. Values and specific values for the remainder of the variables are as described above in the twenty-fifth embodiment.

In a twenty-seventh embodiment, for structural formulas (LXXII)-(LXXXI), $R_1$ is —NR$_{12}$R$_{13}$, —OR$_{14}$ or —SR$_{14}$. More specifically, $R_{12}$, $R_{13}$ and $R_{14}$ are each independently —H, an optionally substituted lower alkyl, an optionally substituted phenyl or an optionally substituted benzyl, or $R_{12}$ and $R_{13}$, taken together with the nitrogen atom to which they are attached, form an optionally substituted five to six-membered heterocyclic group or an optionally substituted five to six-membered heteroaryl group, wherein the alkyl represented by $R_{12}$, $R_{13}$ and $R_{14}$ is optionally substituted with —OH, —Br, —Cl, —I, —F, —R$^a$, —OR$^a$ or —COOR$^a$, and the phenyl and benzyl represented by $R_{12}$, $R_{13}$ and $R_{14}$ or the heterocyclic or heteroaryl group represented by —NR$_{12}$R$_{13}$ are optionally substituted with —OH, —Br, —Cl, —I, —F, —R$^a$, —OR$^a$, —COOR$^a$, —CN, —NO$_2$, morpholinyl, piperidinyl, and pyrrolidinyl, wherein R$^a$ is a lower alkyl or a lower haloalkyl. Even more specifically, $R_{12}$, $R_{13}$ and $R_{14}$ are each independently —H, (C$_1$-C$_4$)alkyl, (C$_1$-C$_4$)haloalkyl, or phenyl optionally substituted with —OH, —Br, —Cl, —I, —F, —R$^a$, —OR$^a$, —COOR$^a$, —CN, —NO$_2$, morpholinyl, piperidinyl or pyrrolidinyl; or $R_{12}$ and $R_{13}$ taken together with the nitrogen to which they are attached form a heterocyclic group or a heteroaryl group selected from the group consisting of pyrrolidinyl, piperidinyl, morpholinyl, pyridinyl, pyrazinyl and imidazolyl, each of which is optionally substituted with —OH, —Br, —Cl, —I, —F, —R$^a$, —OR$^a$, —C(O)OR$^a$, —CN and —NO$_2$, wherein R$^a$ is a lower alkyl or a lower haloalkyl. Values and specific values for the remainder of the variables are as described above in the twenty-fifth embodiment.

In a twenty-eighth embodiment, for structural formulas (LXXII)-(LXXXI), values and specific values for $R_3$ are as described above in the twenty-first embodiment and values and specific values for the remainder of the variables are as described above in the twenty-seventh embodiment.

Examples of the compounds of the invention are represented by the following structural formulas or a pharmaceutically acceptable salt or a transition metal chelate, coordinate or complex of the compound or a transition metal chelate, coordinate or complex of a deprotonated form of the compound.

| Compound No. | Structure | Chemical Name |
|---|---|---|
| 1 | 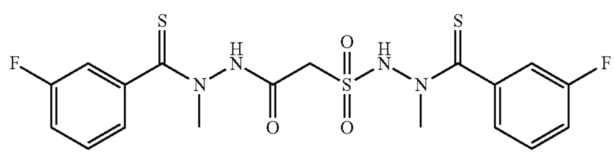 [SMILES: CN(NC(=O)CS(=O)(=O)NN(C)C(=S)c1cccc(F)c1)C(=S)c1cccc(F)c1] | N'-(3-fluorophenylcarbonothioyl)-2-(2-(3-fluorophenylcarbonothioyl)-2-methylhydrazinyl)-N'-methyl-2-oxoethanesulfonohydrazide |
| 2 | 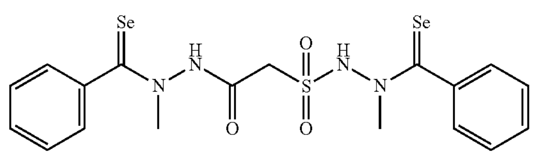 [SMILES: CN(NC(=O)CS(=O)(=O)NN(C)C(=[Se])c1ccccc1)C(=[Se])c1ccccc1] | N'-methyl-2-(2-methyl-2-(phenylcarbonoselenoyl)-hydrazinyl)-2-oxo-N'-(phenylcarbonoselenoyl)ethanesulfonohydrazide |
| 3 | 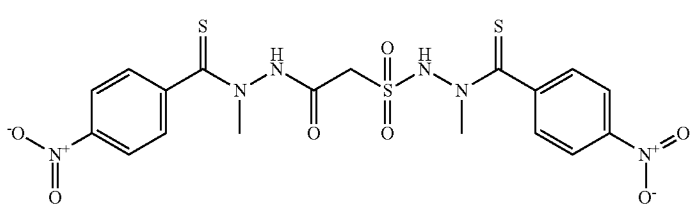 | N'-methyl-2-(2-methyl-2-(4-nitrophenylcarbonothioyl)-hydrazinyl)-N'-(4-nitrophenylcarbonothioyl)-2-oxoethanesulfonohydrazide |
| 4 | 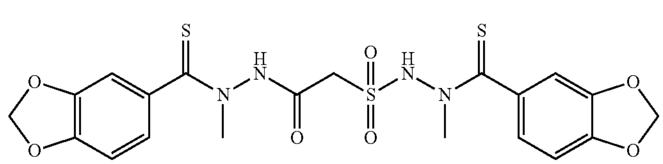 [SMILES: CN(NC(=O)CS(=O)(=O)NN(C)C(=S)c1ccc2c(c1)OCO2)C(=S)c1ccc2c(c1)OCO2] | N'-(benzo[d][1,3]dioxole-5-carbonothioyl)-2-(2-(benzo[d][1,3]dioxole-5-carbonothioyl)-2-methylhydrazinyl)-N'-methyl-2-oxoethanesulfonohydrazide |

| Compound No. | Structure | Chemical Name |
|---|---|---|
| 5 | 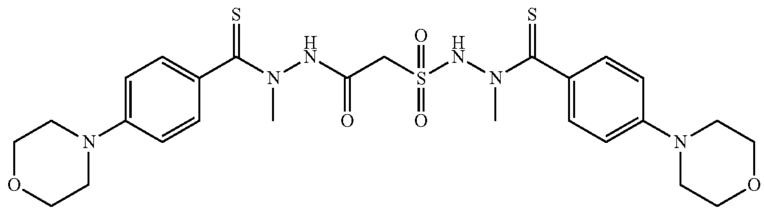 [SMILES: CN(NC(=O)CS(=O)(=O)NN(C)C(=S)c1ccc(N2CCOCC2)cc1)C(=S)c1ccc(N2CCOCC2)cc1] | N'-methyl-2-(2-methyl-2-(4-morpholinophenylcarbonothioyl)hydrazinyl)-N'-(4-morpholinophenylcarbonothioyl)-2-oxoethanesulfonohydrazide |
| 6 | 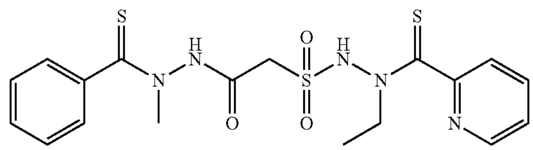 [SMILES: CCN(NS(=O)(=O)CC(=O)NN(C)C(=S)c1ccccc1)C(=S)c1ccccn1] | N'-ethyl-2-(2-methyl-2-(phenylcarbonothioyl)hydrazinyl)-2-oxo-N'-(pyridine-2-carbonothioyl)ethanesulfonohydrazide |
| 7 | 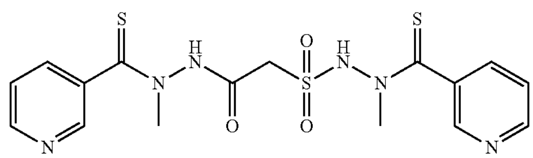 [SMILES: CN(NC(=O)CS(=O)(=O)NN(C)C(=S)c1cccnc1)C(=S)c1cccnc1] | N'-methyl-2-(2-methyl-2-(pyridine-3-carbonothioyl)hydrazinyl)-2-oxo-N'-(pyridine-3-carbonothioyl)-ethanesulfonohydrazide |
| 8 | 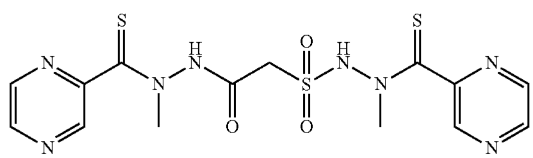 [SMILES: CN(NC(=O)CS(=O)(=O)NN(C)C(=S)c1cnccn1)C(=S)c1cnccn1] | N'-methyl-2-(2-methyl-2-(pyrazine-2-carbonothioyl)hydrazinyl)-2-oxo-N'-(pyrazine-2-carbonothioyl)-ethanesulfonohydrazide |
| 9 | 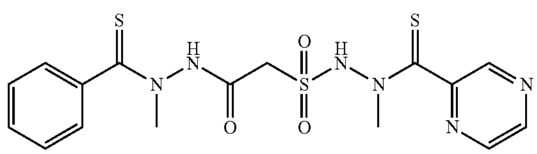 [SMILES: CN(NC(=O)CS(=O)(=O)NN(C)C(=S)c1cnccn1)C(=S)c1ccccc1] | N'-methyl-2-(2-methyl-2-(phenylcarbonothioyl)hydrazinyl)-2-oxo-N'-(pyrazine-2-carbonothioyl)-ethanesulfonohydrazide |
| 10 | 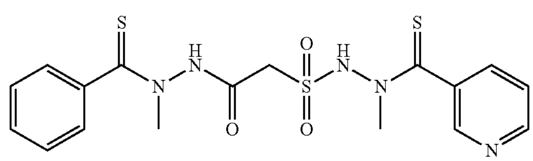 [SMILES: CN(NC(=O)CS(=O)(=O)NN(C)C(=S)c1cccnc1)C(=S)c1ccccc1] | N'-methyl-2-(2-methyl-2-(phenylcarbonothioyl)hydrazinyl)-2-oxo-N'-(pyridine-3-carbonothioyl)-ethanesulfonohydrazide |
| 11 | 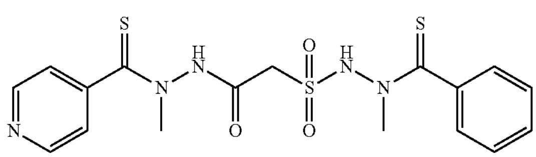 [SMILES: CN(NC(=O)CS(=O)(=O)NN(C)C(=S)c1ccccc1)C(=S)c1ccncc1] | N'-methyl-2-(2-methyl-2-(pyridine-4-carbonothioyl)hydrazinyl)-2-oxo-N'-(phenylcarbonothioyl)ethane-sulfonohydrazide |
| 12 | 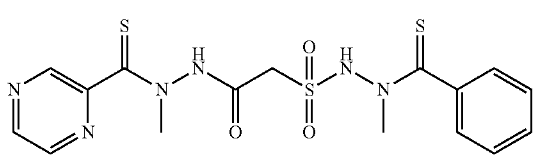 [SMILES: CN(NS(=O)(=O)CC(=O)NN(C)C(=S)c1cnccn1)C(=S)c1ccccc1] | N'-methyl-2-(2-methyl-2-(pyrazine-2-carbonothioyl)hydrazinyl)-2-oxo-N'-(phenylcarbonothioyl)ethane-sulfonohydrazide |
| 13 | 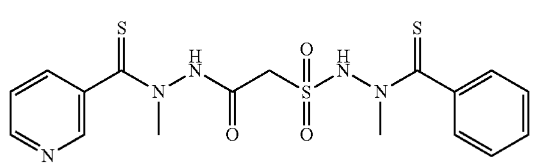 [SMILES: CN(NC(=O)CS(=O)(=O)NN(C)C(=S)c1ccccc1)C(=S)c1cccnc1] | N'-methyl-2-(2-methyl-2-(pyridine-3-carbonothioyl)hydrazinyl)-2-oxo-N'-(phenylcarbonothioyl)ethane-sulfonohydrazide |

-continued

| Compound No. | Structure | Chemical Name |
|---|---|---|
| 14 | 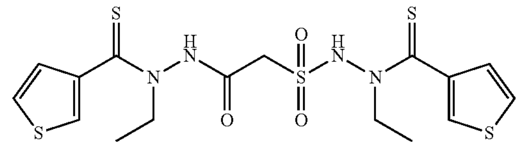 [SMILES: CCN(NC(=O)CS(=O)(=O)NN(CC)C(=S)c1ccsc1)C(=S)c1ccsc1] | N'-ethyl-2-(2-ethyl-2-(thiophene-3-carbonothioyl)hydrazinyl)-2-oxo-N'-(thiophene-3-carbonothioyl)-ethanesulfonohydrazide |
| 15 | 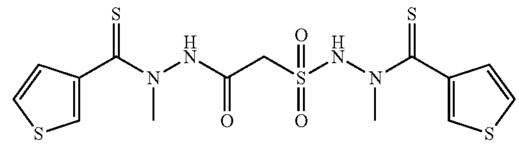 [SMILES: CN(NC(=O)CS(=O)(=O)NN(C)C(=S)c1ccsc1)C(=S)c1ccsc1] | N'-methyl-2-(2-methyl-2-(thiophene-3-carbonothioyl)hydrazinyl)-2-oxo-N'-(thiophene-3-carbonothioyl)-ethanesulfonohydrazide |
| 16 | 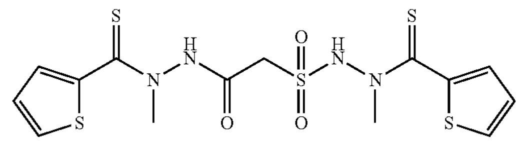 [SMILES: CN(NC(=O)CS(=O)(=O)NN(C)C(=S)c1cccs1)C(=S)c1cccs1] | N'-methyl-2-(2-methyl-2-(thiophene-2-carbonothioyl)hydrazinyl)-2-oxo-N'-(thiophene-2-carbonothioyl)-ethanesulfonohydrazide |
| 17 | 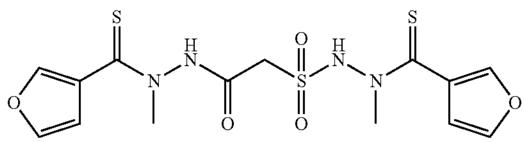 [SMILES: CN(NC(=O)CS(=O)(=O)NN(C)C(=S)c1ccoc1)C(=S)c1ccoc1] | N'-(furan-3-carbonothioyl)-2-(2-(furan-3-carbonothioyl)-2-methylhydrazinyl)-N'-methyl-2-oxoethanesulfonohydrazide |
| 18 | 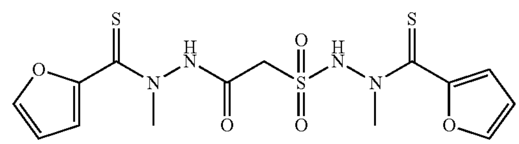 [SMILES: CN(NC(=O)CS(=O)(=O)NN(C)C(=S)c1ccco1)C(=S)c1ccco1] | N'-(furan-2-carbonothioyl)-2-(2-(furan-2-carbonothioyl)-2-methylhydrazinyl)-N'-methyl-2-oxoethanesulfonohydrazide |
| 19 | 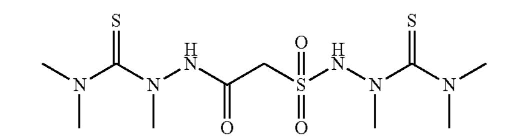 | 2-(2-(2-(dimethylcarbamothioyl)-2-methylhydrazinyl)-2-oxoethylsulfonyl)-N,N,1-trimethylhydrazinecarbothioamide |
| 20 | 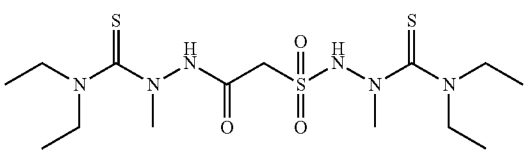 [SMILES: CCN(CC)C(=S)N(C)NC(=O)CS(=O)(=O)NN(C)C(=S)N(CC)CC] | 2-(2-(2-(diethylcarbamothioyl)-2-methylhydrazinyl)-2-oxoethylsulfonyl)-N,N'-diethyl-1-methylhydrazinecarbothioamide |
| 21 | 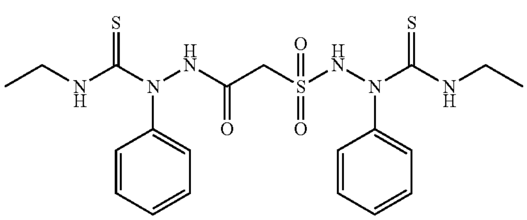 [SMILES: CCNC(=S)N(NC(=O)CS(=O)(=O)NN(C(=S)NCC)c1ccccc1)c1ccccc1] | N'-ethyl-2-(2-(2-(ethylcarbamothioyl)-2-phenylhydrazinyl)-2-oxoethylsulfonyl)-1-phenylhydrazinecarbothioamide |
| 22 | 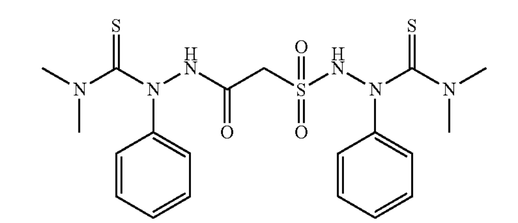 | 2-(2-(2-(dimethylcarbamothioyl)-2-phenylhydrazinyl)-2-oxoethylsulfonyl)-N,N'-dimethyl-1-phenylhydrazinecarbothioamide |

-continued

| Compound No. | Structure | Chemical Name |
|---|---|---|
| 23 | 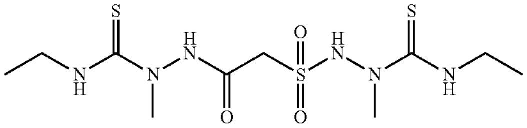 [SMILES: CCNC(=S)N(C)NC(=O)CS(=O)(=O)NN(C)C(=S)NCC] | N'-ethyl-2-(2-(2-(ethylcarbamothioyl)-2-methylhydrazinyl)-2-oxoethylsulfonyl)-1-methylhydrazinecarbothioamide |
| 24 | 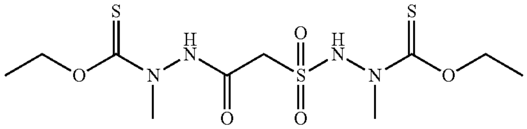 [SMILES: CCOC(=S)N(C)NC(=O)CS(=O)(=O)NN(C)C(=S)OCC] | O-ethyl 2-(2-(2-(ethoxycarbonothioyl)-2-methylhydrazinyl)-2-oxoethylsulfonyl)-1-methylhydrazinecarbothioate |
| 25 | 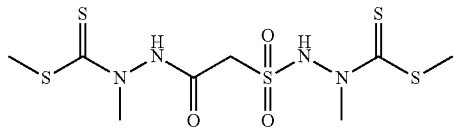 | methyl 1-methyl-2-(2-(2-methyl-2-(methylthiocarbonothioyl)-hydrazinyl)-2-oxoethylsulfonyl)hydrazinecarbodithioate |
| 26 | 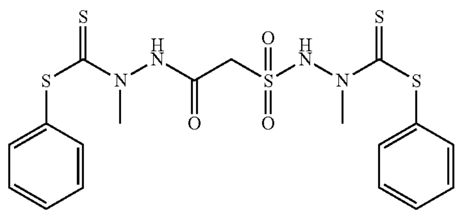 [SMILES: CN(NC(=O)CS(=O)(=O)NN(C)C(=S)Sc1ccccc1)C(=S)Sc1ccccc1] | phenyl 1-methyl-2-(2-(2-methyl-2-(phenylthiocarbonothioyl)-hydrazinyl)-2-oxoethylsulfonyl)hydrazinecarbodithioate |
| 27 | 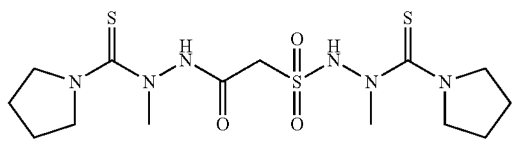 [SMILES: CN(NC(=O)CS(=O)(=O)NN(C)C(=S)N1CCCC1)C(=S)N1CCCC1] | N'-methyl-2-(2-methyl-2-(pyrrolidine-1-carbonothioyl)hydrazinyl)-2-oxo-N'-(pyrrolidine-1-carbonothioyl)-ethanesulfonohydrazide |
| 28 | 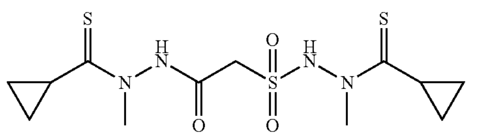 [SMILES: CN(NC(=O)CS(=O)(=O)NN(C)C(=S)C1CC1)C(=S)C1CC1] | N'-(cyclopropanecarbonothioyl)-2-(2-(cyclopropanecarbonothioyl)-2-methylhydrazinyl)-N'-methyl-2-oxoethanesulfonohydrazide |
| 29 | 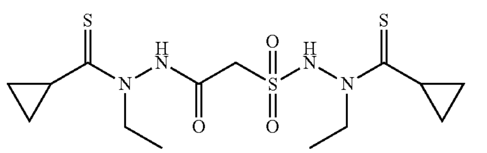 [SMILES: CCN(NC(=O)CS(=O)(=O)NN(CC)C(=S)C1CC1)C(=S)C1CC1] | N'-(cyclopropanecarbonothioyl)-2-(2-(cyclopropanecarbonothioyl)-2-ethylhydrazinyl)-N'-ethyl-2-oxoethanesulfonohydrazide |
| 30 | 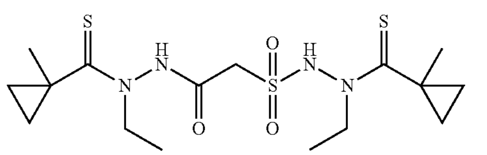 [SMILES: CCN(NC(=O)CS(=O)(=O)NN(CC)C(=S)C1(C)CC1)C(=S)C1(C)CC1] | N'-ethyl-2-(2-ethyl-2-(1-methylcyclopropanecarbonothioyl)hydrazinyl)-N'-(1-methylcyclopropanecarbonothioyl)-2-oxoethanesulfonohydrazide |
| 31 | 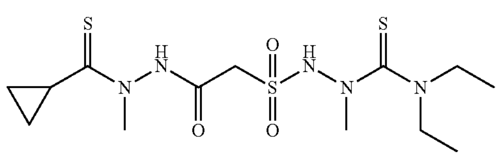 [SMILES: CCN(CC)C(=S)N(C)NS(=O)(=O)CC(=O)NN(C)C(=S)C1CC1] | 2-(2-(2-(cyclopropanecarbonothioyl)-2-methylhydrazinyl)-2-oxoethylsulfonyl)-N,N'-diethyl-1-methylhydrazinecarbothioamide |
| 32 | 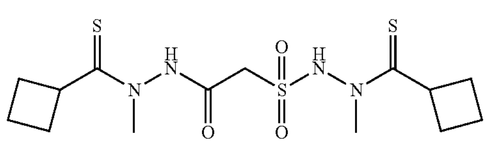 [SMILES: CN(NC(=O)CS(=O)(=O)NN(C)C(=S)C1CCC1)C(=S)C1CCC1] | N'-(cyclobutanecarbonothioyl)-2-(2-(cyclobutanecarbonothioyl)-2-methylhydrazinyl)-N'-methyl-2-oxoethanesulfonohydrazide |

-continued

| Compound No. | Structure | Chemical Name |
|---|---|---|
| 33 | 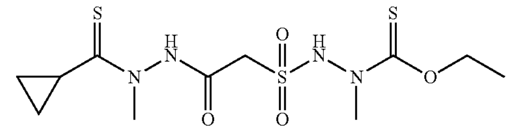 [SMILES: CCOC(=S)N(C)NS(=O)(=O)CC(=O)NN(C)C(=S)C1CC1] | O-ethyl 2-(2-(2-(cyclopropanecarbonothioyl)-2-methylhydrazinyl)-2-oxoethylsulfonyl)-1-methylhydrazinecarbothioate |
| 34 | 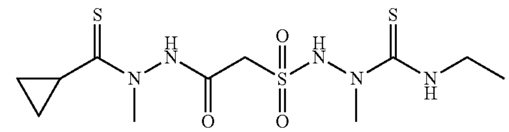 [SMILES: CCNC(=S)N(C)NS(=O)(=O)CC(=O)NN(C)C(=S)C1CC1] | 2-(2-(2-(cyclopropanecarbonothioyl)-2-methylhydrazinyl)-2-oxoethylsulfonyl)-N'-ethyl-1-methylhydrazinecarbothioamide |
| 35 | 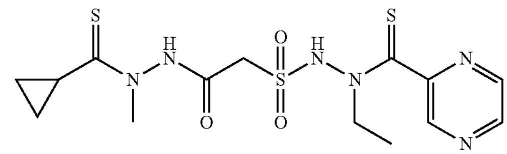 [SMILES: CCN(NS(=O)(=O)CC(=O)NN(C)C(=S)C1CC1)C(=S)c1cnccn1] | 2-(2-(cyclopropanecarbonothioyl)-2-methylhydrazinyl)-N'-ethyl-2-oxo-N'-(pyrazine-2-carbonothioyl)-ethanesulfonohydrazide |
| 36 | 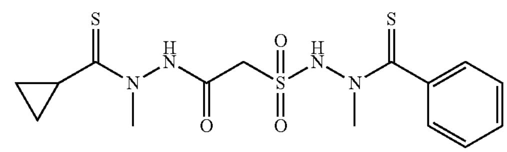 [SMILES: CN(NS(=O)(=O)CC(=O)NN(C)C(=S)C1CC1)C(=S)c1ccccc1] | 2-(2-(cyclopropanecarbonothioyl)-2-methylhydrazinyl)-N'-methyl-2-oxo-N'-(phenylcarbonothioyl)ethane-sulfonohydrazide |
| 37 | 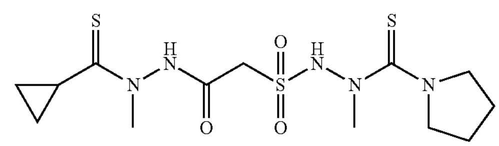 [SMILES: CN(NC(=O)CS(=O)(=O)NN(C)C(=S)N1CCCC1)C(=S)C1CC1] | 2-(2-(cyclopropanecarbonothioyl)-2-methylhydrazinyl)-N'-methyl-2-oxo-N'-(pyrrolidine-1-carbonothioyl)-ethanesulfonohydrazide |
| 38 | 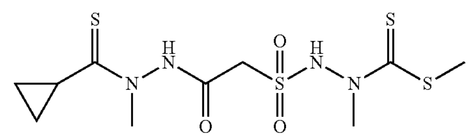 [SMILES: CSC(=S)N(C)NS(=O)(=O)CC(=O)NN(C)C(=S)C1CC1] | methyl 2-(2-(2-(cyclopropanecarbonothioyl)-2-methylhydrazinyl)-2-oxoethylsulfonyl)-1-methylhydrazinecarbodithioate |
| 39 | 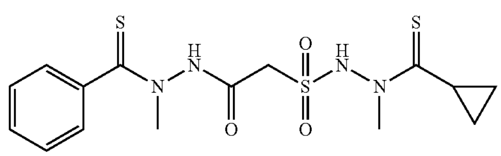 [SMILES: CN(NC(=O)CS(=O)(=O)NN(C)C(=S)C1CC1)C(=S)c1ccccc1] | N'-(cyclopropanecarbonothioyl)-N'-methyl-2-(2-methyl-2-(phenylcarbonothioyl)hydrazinyl)-2-oxoethanesulfonohydrazide |
| 40 | 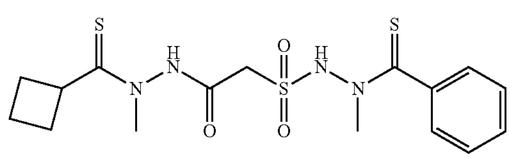 [SMILES: CN(NS(=O)(=O)CC(=O)NN(C)C(=S)C1CCC1)C(=S)c1ccccc1] | 2-(2-(cyclobutanecarbonothioyl)-2-methylhydrazinyl)-N'-methyl-2-oxo-N'-(phenylcarbonothioyl)ethane-sulfonohydrazide |
| 41 | 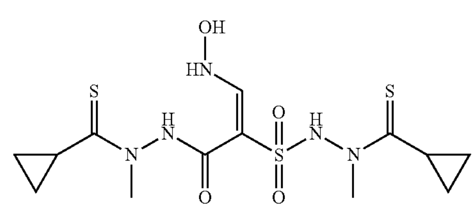 [SMILES: CN(NC(=O)/C(=C\NO)S(=O)(=O)NN(C)C(=S)C1CC1)C(=S)C1CC1] | (E)-N'-(cyclopropanecarbonothioyl)-3-(2-(cyclopropanecarbonothioyl)-2-methylhydrazinyl)-1-(hydroxyamino)-N'-methyl-3-oxoprop-1-ene-2-sulfonohydrazide |
| 42 | 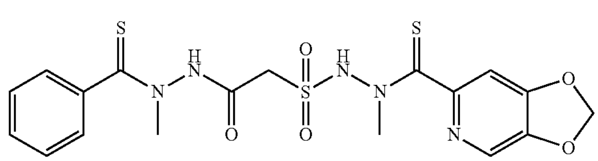 [SMILES: CN(NC(=O)CS(=O)(=O)NN(C)C(=S)c1cc2c(cn1)OCO2)C(=S)c1ccccc1] | N'-([1,3]dioxolo[4,5-c]pyridine-6-carbonothioyl)-N'-methyl-2-(2-methyl-2-(phenylcarbonothioyl)hydrazinyl)-2-oxoethanesulfonohydrazide |

-continued

| Compound No. | Structure | Chemical Name |
|---|---|---|
| 43 | 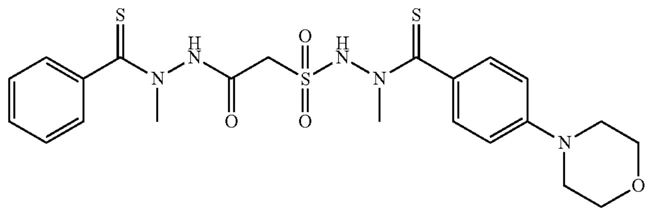 [SMILES: CN(NC(=O)CS(=O)(=O)NN(C)C(=S)c1ccc(N2CCOCC2)cc1)C(=S)c1ccccc1] | N'-methyl-2-(2-methyl-2-(phenylcarbonothioyl)hydrazinyl)-N'-(4-morpholinophenylcarbonothioyl)-2-oxoethanesulfonohydrazide |
| 44 | 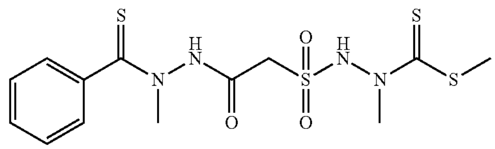 [SMILES: CSC(=S)N(C)NS(=O)(=O)CC(=O)NN(C)C(=S)c1ccccc1] | methyl 1-methyl-2-(2-(2-methyl-2-(phenylcarbonothioyl)hydrazinyl)-2-oxoethylsulfonyl)hydrazinecarbodithioate |
| 45 | 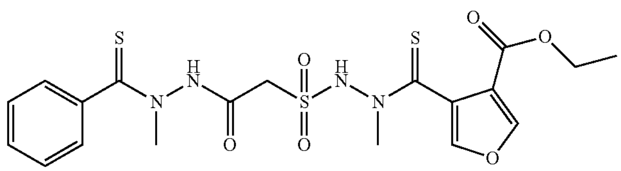 [SMILES: CCOC(=O)c1cocc1C(=S)N(C)NS(=O)(=O)CC(=O)NN(C)C(=S)c1ccccc1] | ethyl 4-(1-methyl-2-(2-(2-methyl-2-(phenylcarbonothioyl)hydrazinyl)-2-oxoethylsulfonyl)hydrazinecarbonothioyl)furan-3-carboxylate |
| 46 | 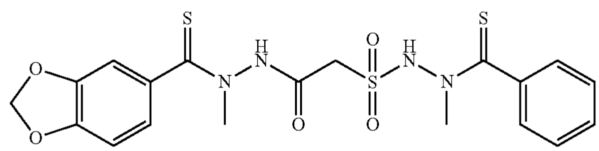 [SMILES: CN(NC(=O)CS(=O)(=O)NN(C)C(=S)c1ccccc1)C(=S)c1ccc2c(c1)OCO2] | 2-(2-(benzo[d][1,3]dioxole-5-carbonothioyl)-2-methylhydrazinyl)-N'-methyl-2-oxo-N'-(phenylcarbonothioyl)ethanesulfonohydrazide |
| 47 | 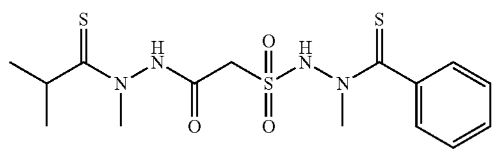 [SMILES: CC(C)C(=S)N(C)NC(=O)CS(=O)(=O)NN(C)C(=S)c1ccccc1] | N'-methyl-2-(2-methyl-2-(2-methylpropanethioyl)hydrazinyl)-2-oxo-N'-(phenylcarbonothioyl)ethanesulfonohydrazide |
| 48 | 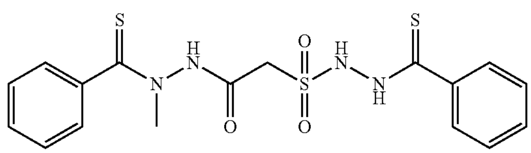 [SMILES: CN(NC(=O)CS(=O)(=O)NNC(=S)c1ccccc1)C(=S)c1ccccc1] | 2-(2-methyl-2-(phenylcarbonothioyl)hydrazinyl)-2-oxo-N'-(phenylcarbonothioyl)ethanesulfonohydrazide |
| 49 | 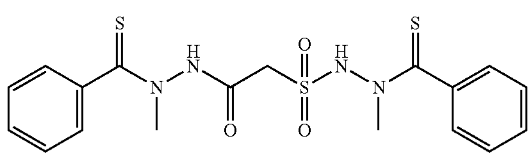 [SMILES: CN(NC(=O)CS(=O)(=O)NN(C)C(=S)c1ccccc1)C(=S)c1ccccc1] | N'-benzoyl-N'-methyl-2-(2-methyl-2-(phenylcarbonothioyl)hydrazinyl)-2-oxoethanesulfonohydrazide |
| 50 | 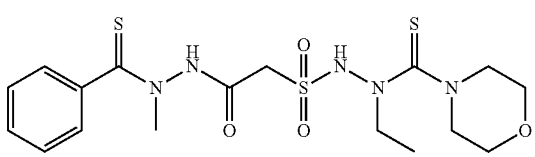 [SMILES: CCN(NS(=O)(=O)CC(=O)NN(C)C(=S)c1ccccc1)C(=S)N1CCOCC1] | N'-ethyl-2-(2-methyl-2-(phenylcarbonothioyl)hydrazinyl)-N'-(morpholine-4-carbonothioyl)-2-oxoethanesulfonohydrazide |
| 51 | 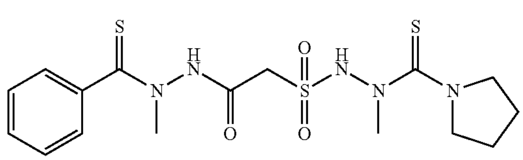 [SMILES: CN(NC(=O)CS(=O)(=O)NN(C)C(=S)N1CCCC1)C(=S)c1ccccc1] | N'-methyl-2-(2-methyl-2-(phenylcarbonothioyl)hydrazinyl)-2-oxo-N'-(pyrrolidine-1-carbonothioyl)-ethanesulfonohydrazide |

-continued

| Compound No. | Structure | Chemical Name |
|---|---|---|
| 52 | 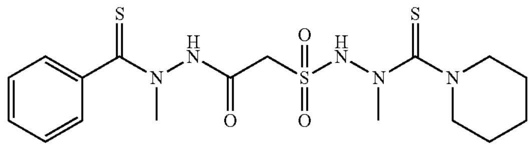 [SMILES: CN(NC(=O)CS(=O)(=O)NN(C)C(=S)N1CCCCC1)C(=S)c1ccccc1] | N'-methyl-2-(2-methyl-2-(phenylcarbonothioyl)hydrazinyl)-2-oxo-N'-(piperidine-1-carbonothioyl)-ethanesulfonohydrazide |
| 53 | 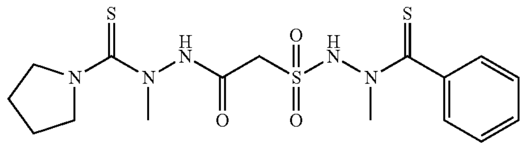 [SMILES: CN(NS(=O)(=O)CC(=O)NN(C)C(=S)N1CCCC1)C(=S)c1ccccc1] | N'-methyl-2-(2-methyl-2-(pyrrolidine-1-carbonothioyl)hydrazinyl)-2-oxo-N'-(phenylcarbonothioyl)ethanesulfonohydrazide |
| 54 | 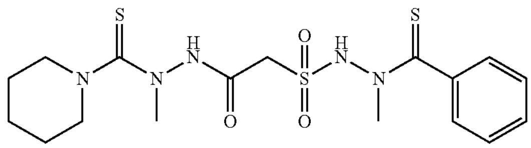 [SMILES: CN(NS(=O)(=O)CC(=O)NN(C)C(=S)N1CCCCC1)C(=S)c1ccccc1] | N'-methyl-2-(2-methyl-2-(piperidine-1-carbonothioyl)hydrazinyl)-2-oxo-N'-(phenylcarbonothioyl)ethanesulfonohydrazide |
| 55 | 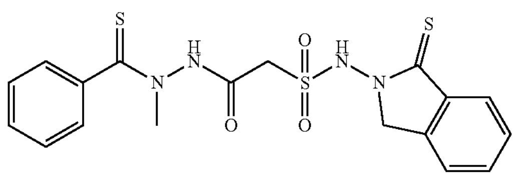 [SMILES: CN(NC(=O)CS(=O)(=O)NN1Cc2ccccc2C1=S)C(=S)c1ccccc1] | 2-(2-methyl-2-(phenylcarbonothioyl)hydrazinyl)-2-oxo-N'-(1-thioxoisoindolin-2-yl)ethanesulfonamide |
| 56 | 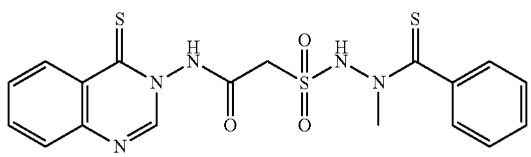 [SMILES: CN(NS(=O)(=O)CC(=O)Nn1cnc2ccccc2c1=S)C(=S)c1ccccc1] | 2-(2-methyl-2-(phenylcarbonothioyl)hydrazinylsulfonyl)-N'-(4-thioxoquinazolin-3(4H)-yl)acetamide |
| 57 | 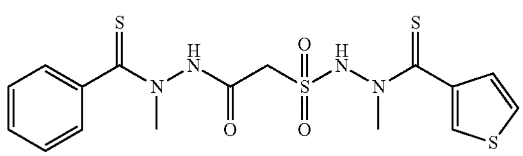 [SMILES: CN(NC(=O)CS(=O)(=O)NN(C)C(=S)c1ccsc1)C(=S)c1ccccc1] | N'-methyl-2-(2-methyl-2-(phenylcarbonothioyl)hydrazinyl)-2-oxo-N'-(thiophene-3-carbonothioyl)ethanesulfonohydrazide |
| 58 | 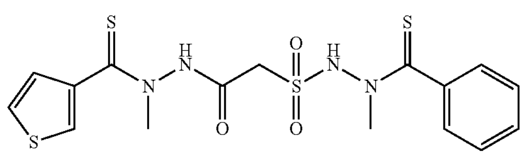 [SMILES: CN(NC(=O)CS(=O)(=O)NN(C)C(=S)c1ccccc1)C(=S)c1ccsc1] | N'-methyl-2-(2-methyl-2-(thiophene-3-carbonothioyl)hydrazinyl)-2-oxo-N'-(phenylcarbonothioyl)ethanesulfonohydrazide |
| 59 | 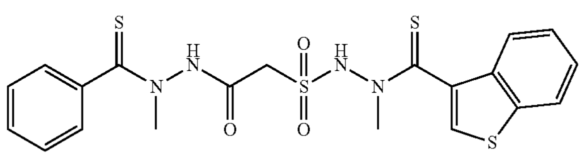 [SMILES: CN(NC(=O)CS(=O)(=O)NN(C)C(=S)c1csc2ccccc12)C(=S)c1ccccc1] | N'-(benzo[b]thiophene-3-carbonothioyl)-N'-methyl-2-(2-methyl-2-((phenylcarbonothioyl)hydrazinyl)-2-oxoethanesulfonohydrazide |
| 60 | 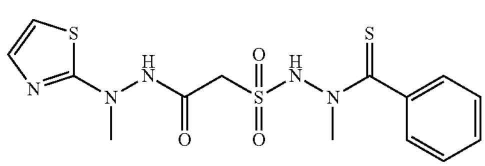 [SMILES: CN(NS(=O)(=O)CC(=O)NN(C)c1nccs1)C(=S)c1ccccc1] | N'-methyl-2-(2-methyl-2-(thiazol-2-yl)hydrazinyl)-2-oxo-N'-(phenylcarbonothioyl)ethanesulfonohydrazide |

-continued

| Compound No. | Structure | Chemical Name |
|---|---|---|
| 61 | 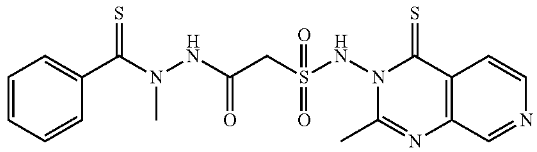 [SMILES: Cc1nc2cnccc2c(=S)n1NS(=O)(=O)CC(=O)NN(C)C(=S)c1ccccc1] | 2-(2-methyl-2-(phenylcarbonothioyl)hydrazinyl)-N'-(2-methyl-4-thioxopyrido[3,4-d]pyrimidin-3(4H)-yl)-2-oxoethanesulfonamide |
| 62 | 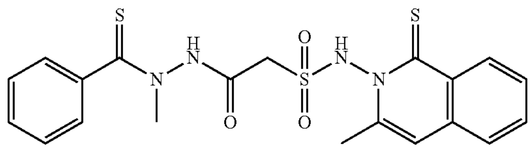 [SMILES: Cc1cc2ccccc2c(=S)n1NS(=O)(=O)CC(=O)NN(C)C(=S)c1ccccc1] | N'-(3-methyl-1-thioxoisoquinolin-2(1H)-yl)-2-(2-methyl-2-(phenylcarbonothioyl)hydrazinyl)-2-oxoethanesulfonamide |
| 63 | 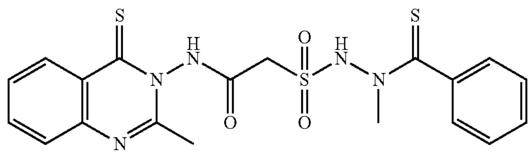 [SMILES: Cc1nc2ccccc2c(=S)n1NC(=O)CS(=O)(=O)NN(C)C(=S)c1ccccc1] | 2-(2-methyl-2-(phenylcarbonothioyl)hydrazinylsulfonyl)-N'-(2-methyl-4-thioxoquinazolin-3(4H)-yl)acetamide |
| 64 | 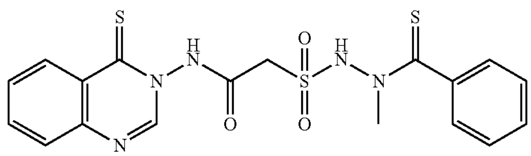 [SMILES: CN(NS(=O)(=O)CC(=O)Nn1cnc2ccccc2c1=S)C(=S)c1ccccc1] | 2-(2-methyl-2-(phenylcarbonothioyl)hydrazinylsulfonyl)-N'-(4-thioxoquinazolin-3(4H)-yl)acetamide |
| 65 | 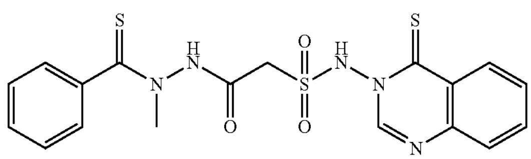 [SMILES: CN(NC(=O)CS(=O)(=O)Nn1cnc2ccccc2c1=S)C(=S)c1ccccc1] | 2-(2-methyl-2-(phenylcarbonothioyl)hydrazinyl)-2-oxo-N'-(4-thioxoquinazolin-3(4H)-yl)ethanesulfonamide |
| 66 | 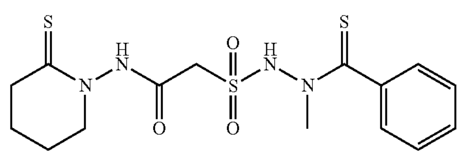 [SMILES: CN(NS(=O)(=O)CC(=O)NN1CCCCC1=S)C(=S)c1ccccc1] | 2-(2-methyl-2-(phenylcarbonothioyl)hydrazinylsulfonyl)-N'-(2-thioxopiperidin-1-yl)acetamide |
| 67 | 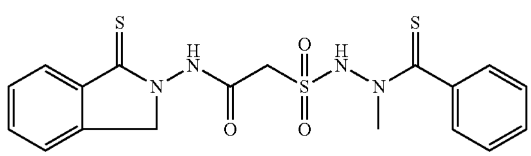 [SMILES: CN(NS(=O)(=O)CC(=O)NN1Cc2ccccc2C1=S)C(=S)c1ccccc1] | 2-(2-methyl-2-(phenylcarbonothioyl)hydrazinylsulfonyl)-N'-(1-thioxoisoindolin-2-yl)acetamide |
| 68 | 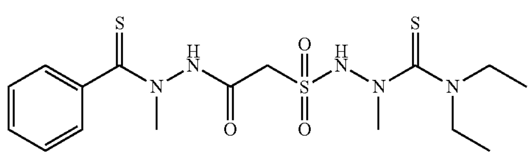 [SMILES: CCN(CC)C(=S)N(C)NS(=O)(=O)CC(=O)NN(C)C(=S)c1ccccc1] | N,N-diethyl-1-methyl-2-(2-(2-methyl-2-(phenylcarbonothioyl)hydrazinyl)-2-oxoethylsulfonyl)hydrazinecarbothioamide |
| 69 | 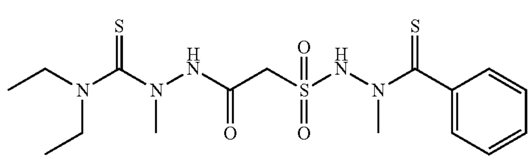 [SMILES: CCN(CC)C(=S)N(C)NC(=O)CS(=O)(=O)NN(C)C(=S)c1ccccc1] | N,N'-diethyl-1-methyl-2-(2-(2-methyl-2-(phenylcarbonothioyl)hydrazinylsulfonyl)acetyl)hydrazinecarbothioamide |

-continued

| Compound No. | Structure | Chemical Name |
|---|---|---|
| 70 | 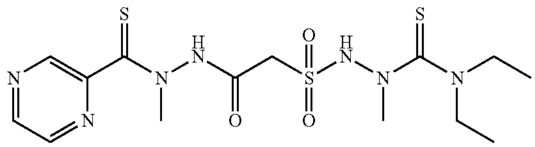 [SMILES: CCN(CC)C(=S)N(C)NS(=O)(=O)CC(=O)NN(C)C(=S)c1cnccn1] | N,N'-diethyl-1-methyl-2-(2-(2-methyl-2-(pyrazine-2-carbonothioyl)hydrazinyl)-2-oxoethylsulfonyl)hydrazine-carbothioamide |
| 71 | 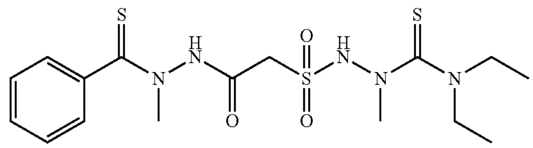 [SMILES: CCN(CC)C(=S)N(C)NS(=O)(=O)CC(=O)NN(C)C(=S)c1ccccc1] | N,N'-diethyl-1-methyl-2-(2-(2-methyl-2-(phenylcarbonothioyl)hydrazinyl)-2-oxoethylsulfonyl)hydrazine-carboxamide |
| 72 | 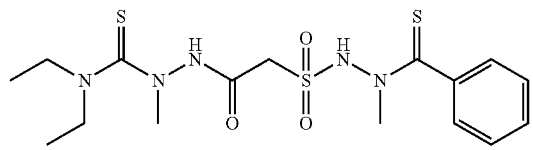 [SMILES: CCN(CC)C(=S)N(C)NC(=O)CS(=O)(=O)NN(C)C(=S)c1ccccc1] | N,N'-diethyl-1-methyl-2-(2-(2-methyl-2-(phenylcarbonothioyl)hydrazinyl-sulfonyl)acetyl)--hydrazinecarboxamide |
| 73 | 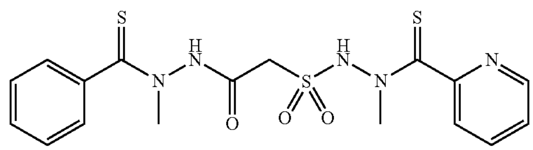 [SMILES: CN(NC(=O)CS(=O)(=O)NN(C)C(=S)c1ccccn1)C(=S)c1ccccc1] | N'-methyl-2-(2-methyl-2-(phenylcarbonothioyl)hydrazinyl)-2-oxo-N'-(pyridine-2-carbonothioyl)-ethanesulfonohydrazide |
| 74 | 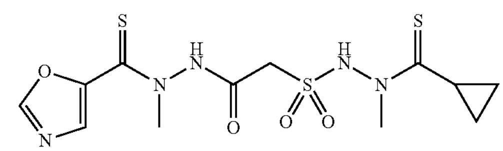 [SMILES: CN(NC(=O)CS(=O)(=O)NN(C)C(=S)C1CC1)C(=S)c1cnco1] | N'-(cyclopropanecarbonothioyl)-N'-methyl-2-(2-methyl-2-(oxazole-5-carbonothioyl)hydrazinyl)-2-oxoethanesulfonohydrazide |
| 75 | 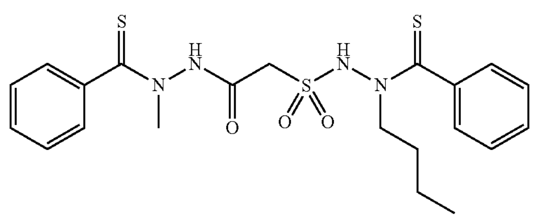 [SMILES: CCCCN(NS(=O)(=O)CC(=O)NN(C)C(=S)c1ccccc1)C(=S)c1ccccc1] | N'-butyl-2-(2-methyl-2-(phenylcarbonothioyl)hydrazinyl)-2-oxo-N'-(phenylcarbonothioyl)ethanesulfonohydrazide |
| 76 | 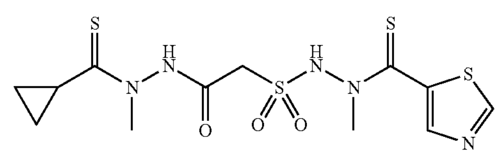 | 2-(2-(cyclopropanecarbonothioyl)-2-methylhydrazinyl)-N'-methyl-2-oxo-N'-(thiazole-5-carbonothioyl)-ethanesulfonohydrazide |
| 77 | 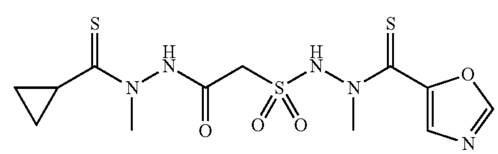 | 2-(2-(cyclopropanecarbonothioyl)-2-methylhydrazinyl)-N'-methyl-N'-(oxazole-5-carbonothioyl)-2-oxoethanesulfonohydrazide |
| 78 | 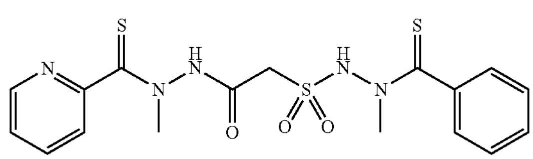 [SMILES: CN(NS(=O)(=O)CC(=O)NN(C)C(=S)c1ccccn1)C(=S)c1ccccc1] | 2-(2-ethyl-2-(pyridine-2-carbonothioyl)hydrazinyl)-N'-methyl-2-oxo-N'-(phenylcarbonothioyl)ethanesulfonohydrazide |

-continued

| Compound No. | Structure | Chemical Name |
|---|---|---|
| 79 | 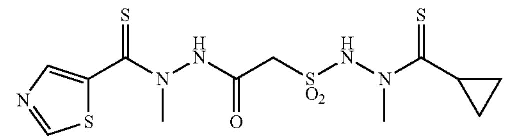 [SMILES: CN(NC(=O)CS(=O)(=O)NN(C)C(=S)C1CC1)C(=S)c1cncs1] | N'-(cyclopropanecarbonothioyl)-N'-methyl-2-(2-methyl-2-(thiazole-5-carbonothioyl)hydrazinyl)-2-oxoethanesulfonohydrazide |
| 80 | 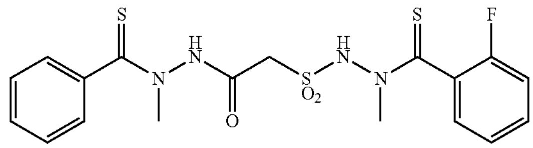 [SMILES: CN(NC(=O)CS(=O)(=O)NN(C)C(=S)c1ccccc1F)C(=S)c1ccccc1] | N'-(2-fluorophenylcarbonothioyl)-N'-methyl-2-(2-methyl-2-(phenylcarbonothioyl)hydrazinyl)-2-oxoethanesulfonohydrazide |
| 81 | 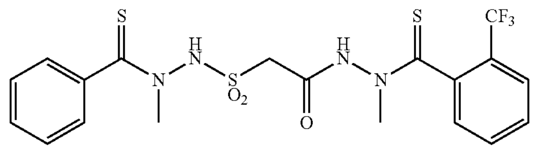 [SMILES: CN(NS(=O)(=O)CC(=O)NN(C)C(=S)c1ccccc1C(F)(F)F)C(=S)c1ccccc1] | N'-methyl-2-(2-methyl-2-(2-(trifluoromethyl)phenylcarbonothioyl)hydrazinyl)-2-oxo-N'-(phenylcarbonothioyl)ethanesulfonohydrazide |
| 82 | 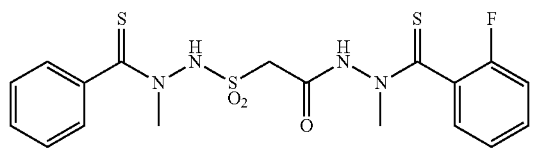 [SMILES: CN(NS(=O)(=O)CC(=O)NN(C)C(=S)c1ccccc1F)C(=S)c1ccccc1] | 2-(2-(2-fluorophenylcarbonothioyl)-2-methylhydrazinyl)-N'-methyl-2-oxo-N'-(phenylcarbonothioyl)ethanesulfonohydrazide |
| 83 | 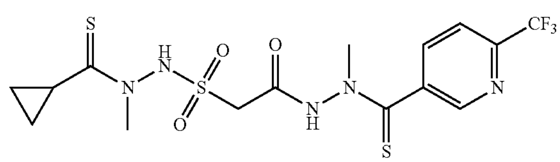 [SMILES: CN(NC(=O)CS(=O)(=O)NN(C)C(=S)C1CC1)C(=S)c1ccc(C(F)(F)F)nc1] | N'-(cyclopropanecarbonothioyl)-N'-methyl-2-(2-methyl-2-(6-(trifluoromethyl)pyridine-3-carbonothioyl)hydrazinyl)-2-oxoethanesulfonohydrazide |
| 84 | 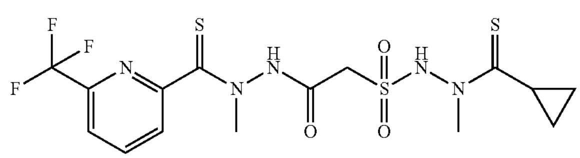 [SMILES: CN(NC(=O)CS(=O)(=O)NN(C)C(=S)C1CC1)C(=S)c1cccc(C(F)(F)F)n1] | N'-(cyclopropanecarbonothioyl)-N'-methyl-2-(2-methyl-2-(6-(trifluoromethyl)pyridine-2-carbonothioyl)hydrazinyl)-2-oxoethanesulfonohydrazide |
| 85 | 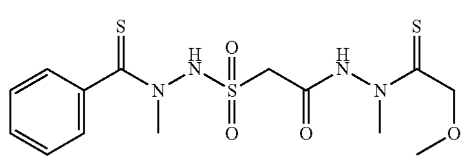 [SMILES: COCC(=S)N(C)NC(=O)CS(=O)(=O)NN(C)C(=S)c1ccccc1] | 2-(2-(2-methoxyethanethioyl)-2-methylhydrazinyl)-N'-methyl-2-oxo-N'-(phenylcarbonothioyl)ethanesulfonohydrazide |
| 86 | 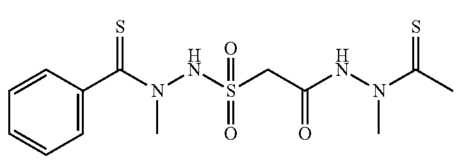 [SMILES: CC(=S)N(C)NC(=O)CS(=O)(=O)NN(C)C(=S)c1ccccc1] | 2-(2-ethanethioyl-2-methylhydrazinyl)-N'-methyl-2-oxo-N'-(phenylcarbonothioyl)ethanesulfonohydrazide |
| 87 | 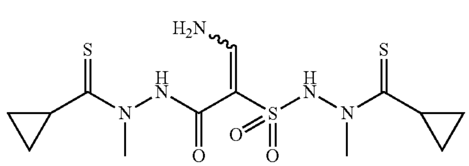 [SMILES: CN(NC(=O)C(=CN)S(=O)(=O)NN(C)C(=S)C1CC1)C(=S)C1CC1] | 1-amino-N'-(cyclopropanecarbonothioyl)-3-(2-(cyclopropanecarbonothioyl)-2-methyl-hydrazinyl)-N'-methyl-3-oxoprop-1-ene-2-sulfonohydrazide |

-continued

| Compound No. | Structure | Chemical Name |
|---|---|---|
| 88 | 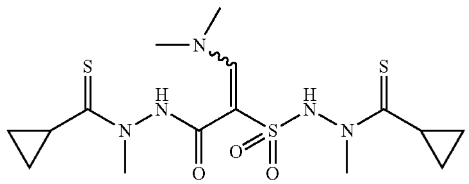 [SMILES: CN(C)C=C(C(=O)NN(C)C(=S)C1CC1)S(=O)(=O)NN(C)C(=S)C1CC1] | N'-(cyclopropanecarbonothioyl)-3-(2-(cyclopropanecarbonothioyl)-2-methylhydrazinyl)-1-(dimethylamino)-N'-methyl-3-oxoprop-1-ene-2-sulfonohydrazide |
| 89 | 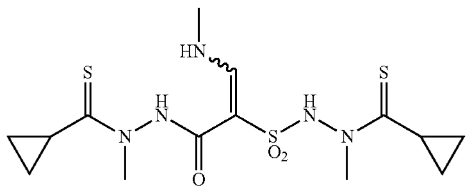 [SMILES: CNC=C(C(=O)NN(C)C(=S)C1CC1)S(=O)(=O)NN(C)C(=S)C1CC1] | N'-(cyclopropanecarbonothioyl)-3-(2-(cyclopropanecarbonothioyl)-2-methylhydrazinyl)-N'-methyl-1-(methylamino)-3-oxoprop-1-ene-2-sulfonohydrazide |
| 90 | 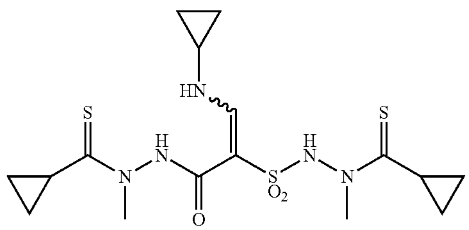 [SMILES: CN(NC(=O)C(=CNC1CC1)S(=O)(=O)NN(C)C(=S)C1CC1)C(=S)C1CC1] | N'-(cyclopropanecarbonothioyl)-3-(2-(cyclopropanecarbonothioyl)-2-methylhydrazinyl)-1-(cyclopropylamino)-N'-methyl-3-oxoprop-1-ene-2-sulfonohydrazide |
| 91 | 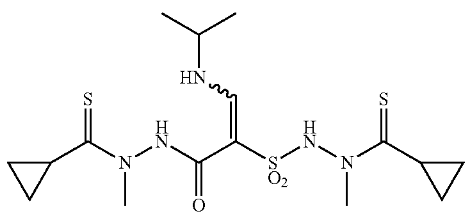 [SMILES: CC(C)NC=C(C(=O)NN(C)C(=S)C1CC1)S(=O)(=O)NN(C)C(=S)C1CC1] | N'-(cyclopropanecarbonothioyl)-3-(2-(cyclopropanecarbonothioyl)-2-methylhydrazinyl)-1-(isopropylamino)-N'-methyl-3-oxoprop-1-ene-2-sulfonohydrazide |

As used herein, the term "alkyl" means a saturated straight chain or branched non-cyclic hydrocarbon having from 1 to 10 carbon atoms. Representative saturated straight chain alkyls include methyl, ethyl, n-propyl, n-butyl, n-pentyl, n-hexyl, n-heptyl, n-octyl, n-nonyl and n-decyl; while saturated branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-dimethylpentyl, 3,3-diethylhexyl, 2,2-diethylhexyl, 3,3-diethylhexyl and the like. The term "($C_1$-$C_n$)alkyl" means a saturated straight chain or branched non-cyclic hydrocarbon having from 1 to n carbon atoms. Representative ($C_1$-$C_6$)alkyl groups are those shown above. A substituted alkyl group can have one or more substituents.

As used herein, the term "alkenyl" means a saturated straight chain or branched non-cyclic hydrocarbon having from 2 to 10 carbon atoms and having at least one carbon-carbon double bond. Representative straight chain and branched ($C_2$-$C_{10}$)alkenyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl and the like. A substituted alkenyl group can have one or more substituent.

As used herein, the term "alkynyl" means a saturated straight chain or branched non-cyclic hydrocarbon having from 2 to 10 carbon atoms and having at lease one carbon-carbon triple bond. Representative straight chain and branched alkynyls include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. A substituted alkynyl group can have one or more substituent.

As used herein, the term "cycloalkyl" means a saturated, mono- or polycyclic alkyl radical having from 3 to 20 carbon atoms. Alternatively, the cycloalkyl is monocyclic (e.g., C3-C8) or bicyclic (e.g., C6-C15). Representative cycloalkyls include cyclopropyl, 1-methylcyclopropyl, cyclobutyl, cyclopentyl, cyclohexyl, cycloheptyl, cyclooctyl, cyclononyl, cyclodecyl, octahydro-pentalenyl, and the like. A substituted cycloalkyl group can have with one or more substituent.

As used herein, the term "cycloalkenyl" means a mono- or poly-cyclic non-aromatic alkyl radical having at least one carbon-carbon double bond in the cyclic system and from 3 to 20 carbon atoms. Alternatively, the cycloalkenyl is monocyclic (e.g., C3-C8) or bicyclic (e.g., C6-C15). Representative cycloalkenyls include cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl, 1,2,3,4,5,8-hexahydronaphthalenyl and the like. A substituted cycloalkenyl group can have one or more substituent.

As used herein, the term "lower" refers to a group having up to four carbon atoms. For example, a "lower alkyl" refers to an alkyl radical having from 1 to 4 carbon atoms, "lower alkoxy" refers to "—O—($C_1$-$C_4$)alkyl and a "lower alkenyl" or "lower alkynyl" refers to an alkenyl or alkynyl radical having from 2 to 4 carbon atoms, respectively.

As used herein, the term "haloalkyl" means and alkyl group in which one or more (including all) of the hydrogen radicals are replaced by a halo group, wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

As used herein, an "alkoxy" is an alkyl group which is attached to another moiety via an oxygen linker.

As used herein, a "haloalkoxy" is a haloalkyl group which is attached to another moiety via an oxygen linker.

As used herein, the term "aryl", "aryl ring", "aryl group", "aromatic group" or "aromatic ring" means a monocyclic or polycyclic hydrocarbon radical in which at least one ring is aromatic. Examples of suitable aryl groups include, but are not limited to, phenyl, anthracenyl, fluorenyl, indenyl, azulenyl, and naphthyl, as well as benzo-fused carbocyclic moieties such as 5,6,7,8-tetrahydronaphthyl. A substituted aryl groups can have one or more substituents. In one embodiment, the aryl group is a monocyclic ring, wherein the ring comprises 6 carbon atoms, referred to herein as "($C_6$)aryl" or "phenyl". A bicyclic aryl group includes naphthyl, as well as benzo-fused carbocyclic moieties such as 5,6,7,8-tetrahydronaphthyl.

As used herein, the term "alkylene" refers to an alkyl group that has two points of attachment. The term "($C_1$-$C_6$)alkylene" refers to an alkylene group that has from one to six carbon atoms. Straight chain ($C_1$-$C_6$)alkylene groups are preferred. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like. A substituted alkylene groups can have one or more substituents.

As used herein, the term "heterocyclyl" means a monocyclic (typically having 3- to 10-members and more typically 3 to 7-members), bicyclic (typically 6 to 14 members) or a polycyclic (typically having 7- to 20-members) heterocyclic ring system which is either a saturated ring or an unsaturated, non-aromatic ring. A 3- to 10-membered heterocycle can contain up to 5 heteroatoms; and a 7- to 20-membered heterocycle can contain up to 7 heteroatoms. Typically, a heterocycle has at least one carbon atom ring member. Each heteroatom is independently selected from nitrogen, which can be oxidized (e.g., N(O)) or quaternized; oxygen; and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, the hydrogen on a nitrogen may be substituted with a tert-butoxycarbonyl group. Furthermore, a substituted heterocyclyl can have one or more substituents. Only stable isomers of such substituted heterocyclic groups are contemplated in this definition.

As used herein, the term "heteroaromatic", "heteroaryl" or like terms means a monocyclic, bicyclic or polycyclic heteroaromatic ring comprising carbon atom ring members and one or more heteroatom ring members. Each heteroatom is independently selected from nitrogen, which can be oxidized (e.g., N(O)) or quaternized; oxygen; and sulfur, including sulfoxide and sulfone. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, a isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl. In one embodiment, the heteroaromatic ring is selected from 5-8 membered monocyclic heteroaryl rings; and the bicyclic heteroaromatic ring is a 8-12 membered, more commonly 8-10 membered. The point of attachment of a heteroaromatic or heteroaryl ring to another group may be at either a carbon atom or a heteroatom of the heteroaromatic or heteroaryl rings. A substituted heteroaryl group can have one or more substituents.

As used herein, the term "5-membered heteroaryl" means an aromatic ring of 5 members, wherein at least one atom in the ring is a heteroatom such as, for example, oxygen, sulfur or nitrogen. Representative ($C_5$)heteroaryls include furanyl, thienyl, pyrrolyl, oxazolyl, imidazolyl, thiazolyl, isoxazolyl, pyrazolyl, isothiazolyl, pyrazinyl, triazolyl, thiadiazolyl, and the like.

As used herein, the term "6-heteroaryl" means an aromatic ring of 6 members, wherein at least one atom in the ring is a heteroatom such as, for example, oxygen, nitrogen or sulfur. Representative ($C_6$)heteroaryls include pyridyl, pyridazinyl, pyrazinyl, triazinyl, tetrazinyl and the like.

As used herein, the term "halogen" or "halo" means —F, —Cl, —Br or —I.

Suitable substituents for an alkyl, alkylene, alkenyl, alkynyl, cycloalkyl, cycloalkenyl, heterocyclyl, aryl and heteroaryl groups include —OH, —Br, —Cl, —I, —F, —$R^a$, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—$N(R^aR^b)$, —$NR^d$—C(=NH)—$NH_2$, —$NR^d$—C(=NH)—$NHR^a$, —$NR^d$—C(=NH)—$N(R^aR^b)$, —$NR^d$—C(=$NR^c$)—$NH_2$, —$NR^d$—C(=$NR^c$)—$NHR^a$, —$NR^d$—C(=$NR^c$)—$N(R^aR^b)$, —NHNH₂, —NHNHR$^a$, —NHN(R$^a$R$^b$), —SO₂NH₂, —SO₂NHR$^a$, —SO₂NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)₂R$^a$, heterocyclic group, benzyl group and aryl group wherein R$^a$-R$^d$ are each independently a lower alkyl, a lower haloalkyl, a lower alkoxy, a lower hydroxyalkyl, benzyl, aryl, or, —NR$^a$R$^d$, taken together, can also form a heterocyclic group. In addition, alkyl, cycloalkyl, alkylene, a heterocyclyl, and any saturated portion of a alkenyl, cycloalkenyl, alkynyl, aralkyl, and heteroarylkyl groups, may also be substituted with =O, =S, =N—R$^a$.

An alternative list of substituents for an alkyl, alkylene, alkenyl, alkynyl, cycloalkyl, cycloalkenyl, heterocyclyl and aryl and heteroaryl groups include alkyl, alkoxy, haloalkyl, haloalkoxy, cyano and nitro.

When a heterocyclyl or heteroaryl group contains a nitrogen atom, it may be substituted or unsubstituted. When a nitrogen atom in the aromatic ring of a heteroaryl group has a substituent (e.g., represented by R$^a$) the nitrogen may be a quaternary nitrogen.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

As used herein, the term "compound(s) of this invention" and similar terms refers to compounds represented by Structural Formula (I) and compounds encompassed within Structural Formulas (I).

Pharmaceutically acceptable salts of the compounds of the invention are included in the present invention. For example, an acid salt of a compound of the invention containing an amine or other basic group can be obtained by reacting the compound with a suitable organic or inorganic acid, resulting in pharmaceutically acceptable anionic salt forms. Examples of anionic salts include the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, and triethiodide salts.

Salts of the compounds of the invention containing an acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids such as lysine and arginine.

Certain compounds of the invention may be obtained as different isomers (e.g., stereoisomers, coordination isomers, linkage isomers, hydrate isomers, and the like). The invention includes isomeric forms of the disclosed compounds and both pure isomers and mixtures thereof, including racemic mixtures. Isomers can be separated and isolated using any suitable method, such as chromatography.

The compounds of the invention are advantageously in substantially pure form, e.g., greater than 50%, 60%, 70%, 80%, 90%, 95%, 97%, 99%, 99.5% or 99.9% pure by weight. "Percent purity by weight" means the weight of the compound divided by the weight of the compound plus impurities times 100%.

The compounds of the invention may contain one or more chiral centers and/or double bonds and, therefore, exist as stereoisomers, such as double-bond isomers (i.e., geometric isomers), enantiomers, or diastereomers. According to this invention, the chemical structures depicted herein, including the compounds of this invention, encompass all of the corresponding compounds' enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds of this invention are preferred.

As used herein, "complexed" means that the compound of the invention or a deprotonated form thereof attaches to a transition metal ion through one or more coordinate covalent bonds or coordination bonds.

As used herein, "chelated" means that the compound of the invention or a deprotonated form thereof binds to a transition metal ion at two or more attachment points through coordinate covalent bonds or coordination bonds.

As used herein, "coordinate", "coordinated", "coordinate covalent bond" and "coordination bond" have the meanings that are commonly known to one of ordinary skill in the art.

As used herein, a "deprotonated form" of the compound of the invention refers to a molecule wherein one or more protons are removed from the compound. For example, a deprotonated form of the compound represented by Structural Formula (I) is shown below:

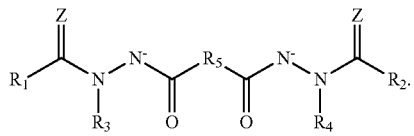

A "transition metal cation" refers to a positively charged ion of a metal in Groups 3-12 of the Periodic Table. Examples include Ni$^{2+}$, Cu$^+$, Cu$^{2+}$, Co$^{2+}$, Co$^{3+}$, Fe$^{2+}$, Fe$^{3+}$, Zn$^{2+}$, Pt$^{2+}$, Pd$^{2+}$, V$^{4+}$, V$^{5+}$, Cr$^{2+}$, Cr$^{3+}$, Cr$^{4+}$, Mn$^{2+}$, Mn$^{3+}$, Mn$^{4+}$ and Mn$^{5+}$. In a specific embodiment, the transition metal cation has a +1 charge. In a specific embodiment, the transition metal cation has a +2 charge. Examples include Ni$^{2+}$, Cu$^{2+}$, Co$^{2+}$, Fe$^{2+}$, Zn$^{2+}$, Pt$^{2+}$ and Pd$^{2+}$. In a specific embodiment, the transition metal cation is Cu$^{2+}$ or Ni$^{2+}$. The molar ratio of the compound of the invention or a deprotonated form thereof to transition metal cation recited in this paragraph is, for example, equal to or greater than 0.5 and equal to or less than 2.0 (i.e. 0.5≤ratio≤2.0) or 1:1.

As used herein, "Hsp70" includes each member of the family of heat shock proteins having a mass of about 70-kiloDaltons, including forms such as constitutive, cognate, cell-specific, glucose-regulated, inducible, etc. Examples of specific Hsp70 proteins include hsp70, hsp70hom; hsc70; Grp78/BiP; mt-hsp70/Grp75, and the like). Typically, the disclosed methods increase expression of inducible Hsp70. Functionally, the 70-kDa HSP (HSP70) family is a group of chaperones that assist in the folding, transport, and assembly of proteins in the cytoplasm, mitochondria, and endoplasmic reticulum. In humans, the Hsp70 family encompasses at least 11 genes encoding a group of highly related proteins. See, for example, Tavaria, et al., *Cell Stress Chaperones,* 1996, 1(1): 23-28; Todryk, et al., *Immunology,* 2003, 110(1): 1-9; and Georgopoulos & Welch, *Annu. Rev. Cell Biol.*, 1993, 9:601-634; the entire teachings of these documents are incorporated herein by reference.

As used herein, an "Hsp70-responsive disorder" is a medical condition wherein stressed cells can be treated by increased Hsp70 expression. Such disorders can be caused by a wide variety of cellular stressors, including, but not limited to Alzheimer's disease; Huntington's disease; Parkinson's disease; spinal/bulbar muscular atrophy (e.g., Kennedy's disease), spinocerebellar ataxic disorders, and other neuromuscular atrophies; familial amyotrophic lateral sclerosis; ischemia; seizure; hypothermia; hyperthermia; burn trauma; atherosclerosis; radiation exposure; glaucoma; toxin exposure; mechanical injury; inflammation; autoimmune disease; infection (bacterial, viral, fungal, or parasitic); and the like.

In some embodiments, the Hsp70-responsive disorder is a neurodegenerative disorder. As used herein, a neurodegenerative disorder involves degradation of neurons such as cerebral, spinal, and peripheral neurons (e.g., at neuromuscular junctions), more typically degradation of cerebral and spinal neurons, or in preferred embodiments, degradation of cerebral neurons. Neurodegenerative disorders can include Alzheimer's disease; Huntington's disease; Parkinson's disease; spinal/bulbar muscular atrophy and other neuromuscular atrophies; and familial amyotrophic lateral sclerosis or other diseases associated with superoxide dismutase (SOD) mutations. Neurodegenerative disorders can also include degradation of neurons caused by ischemia, seizure, thermal stress, radiation, toxin exposure, infection, injury, and the like.

In some embodiments, the Hsp70-responsive disorder is a disorder of protein aggregation/misfolding, such as Alzheimer's disease; Huntington's disease; Parkinson's disease; spongiform encephalopathies; and the like.

In another embodiment the Hsp70 responsive disorder is a treatment or condition which causes or may cause nerve damage. The compounds for use in the methods of the present invention can be used to reduce or prevent (inhibit the onset of) nerve damage (i.e., provide neuroprotection) in a subject i) suffering from a condition which causes or may cause nerve damage or ii) receiving treatment which causes or may cause nerve damage. In one aspect, the treatment which causes or may cause nerve damage is radiation therapy. In another aspect, the treatment is chemotherapy. In one aspect, the chemotherapy comprises administering an antimitotic agent (e.g. vincristine, vinorelbine, paclitaxel, or a paclitaxel analog). In one aspect, the chemotherapy comprises administering paclitaxel. In another aspect, the chemotherapy comprises administering a platinum derivative (e.g. cisplatinum, carboplatin, or oxaliplatin). In certain embodiments, the compounds for use in the methods of the present invention can be administered simultaneously as a combination therapy with the treatment which causes or may cause nerve damage. In other embodiments the compounds for use in the methods of the present invention can be administered before or after the treatment which causes may cause nerve damage. In certain embodiments the compounds for use in the methods of the present invention can be administered between 30 minutes and 12 hours, between 1 hour and 6 before or after the treatment which causes or may cause nerve damage.

Nerve damage may be caused by a number of treatments including, but not limited to, radiation therapy; chemotherapy, e.g. cisplatinum, carboplatin, oxaliplatin, vincristine, vinblastine, vinorelbine, vindesine, ifosfamide, methotrexate, cladribine, altretamine, fludarabine, procarbazine, thiotepa, teniposide, arsenic trioxide, alemtuzumab, capecitabine, dacarbazine, denileukin diftitox, interferon alpha, liposomal daunorubicin, tretinoin, etoposide/VP-16, cytarabine, hexamethylmelamine, suramin, paclitaxel, docetaxel, gemcitabine, thalidomide, and bortezomib; heart or blood pressure medications, e.g. amiodarone, hydralazine, digoxin, and perhexiline; medications to fight infection, e.g. metronidazole, nitrofurantoin, thalidomide, and INH; medications to treat skin conditions, e.g. dapsone; anticonvulsants, e.g. phenyloin; anti-alcohol medications, e.g. disulfiram; HIV medications, e.g. zidovudine, didanosine, stavudine, zalcitabine, ritonavir, d4T, ddC, ddI, and amprenavir; cholesterol medications, e.g. lovastatin, pravastatin, indapamide, simvastatin, fluvastatin, atorvastatin, cerivastatin, and gemfibrozil; anti-rheumatics, e.g. chloroquine, colchicine, organic gold, and penicillamine; nitrous oxide; lithium; and ergots.

In some embodiments, the Hsp70-responsive disorder is ischemia. Ischemia can damage tissue through multiple routes, including oxygen depletion, glucose depletion, oxidative stress upon reperfusion, and/or glutamate toxicity, and the like. Ischemia can result from an endogenous condition (e.g., stroke, heart attack, and the like), from accidental mechanical injury, from surgical injury (e.g., reperfusion stress on transplanted organs), and the like. Alternatively, tissues that can be damaged by ischemia include neurons, cardiac muscle, liver tissue, skeletal muscle, kidney tissue, pulmonary tissue, pancreatic tissue, and the like. In one preferred embodiment, the Hsp70-responsive disorder is cerebral or spinal ischemia. In another preferred embodiment, the Hsp70-responsive disorder is cardiac ischemia.

In various embodiments, the Hsp70-responsive disorder is seizure, e.g., epileptic seizure, injury-induced seizure, chemically-induced seizure, and the like.

In some embodiments, the Hsp70-responsive disorder is due to thermal stress. Thermal stress includes hyperthermia (e.g., from fever, heat stroke, burns, and the like) and hypothermia. In a preferred embodiment the disorder is hyperthermia. In another preferred embodiment, the Hsp70-responsive disorder is burn trauma.

In preferred embodiments, the Hsp70-responsive disorder is atherosclerosis.

In various embodiments, the Hsp70-responsive disorder is radiation damage, e.g., due to visible light, ultraviolet light, microwaves, cosmic rays, alpha radiation, beta radiation, gamma radiation, X-rays, and the like. For example, the damage could be radiation damage to non-cancerous tissue in a subject treated for cancer by radiation therapy. In a preferred embodiment, the Hsp70-responsive disorder is radiation damage from visible light or ultraviolet light.

In various embodiments, the Hsp70-responsive disorder is mechanical injury, e.g., trauma from surgery, accidents, certain disease conditions (e.g., pressure damage in glaucoma)

and the like. In a preferred embodiment, the Hsp70-responsive disorder is cerebral or spinal trauma. In another preferred embodiment, the Hsp70-responsive disorder is glaucoma (leading to pressure damage to retinal ganglions).

In various embodiments, the Hsp70-responsive disorder is exposure to a toxin. In preferred embodiments, the Hsp70-responsive disorder is exposure to a neurotoxin selected from methamphetamine; antiretroviral HIV therapeutics (e.g., nucleoside reverse transcriptase inhibitors; heavy metals (e.g., mercury, lead, arsenic, cadmium, compounds thereof, and the like), amino acid analogs, chemical oxidants, ethanol, glutamate, metabolic inhibitors, antibiotics, and the like.

Another embodiment of the present invention is a method of treating a subject with a cancer. Optionally, the method of the invention can be used for a multi-drug resistant cancer as described below. The method comprises the step of administering an effective amount of a compound of the invention. Preferably, one or more additional anti-cancer drugs are co-administered with a compound of the invention. Examples of anti-cancer drugs are described below. Preferably, the co-administered anti-cancer drug is an agent that stabilizes microtubules, such as paclitaxel or a taxane derivative.

"Treating a subject with a cancer" includes achieving, partially or substantially, one or more of the following: arresting the growth or spread of a cancer, reducing the extent of a cancer (e.g., reducing size of a tumor or reducing the number of affected sites), inhibiting the growth rate of a cancer, and ameliorating or improving a clinical symptom or indicator associated with a cancer (such as tissue or serum components), and/or reducing the likelihood of the cancer recurring once it has gone into remission.

The compounds of the invention are suitable for monotherapies, as well as in combination or in co-therapies with other anti-proliferative or anticancer therapies, such as paclitaxel.

Other anti-proliferative or anticancer therapies may be combined with the compounds of this invention to treat proliferative diseases and cancer. Other therapies or anticancer agents that may be used in combination with the inventive anticancer agents of the present invention include surgery, radiotherapy (including, but not limited to, gamma-radiation, neutron beam radiotherapy, electron beam radiotherapy, proton therapy, brachytherapy, and systemic radioactive isotopes), endocrine therapy, biologic response modifiers (including, but not limited to, interferons, interleukins, and tumor necrosis factor (TNF)), hyperthermia and cryotherapy, agents to attenuate any adverse effects (e.g., antiemetics), and other approved chemotherapeutic drugs. The prophylactic or therapeutic agents of the combination therapies of the invention can be administered sequentially or concurrently.

As used herein, the terms "hyperthermia", "hyperthermia therapy," "thermal therapy," and "thermotherapy" are used interchangeably to mean a treatment where body tissue is exposed to high temperatures (up to 113° F.). The term as used herein includes all forms of hyperthermia, including local, regional, and whole-body. Various forms of energy can be used to deliver heat to the desired area, such as microwave, radiofrequency, lasers, and ultrasound. The treatment temperatures vary depending on the location of the tumor and the approach used.

In local hyperthermia, heat is applied to a small area (e.g. a tumor). The approaches to local hyperthermia vary with tumor location. External approaches are used to treat tumors in or just below the skin. In this method, applicators are place near or around the tumor and deliver energy directly to the tumor. Intraluminal or endocavitary approaches use probes to deliver energy to tumors within or near body cavities. Interstitial approaches are used to treat tumors deep within the body (e.g. brain tumors), by inserting probes or needles into the tumor under anesthesia.

In regional hyperthermia, heat is applied to large areas of tissue (e.g. body cavity, organ, or limb). Deep tissue approaches are used to treat cancers within the body (e.g. cervical or bladder cancer) by using external applicators. Regional perfusion approaches are used to treat cancers in the limbs or organs (e.g. melanoma, liver, or lung cancer). In this approach some of the blood is removed and heated and then pumped back into the limb or organ. Anticancer drugs may be given during this process. Continuous hypothermic peritoneal perfusion (CHPP) is used to treat cancers in the peritoneal cavity (e.g. peritoneal mesothelioma or stomach cancer). In this approach, heated anticancer drugs are pumped through the peritoneal cavity.

Whole-body hyperthermia is used to treat metastatic cancer. In this approach, the whole body is heated to 107-108° F. by using various techniques such as thermal chambers or hot water blankets.

Hypothermic conditions are known to induce the synthesis of Hsp70.

In another embodiment, a compound of the invention can be administered as adjuvant therapy to prevent or reduce the likelihood of reoccurrence of cancer. For example, stage II and stage III melanoma are typically treated with surgery to remove the melanoma followed by chemotherapeutic treatment to prevent the reoccurrence of cancer. In one embodiment, one or more additional anti-cancer drugs are co-administered with a compound of the invention as adjuvant therapy. Examples of anti-cancer drugs are described below. In one embodiment, the co-administered anti-cancer drug is an agent that stabilizes microtubules, such as paclitaxel or a taxane derivative. In another embodiment, the co-administered anti-cancer drug is an immunotherapeutic anticancer agent.

Cancers that can be treated or prevented by the methods of the present invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, anal carcinoma, esophageal cancer, gastric cancer, hepatocellular cancer, bladder cancer, endometrial cancer, pancreatic cancer, breast cancer, ovarian cancer, prostate cancer, stomach cancer, atrial myxomas, squamous cell carcinoma, basal cell carcinoma, adenocarcinoma, sweat gland carcinoma, sebaceous gland carcinoma, thyroid and parathyroid neoplasms, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, non-small-cell lung cancer, bladder carcinoma, epithelial carcinoma, glioma, pituitary neoplasms, astrocytoma, medulloblastoma, craniopharyngioma, ependymoma, pinealoma, hemangioblastoma, acoustic neuroma, schwannomas, oligodendroglioma, meningioma, spinal cord tumors, melanoma, neuroblastoma, pheochromocytoma, Types 1-3 endocrine neoplasia, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrobm's macroglobulinemia, and heavy chain disease.

Other examples of leukemias include acute and/or chronic leukemias, e.g., lymphocytic leukemia (e.g., as exemplified by the p388 (murine) cell line), large granular lymphocytic leukemia, and lymphoblastic leukemia; T-cell leukemias, e.g., T-cell leukemia (e.g., as exemplified by the CEM, Jurkat, and HSB-2 (acute), YAC-1 (murine) cell lines), T-lymphocytic leukemia, and T-lymphoblastic leukemia; B cell leukemia (e.g., as exemplified by the SB (acute) cell line), and B-lymphocytic leukemia; mixed cell leukemias, e.g., B and T cell leukemia and B and T lymphocytic leukemia; myeloid leukemias, e.g., granulocytic leukemia, myelocytic leukemia (e.g., as exemplified by the HL-60 (promyelocyte) cell line), and myelogenous leukemia (e.g., as exemplified by the K562 (chronic)cell line); neutrophilic leukemia; eosinophilic leukemia; monocytic leukemia (e.g., as exemplified by the THP-1 (acute) cell line); myelomonocytic leukemia; Naegeli-type myeloid leukemia; and nonlymphocytic leukemia. Other examples of leukemias are described in Chapter 60 of *The Chemotherapy Sourcebook*, Michael C. Perry Ed., Williams & Williams (1992) and Section 36 of *Holland Frie Cancer Medicine* 5th Ed., Bast et al. Eds., B. C. Decker Inc. (2000). The entire teachings of the preceding references are incorporated herein by reference.

Additional cancers that can be treated or prevented by the methods of the present invention include, but are not limited to oral cavity and pharynx cancers, including tongue, mouth, pharynx, and other oral cavity cancers; digestive system cancers, including esophagus, small intestine, rectum, anus, anal canal, anorectic, liver and intrahepatic bile duct, gallbladder and other biliary, pancreas and other digestive organs; respiratory system cancers, including larynx and bronchus; bone and joint cancers; soft tissue (including heart) cancers; genital system cancers, including uterine cervix, uterine corpus, ovary, vulva, vagina and other female genital, testis, penis and other male genital; urinary system cancers, including kidney and renal pelvis, and ureter and other urinary organs; eye and orbit cancers; leukemia, including acute myeloid leukemia and chronic myeloid leukemia.

In one embodiment, the disclosed method is believed to be effective in treating a subject with non-solid tumors such as multiple myeloma. In another embodiment, the disclosed method is believed to be effective against T-leukemia (e.g., as exemplified by Jurkat and CEM cell lines); B-leukemia (e.g., as exemplified by the SB cell line); promyelocytes (e.g., as exemplified by the HL-60 cell line); uterine sarcoma (e.g., as exemplified by the MES-SA cell line); monocytic leukemia (e.g., as exemplified by the THP-1 (acute) cell line); and lymphoma (e.g., as exemplified by the U937 cell line).

In another embodiment, the disclosed method is believed to be effective in treating a subject with an immunosensitive cancer. Immunosensitive cancers are cancers that respond to treatment with immunotherapy. Immunotherapy is described below in more detail. Cancers that respond to immunotherapy include renal cell carcinoma, melanoma (including superficial spreading melanoma, nodular melanoma, accrual lentiginous melanoma, lentigo maligna melanoma which is also called Hutchinson's Freckle), multiple myeloma, myeloma, lymphoma, non-small-cell lung cancer, squamous cell carcinoma, basal cell carcinoma, fibrosarcoma and malignant brain tumors.

In another embodiment, the disclosed method is believed to be effective in treating a subject with melanoma.

In another embodiment, the disclosed method is believed to be effective in treating a subject with renal cell carcinoma.

The disclosed method is effective at treating subjects whose cancer has become "drug resistant". A cancer which initially responded to an anti-cancer drug becomes resistant to the anti-cancer drug when the anti-cancer drug is no longer effective in treating the subject with the cancer. For example, many tumors will initially respond to treatment with an anti-cancer drug by decreasing in size or even going into remission, only to develop resistance to the drug. Drug resistant tumors are characterized by a resumption of their growth and/or reappearance after having seemingly gone into remission, despite the administration of increased dosages of the anti-cancer drug. Cancers that have developed resistance to two or more anti-cancer drugs are said to be "multi-drug resistant". For example, it is common for cancers to become resistant to three or more anti-cancer agents, often five or more anti-cancer agents and at times ten or more anti-cancer agents.

Numerous non-cancer diseases involve excessive or hyperproliferative cell growth, termed hyperplasia. As used herein, the terms "proliferative disorder", "hyperproliferative disorder," and "cell proliferation disorder" are used interchangeably to mean a disease or medical condition involving pathological growth of cells. Such disorders include cancer.

Non-cancerous proliferative disorders include smooth muscle cell proliferation, systemic sclerosis, cirrhosis of the liver, adult respiratory distress syndrome, idiopathic cardiomyopathy, lupus erythematosus, retinopathy, e.g., diabetic retinopathy or other retinopathies, cardiac hyperplasia, reproductive system associated disorders such as benign prostatic hyperplasia and ovarian cysts, pulmonary fibrosis, endometriosis, fibromatosis, harmatomas, lymphangiomatosis, sarcoidosis, desmoid tumors and the like.

Smooth muscle cell proliferation includes proliferative vascular disorders, for example, intimal smooth muscle cell hyperplasia, restenosis and vascular occlusion, particularly stenosis following biologically- or mechanically-mediated vascular injury, e.g., vascular injury associated with balloon angioplasty or vascular stenosis. Moreover, intimal smooth muscle cell hyperplasia can include hyperplasia in smooth muscle other than the vasculature, e.g., hyperplasia in bile duct blockage, in bronchial airways of the lung in asthma patients, in the kidneys of patients with renal interstitial fibrosis, and the like.

Non-cancerous proliferative disorders also include hyperproliferation of cells in the skin such as psoriasis and its varied clinical forms, Reiter's syndrome, pityriasis rubra pilaris, and hyperproliferative variants of disorders of keratinization (e.g., actinic keratosis, senile keratosis), scleroderma, and the like.

An "effective amount" is the quantity of compound in which a beneficial clinical outcome is achieved when the compound is administered to a subject. For example, when a compound of the invention is administered to a subject with a cancer, a "beneficial clinical outcome" includes a reduction in tumor mass, a reduction in metastasis, a reduction in the severity of the symptoms associated with the cancer and/or an increase in the longevity of the subject compared with the absence of the treatment. When a compound of the invention is administered to a subject with a Hsp70-responsive disorder, a "beneficial clinical outcome" includes reduction in the severity or number of symptoms associated with the disorder, elimination of an infection, or increase in the longevity of the subject compared with the absence of the treatment.

The precise amount of compound administered to a subject will depend on the type and severity of the disease or condition and on the characteristics of the subject, such as general health, age, sex, body weight and tolerance to drugs. It may also depend on the degree, severity and type of cancer. The skilled artisan will be able to determine appropriate dosages depending on these and other factors. Effective amounts of the disclosed compounds typically range between about 1 mg/mm$^2$ per day and about 10 grams/mm$^2$ per day, and preferably between 10 mg/mm$^2$ per day and about 5 grams/mm$^2$. In some embodiments, effective amounts of the disclosed compounds include microgram to milligram amounts of the compound per kilogram of subject or sample weight (e.g., about 1 µg/kg to about 500 mg/kg, about 500 µg/kg to about 250 mg/kg, about 1 mg/kg to about 100 mg/kg, about 10 mg/kg to about 50 mg/kg, and the like). When co-administered with another anti-cancer agent for the treatment of cancer, an "effective amount" of the second anti-cancer agent will depend on the type of drug used. Suitable dosages are known for approved anti-cancer agents and can be adjusted by the skilled artisan according to the condition of the subject, the type of cancer being treated and the compound of the invention being used.

Another embodiment of the present invention is a pharmaceutical composition comprising a compound of the invention and a pharmaceutically acceptable carrier or diluent.

Suitable pharmaceutically acceptable carriers may contain inert ingredients which do not inhibit the biological activity of the disclosed compounds of the invention. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed, such as those described in REMINGTON'S PHARMACEUTICAL SCIENCES (Mack Publishing Company, Easton, Pa.). Formulation of the compound to be administered will vary according to the route of administration selected (e.g., solution, emulsion, capsule). Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextrins) are known in the art. BAKER, et al., CONTROLLED RELEASE OF BIOLOGICAL ACTIVE AGENTS (John Wiley and Sons, (1986)).

The compounds of the invention are administered by any suitable route, including, for example, orally in capsules, suspensions or tablets or by parenteral administration. Parenteral administration can include, for example, systemic administration, such as by intramuscular, intravenous, subcutaneous, or intraperitoneal injection. The compounds of the invention can also be administered orally (e.g., dietary), topically, by inhalation (e.g., intrabronchial, intranasal, oral inhalation or intranasal drops), or rectally, depending on the type of cancer to be treated. Oral and parenteral administrations are preferred modes of administration.

Many new drugs are now available to be used by oncologists in treating patients with cancer. Often, tumors are more responsive to treatment when anti-cancer drugs are administered in combination to the patient than when the same drugs are administered individually and sequentially. One advantage of this approach is that the anti-cancer agents often act synergistically because the tumors cells are attacked simultaneously with agents having multiple modes of action. Thus, it is often possible to achieve more rapid reductions in tumor size by administering these drugs in combination. Another advantage of combination chemotherapy is that tumors are more likely to be eradicated completely and are less likely to develop resistance to the anti-cancer drugs being used to treat the patient.

Optionally, a compound of the invention can be co-administered to treat a patient with a proliferative disorder such as cancer, or to prevent (reduce the likelihood) the reoccurrence of a proliferative disorder such as cancer, with other anti-cancer agents such as Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

Other drugs that can be used in combination with the compounds of the invention to treat a patient with a proliferative disorder such as cancer, or to prevent (reduce the likelihood) the reoccurrence of a proliferative disorder such as cancer, include, but are not limited to: 20-epi-1,25 dihydroxyvitamin D3; 5-ethynyluracil; abiraterone; acylfulvene; adecypenol;

ALL-TK antagonists; ambamustine; amidox; amifostine; aminolevulinic acid; amrubicin; anagrelide; andrographolide; angiogenesis inhibitors; antagonist D; antagonist G; antarelix; anti-dorsalizing morphogenetic protein-1; antiandrogen; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; assertion; azatoxin; azatyrosine; baccatin III derivatives; balanol; BCR/ABL antagonists; benzochlorins; benzoylstaurosporine; beta lactam derivatives; beta-aletheine; betaclamycin B; betulinic acid; bFGF inhibitor; bisantrene; bisaziridinylspermine; bisnafide; bistratene A; breflate; budotitane; buthionine sulfoximine; calcipotriol; calphostin C; camptothecin derivatives; canarypox IL-2; capecitabine; carboxamide-aminotriazole; carboxyamidotriazole; CaRest M3; CARN 700; cartilage derived inhibitor; casein kinase inhibitors (ICOS); castanospermine; cecropin B; cetrorelix; chlorins; chloroquinoxaline sulfonamide; cicaprost; cis-porphyrin; clomifene analogs; clotrimazole; collismycin A; collismycin B; combretastatin A4; combretastatin analog; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; dehydrodidemnin B; deslorelin; dexamethasone; dexifosfamide; dexrazoxane; dexverapamil; didemnin B; didox; diethylnorspermine; dihydro-5-azacytidine; 9-dioxamycin; diphenyl spiromustine; docosanol; dolasetron; doxifluridine; dronabinol; duocarmycin SA; ebselen; ecomustine; edelfosine; edrecolomab; eflornithine; elemene; emitefur; epirubicin; episteride; estramustine analog; estrogen agonists; estrogen antagonists; exemestane; fadrozole; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; glutathione inhibitors; hepsulfam; heregulin; hexamethylene bisacetamide; hypericin; ibandronic acid; idarubicin; idoxifene; idramantone; ilomastat; imidazoacridones; imiquimod; immunostimulant peptides; insulin-like growth factor-1 receptor inhibitor; interferon agonists; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; leukemia inhibiting factor; leukocyte alpha interferon; leuprolide+estrogen+progesterone; leuprorelin; levamisole; liarozole; linear polyamine analog; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lisofylline; lytic peptides; maitansine; mannostatin A; marimastat; maspin; matrilysin inhibitors; matrix metalloproteinase inhibitors; membrane; meterelin; methioninase; metoclopramide; MIF inhibitor; mifepristone; miltefosine; mirimostim; mismatched double stranded RNA; mitoguazone; mitolactol; mitomycin analogs; mitonafide; mitotoxin fibroblast growth factor-saporin; mitoxantrone; mofarotene; molgramostim; monoclonal antibody, human chorionic gonadotrophin; monophosphoryl lipid A+mycobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; osaterone; oxaliplatin; oxaunomycin; palauamine; palmitoylrhizoxin; pamidronic acid; panaxytriol; panomifene; parabactin; pazelliptine; peldesine; pentosan polysulfate sodium; pentostatin; pentrozole; perflubron; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; saintopin; SarCNU; sarcophytol A; sargramostim; Sdi 1 mimetics; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tellurapyrylium; telomerase inhibitors; temozolomide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; titanocene bichloride; topsentine; toremifene; totipotent stem cell factor; translation inhibitors; tretinoin; triacetyluridine; triciribine; tropisetron; turosteride; tyrosine kinase inhibitors; tyrphostins; UBC inhibitors; ubenimex; urogenital sinus-derived growth inhibitory factor; urokinase receptor antagonists; variolin B; vector system, erythrocyte gene therapy; velaresol; veramine; verdins; vinorelbine; vinxaltine; vitaxin; zanoterone; zilascorb; and zinostatin stimalamer. Preferred additional anti-cancer drugs are 5-fluorouracil and leucovorin.

Examples of therapeutic antibodies that can be used in combination with the compounds of the invention to treat a proliferative disorder such as cancer, or to prevent (reduce the likelihood) the reoccurrence of a proliferative disorder such as cancer, include but are not limited to HERCEPTIN® (Trastuzumab) (Genentech, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone Systems); IMC-C225 which is a chimeric anti-EGFR IgG antibody (ImClone System); VITAXINT™ which is a humanized anti-αVβ3 integrin antibody (Applied Molecular Evolution/MedImmune); Campath 1H/LDP-03 which is a humanized anti CD52 IgG1 antibody (LeukoSite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); LYMPHOCIDE™ Y-90 (Immunomedics); Lymphoscan (Tc-99m-labeled; radioimaging; Immunomedics); Nuvion (against CD3; Protein Design Labs); CM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharma); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG1 antibody (Medarex/Eisai/Genmab); CD20-sreptdavidin (+biotin-yttrium 90; NeoRx); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-β2 antibody (Cambridge Ab Tech).

Chemotherapeutic agents that can be used in combination with the compounds of the invention to treat a patient with a proliferative disorder such as cancer, or to prevent (reduce the likelihood) the reoccurrence of a proliferative disorder such as cancer, include but are not limited to alkylating agents, antimetabolites, natural products, or hormones. Examples of alkylating agents useful for the treatment or prevention (reduction in the likelihood of developing or the likelihood of reoccurrence of) T-cell malignancies in the methods and compositions of the invention include but are not limited to, nitrogen mustards (e.g., mechlorethamine, cyclophosphamide, chlorambucil, etc.), alkyl sulfonates (e.g., busulfan), nitrosoureas (e.g., carmustine, lomustine, etc.), or triazenes (decarbazine, etc.). Examples of antimetabolites useful for the treatment or prevention (reduction in the likelihood of developing or the likelihood of reoccurrence of) of T-cell malignancies in the methods and compositions of the invention include but are not limited to folic acid analog (e.g., methotrexate), or pyrimidine analogs (e.g., Cytarabine), purine analogs (e.g., mercaptopurine, thioguanine, pentostatin). Examples of natural products useful for the treatment or prevention (reduction in the likelihood of developing or the likelihood of reoccurrence of) of T-cell malignancies in the methods and compositions of the invention include but are not limited to vinca alkaloids (e.g., vinblastin, vincristine), epipodophyllotoxins (e.g., etoposide), antibiotics (e.g., daunorubicin, doxorubicin, bleomycin), enzymes (e.g., L-asparaginase), or biological response modifiers (e.g., interferon alpha).

Examples of alkylating agents useful for the treatment or prevention (reduction in the likelihood of developing or the likelihood of reoccurrence of) of a proliferative disorder such as cancer in the methods and compositions of the invention include but are not limited to, nitrogen mustards (e.g., mechlorethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomustine, semustine, streptozocin, etc.), or triazenes (decarbazine, etc.). Examples of antimetabolites useful for the treatment or prevention (reduction in the likelihood of developing or the likelihood of reoccurrence of) of cancer in the methods and compositions of the invention include but are not limited to folic acid analog (e.g., methotrexate), or pyrimidine analogs (e.g., fluorouracil, floxuridine, Cytarabine), purine analogs (e.g., mercaptopurine, thioguanine, pentostatin). Examples of natural products useful for the treatment or prevention (reduction in the likelihood of developing or the likelihood of reoccurrence of) of cancer in the methods and compositions of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin), enzymes (e.g., L-asparaginase), or biological response modifiers (e.g., interferon alpha). Examples of hormones and antagonists useful for the treatment or prevention (reduction in the likelihood of developing or the likelihood of reoccurrence of) of cancer in the methods and compositions of the invention include but are not limited to adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), gonadotropin releasing hormone analog (e.g., leuprolide). Other agents that can be used in the methods and with the compositions of the invention for the treatment or prevention (reduction in the likelihood of developing or the likelihood of reoccurrence of) of cancer include platinum coordination complexes (e.g., cisplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide).

In one embodiment, the compounds of the invention can be used in combination with an immunotherapeutic agent for the treatment of a proliferative disorder such as cancer, or to prevent (reduce the likelihood) the reoccurrence of a proliferative disorder such as cancer. Immunotherapy (also called biological response modifier therapy, biologic therapy, biotherapy, immune therapy, or biological therapy) is treatment that uses parts of the immune system to fight disease. Immunotherapy can help the immune system recognize cancer cells, or enhance a response against cancer cells. Immunotherapies include active and passive immunotherapies. Active immunotherapies stimulate the body's own immune system while passive immunotherapies generally use immune system components created outside of the body.

Examples of active immunotherapies include: cancer vaccines, tumor cell vaccines (autologous or allogeneic), dendritic cell vaccines, antigen vaccines, anti-idiotype vaccines, DNA vaccines, Lymphokine-Activated Killer (LAK) Cell Therapy, or Tumor-Infiltrating Lymphocyte (TIL) Vaccine with Interleukin-2 (IL-2). Active immunotherapies are currently being used to treat or being tested to treat various types of cancers, including melanoma, kidney (renal) cancer, bladder cancer, prostate cancer, ovarian cancer, breast cancer, colorectal cancer, lung cancer, leukemia, prostate cancer, non-Hodgkin's lymphoma, pancreatic cancer, lymphoma, multiple myeloma, head and neck cancer, liver cancer, malignant brain tumors, and advanced melanoma.

Examples of passive immunotherapies include: monoclonal antibodies and targeted therapies containing toxins. Monoclonal antibodies include naked antibodies and conjugated antibodies (also called tagged, labeled, or loaded antibodies). Naked monoclonal antibodies do not have a drug or radioactive material attached whereas conjugated monoclonal antibodies are joined to a chemotherapy drug (chemolabeled), a radioactive particle (radiolabeled), or a toxin (immunotoxin). A number of naked monoclonal antibody drugs have been approved for treating cancer, including:

Rituximab (Rituxan), an antibody against the CD20 antigen used to treat B cell non-Hodgkin lymphoma; Trastuzumab (Herceptin), an antibody against the HER2 protein used to treat advanced breast cancer; Alemtuzumab (Campath), an antibody against the CD52 antigen used to treat B cell chronic lymphocytic leukemia (B-CLL); Cetuximab (Erbitux), an antibody against the EGFR protein used in combination with irinotecan to treat advanced colorectal cancer and to treat head and neck cancers; and Bevacizumab (Avastin) which is an antiangiogenesis therapy that works against the VEGF protein and is used in combination with chemotherapy to treat metastatic colorectal cancer. A number of conjugated monoclonal antibodies have been approved for treating cancer, including: Radiolabeled antibody Ibritumomab tiuxetan (Zevalin) which delivers radioactivity directly to cancerous B lymphocytes and is used to treat B cell non-Hodgkin lymphoma; radiolabeled antibody Tositumomab (Bexxar) which is used to treat certain types of non-Hodgkin lymphoma; and immunotoxin Gemtuzumab ozogamicin (Mylotarg) which contains calicheamicin and is used to treat acute myelogenous leukemia (AML). BL22 is a conjugated monoclonal antibody currently in testing for treating hairy cell leukemia and there are several immunotoxin clinical trials in progress for treating leukemias, lymphomas, and brain tumors. There are also approved radiolabeled antibodies used to detect cancer, including OncoScint for detecting colorectal and ovarian cancers and ProstaScint for detecting prostate cancers. Targeted therapies containing toxins are toxins linked to growth factors and do not contain antibodies. An example of an approved targeted therapy containing toxins is denileukin diftitox (Ontak) which is used to treat a type of skin lymphoma (cutaneous T cell lymphoma).

Examples of adjuvant immunotherapies include: cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guérin (BCG); Keyhole limpet hemocyanin (KLH); Incomplete Freund's adjuvant (IFA); QS-21; DETOX; Levamisole; and Dinitrophenyl (DNP). Clinical studies have shown that combining IL-2 with other cytokines, such as IFN-alpha, can lead to a synergistic response.

Several types of immunotherapies are being used to treat melanoma patients. IFN-alpha and IL-2 are approved for treatment of people with metastatic melanoma. BCG is being tested in combination with melanoma vaccines and other immunotherapies. Tumor-infiltrating lymphocytes have been shown to shrink melanoma tumors in a phase 1 clinical trial. Human monoclonal antibodies to ganglioside antigens have been shown to regress cutaneous recurrent melanoma tumors. Some autologous and allogeneic tumor cell vaccines, antigen vaccines (including polyvalent antigen vaccines), viral vaccines and dendritic cell vaccines have also been shown to shrink tumors. Clinical trials continue for these and other melanoma immunotherapies. Melanoma patients with a high IgM response often survive better than those who elicit no or low IgM antibodies (Morton et al., 1992). Combined IL-12/TNF-alpha immunotherapy has been shown to significantly retard tumor growth in three tumor models in mice (B16F10 melanoma, Lewis lung (LL/2) carcinoma and L1 sarcoma) as compared with controls and mice treated with either cytokine alone. IFN-alpha is approved for the treatment of malignant melanoma, chronic myelogenous leukemia (CML), hairy cell leukemia, and Kaposi's sarcoma.

Several types of immunotherapies are being used to treat patients that have renal cancer. IFN-alpha and IL-2 are approved for treatment of people with metastatic renal (kidney) cancer. A combination therapy using IL-2, interferon, and chemotherapy is being tested for treatment of renal cancer. Treatment with a tumor cell vaccine plus the adjuvant BCG has been shown to shrink tumors in some advanced renal cancer patients. DNA vaccines and tumor-infiltrating lymphocytes are also being tested as treatments for renal cancer. Chimeric bispecific G250/anti-CD3 monoclonal antibodies have been shown to mediate cell lysis of renal cell carcinoma cell lines by cloned human CD8+ T cells or by IL-2 stimulated peripheral blood lymphocytes.

As used herein, a "microtubulin stabilizer" means an anticancer agent which acts by arresting cells in the G2-M phases due to stabilization of microtubules. Agents which are microtubulin stabilizers can be used in combination with the compounds of the invention to treat patients having a proliferative disorder such as cancer, or to prevent (reduce the likelihood of) the reoccurrence of a proliferative disorder such as cancer. Examples of microtubulin stabilizers include paclitaxel and paclitaxel analogs. Additional examples of microtubulin stabilizers included without limitation the following marketed drugs and drugs in development: Discodermolide (also known as NVP-XX-A-296); Epothilones (such as Epothilone A, Epothilone B, Epothilone C (also known as desoxyepothilone A or dEpoA); Epothilone D (also referred to as KOS-862, dEpoB, and desoxyepothilone B); Epothilone E; Epothilone F; Epothilone B N-oxide; Epothilone A N-oxide; 16-aza-epothilone B; 21-aminoepothilone B (also known as BMS-310705); 21-hydroxyepothilone D (also known as Desoxyepothilone F and dEpoF), 26-fluoroepothilone); FR-182877 (Fujisawa, also known as WS-9885B), BSF-223651 (BASF, also known as ILX-651 and LU-223651); AC-7739 (Ajinomoto, also known as AVE-8063A and CS-39.HCl); AC-7700 (Ajinomoto, also known as AVE-8062, AVE-8062A, CS-39-L-Ser.HCl, and RPR-258062A); Fijianolide B; Laulimalide; Caribaeoside; Caribaeolin; Taccalonolide; Eleutherobin; Sarcodictyin; Laulimalide; Dictyostatin-1; Jatrophane esters; and analogs and derivatives thereof.

As used herein, a "microtubulin inhibitor" means an anticancer agent which acts by inhibiting tubulin polymerization or microtubule assembly. Agents which are microtubulin inhibitors can be used in combination with the compounds of the invention to treat patients having a proliferative disorder such as cancer, or to prevent (reduce the likelihood of) the reoccurrence of a proliferative disorder such as cancer. Examples of microtubulin inhibitors include without limitation the following marketed drugs and drugs in development: Erbulozole (also known as R-55104); Dolastatin 10 (also known as DLS-10 and NSC-376128); Mivobulin isethionate (also known as CI-980); Vincristine; NSC-639829; ABT-751 (Abbot, also known as E-7010); Altorhyrtins (such as Altorhyrtin A and Altorhyrtin C); Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9); Cemadotin hydrochloride (also known as LU-103793 and NSC-D-669356); Auristatin PE (also known as NSC-654663); Soblidotin (also known as TZT-1027), LS-4559-P (Pharmacia, also known as LS-4577); LS-4578 (Pharmacia, also known as LS-477-P); LS-4477 (Pharmacia), LS-4559 (Pharmacia); RPR-112378 (Aventis); Vincristine sulfate; DZ-3358 (Daiichi); GS-164 (Takeda); GS-198 (Takeda); KAR-2 (Hungarian Academy of Sciences); SAH-49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (also known as LY8-355703); Vitilevuamide; Tubulysin A; Canadensol; Centaureidin (also known as NSC-106969); T-138067 (Tularik, also known as T-67, TL-138067 and TI-138067); COBRA-1 (Parker Hughes Institute, also known as DDE-261 and WHI-261); H10 (Kansas State University); H16 (Kansas State University); Oncocidin A1 (also known as BTO-956 and DIME); DDE-313 (Parker Hughes Institute); SPA-2 (Parker Hughes Institute); SPA-1 (Parker Hughes Institute, also known as SPIKET-P); 3-IAABU (Cytoskeleton/Mt. Sinai School of Medicine, also known as MF-569); Narcosine (also known as NSC-5366); Nascapine, D-24851 (Asta Medica), A-105972 (Abbott); Hemiasterlin; 3-BAABU (Cytoskeleton/Mt. Sinai School of Medicine, also known as MF-191); TMPN (Arizona State University); Vanadocene acetylacetonate; T-138026 (Tularik); Monsatrol; Inanocine (also known as NSC-698666); 3-IAABE (Cytoskeleton/Mt. Sinai School of Medicine); A-204197 (Abbott); T-607 (Tularik, also known as T-900607); RPR-115781 (Aventis); Eleutherobins (such as Desmethyleleutherobin, Desaetyleleutherobin, Isoeleutherobin A, and Z-Eleutherobin); Halichondrin B; D-64131 (Asta Medica); D-68144 (Asta Medica); Diazonamide A; A-293620 (Abbott); NPI-2350 (Nereus); TUB-245 (Aventis); A-259754 (Abbott); Diozostatin; (−)-Phenylahistin (also known as NSCL-96F037); D-68838 (Asta Medica); D-68836 (Asta Medica); Myoseverin B; D-43411 (Zentaris, also known as D-81862); A-289099 (Abbott); A-318315 (Abbott); HTI-286 (also known as SPA-110, trifluoroacetate salt) (Wyeth); D-82317 (Zentaris); D-82318 (Zentaris); SC-12983 (NCI); Resverastatin phosphate sodium; BPR-0Y-007 (National Health Research Institutes); SSR-250411 (Sanofi); Combretastatin A4; and analogs and derivatives thereof.

Figure 2:
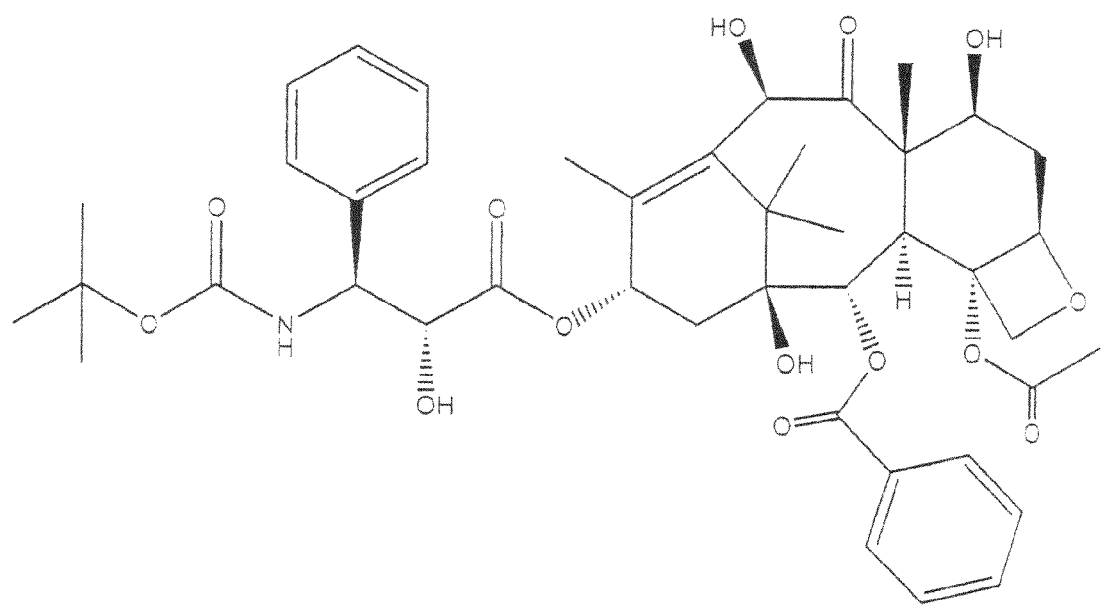
FIG. 2 is the structure of docetaxol (Taxotere®).
Figure 3:
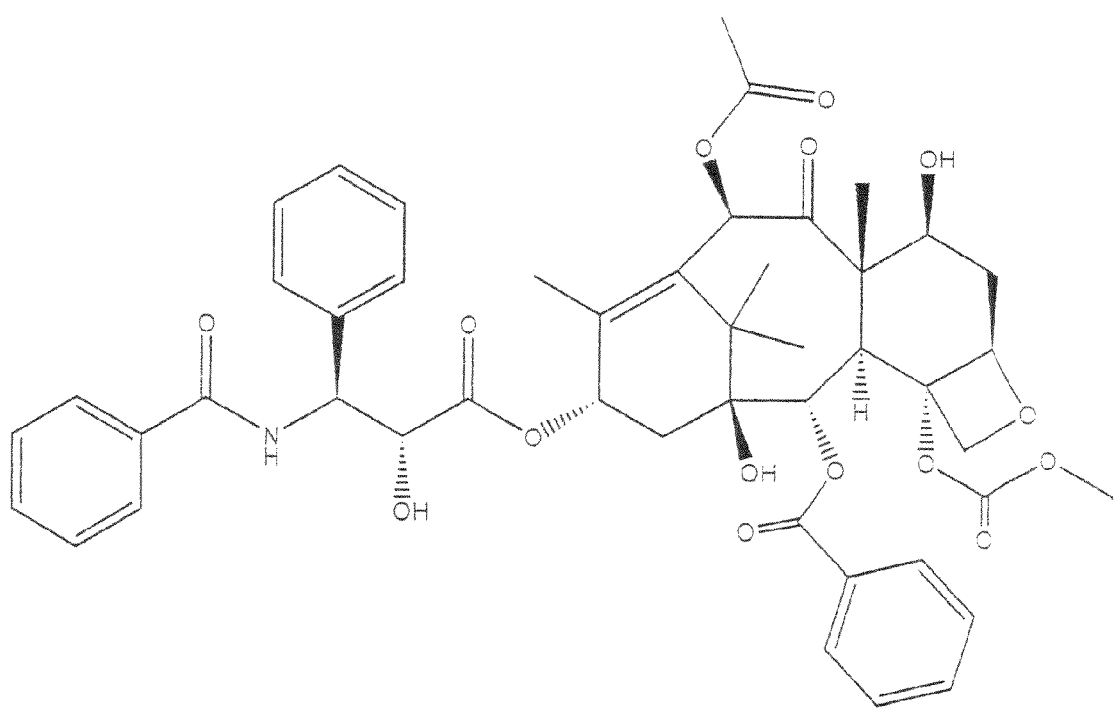
FIGS. 3-23 are each the structure of a paclitaxel analog.
Figure 4:
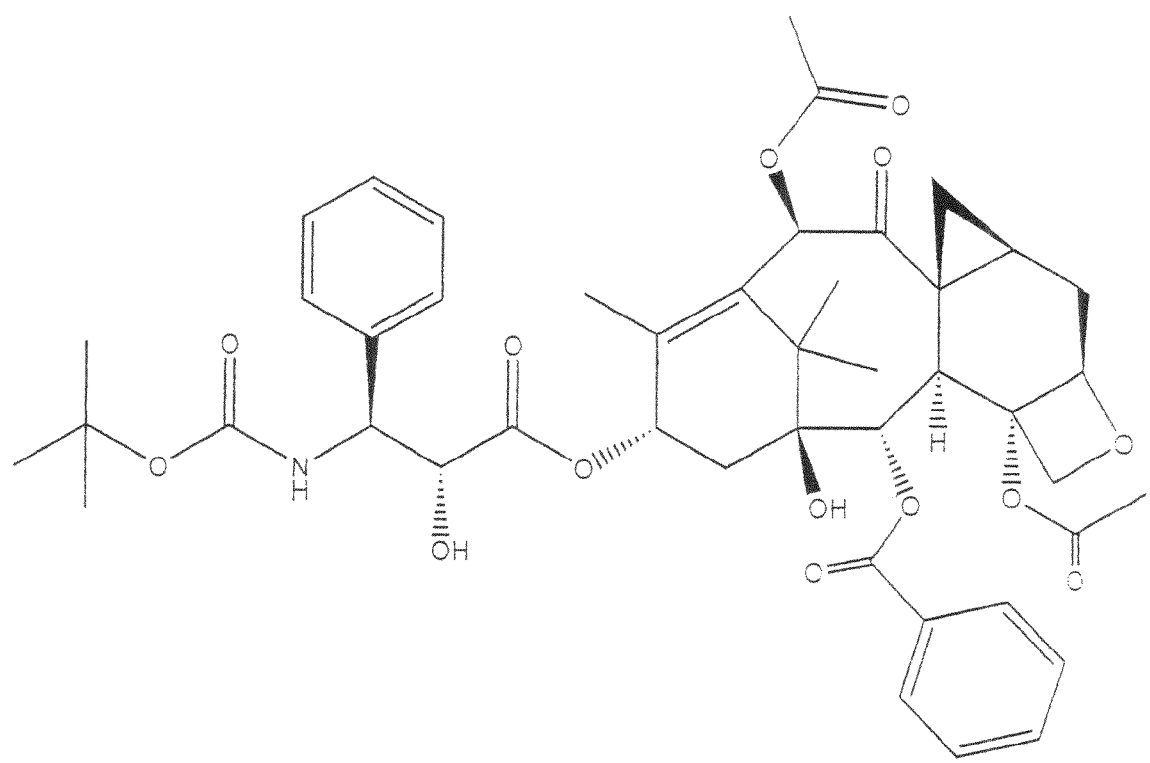
Figure 5:
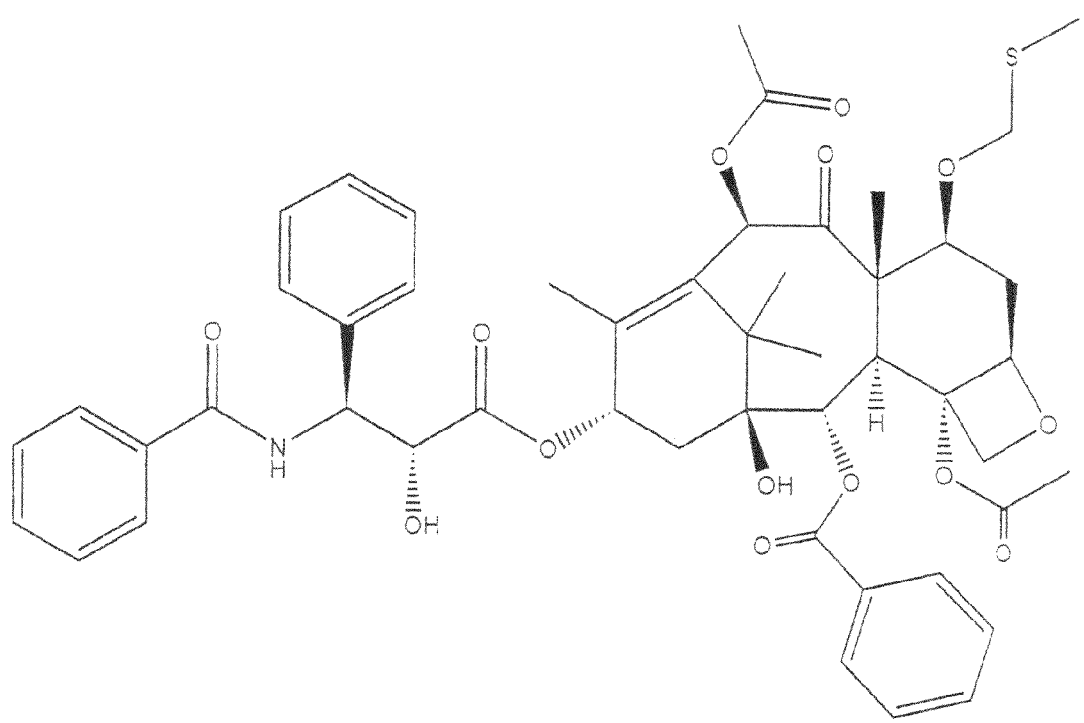
Figure 6:
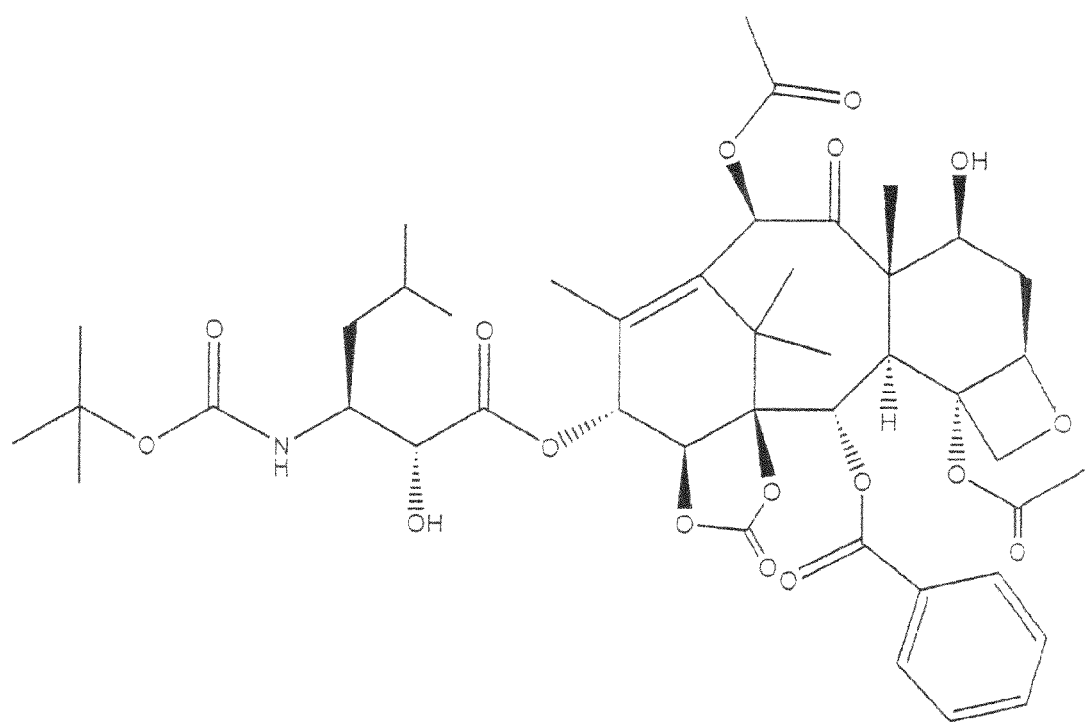
Figure 7:
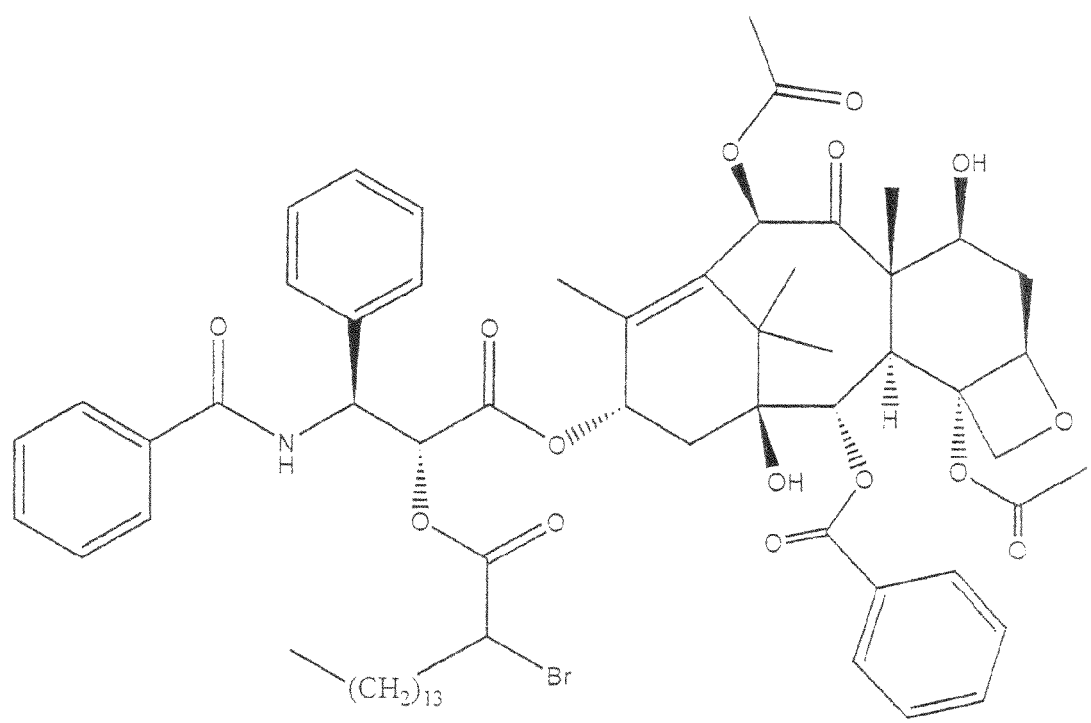
Figure 8:
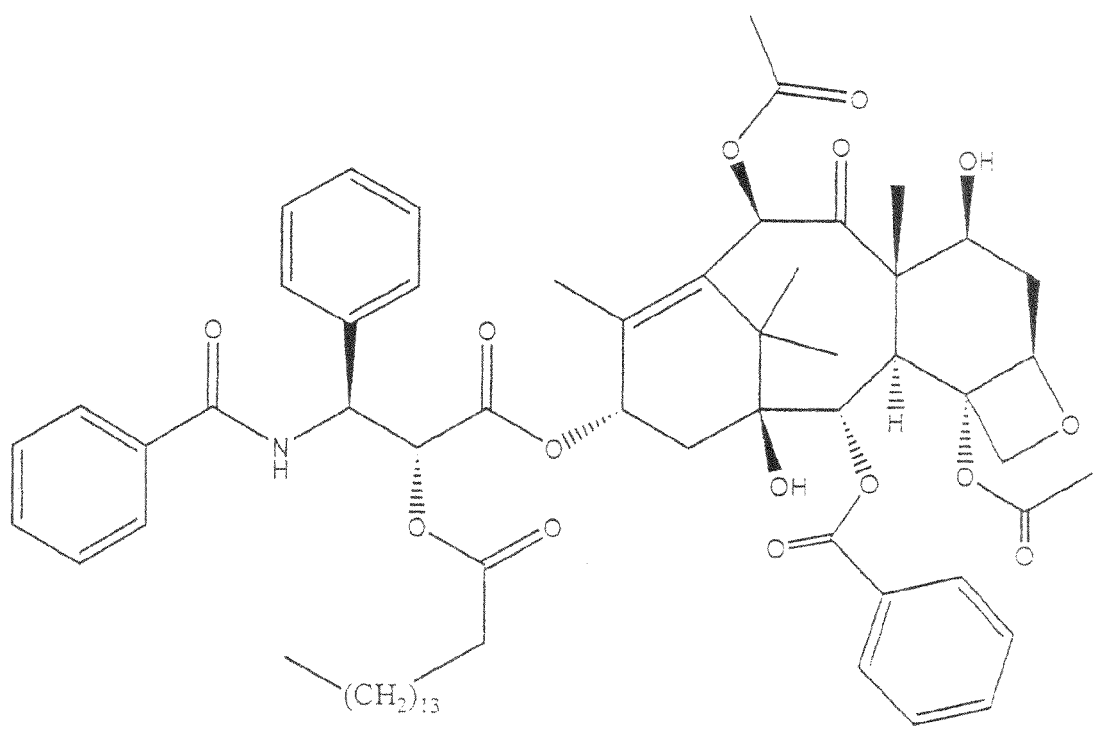
Figure 9:
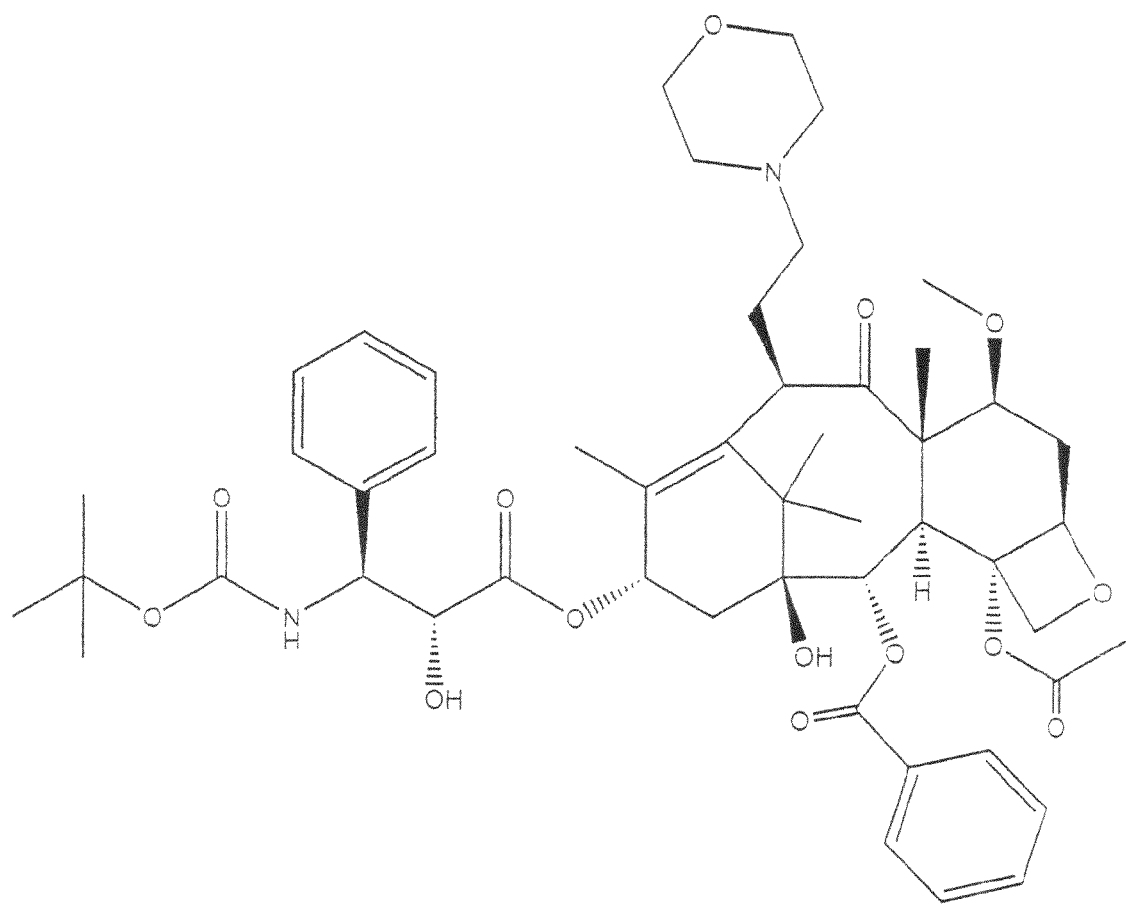
Figure 10:
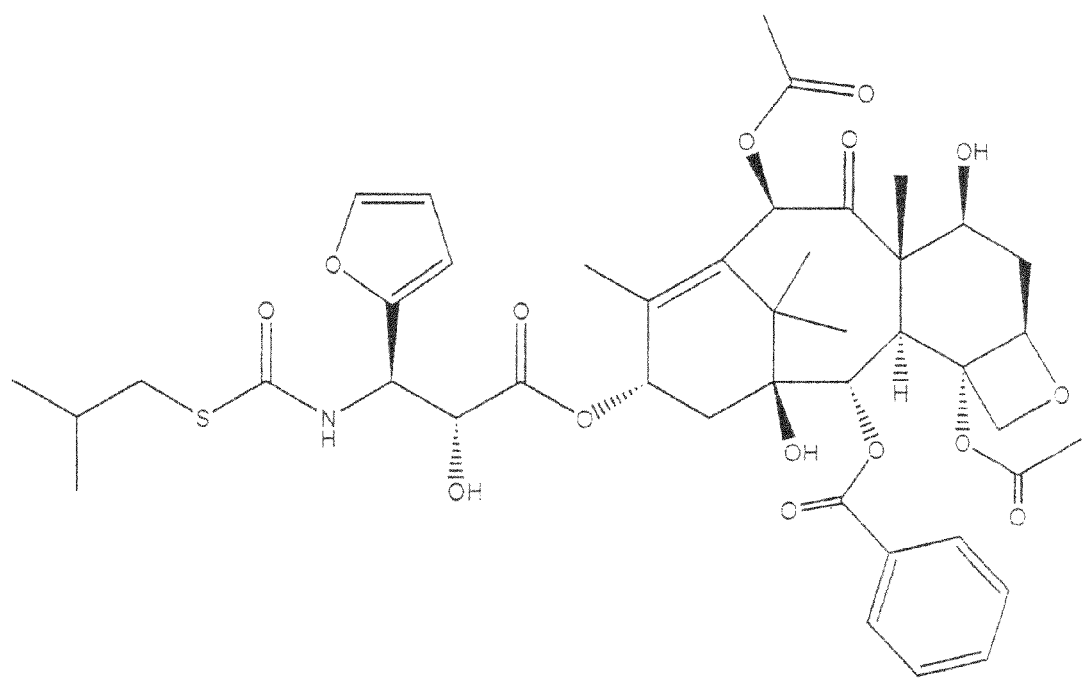
Figure 11:
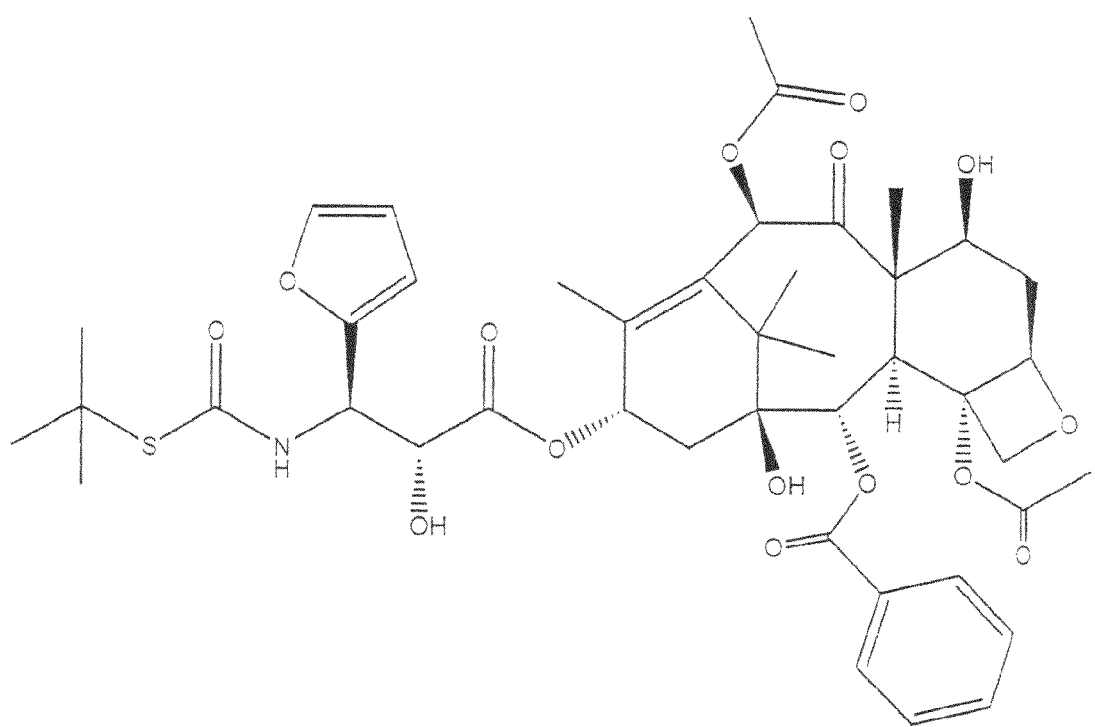
Figure 12:
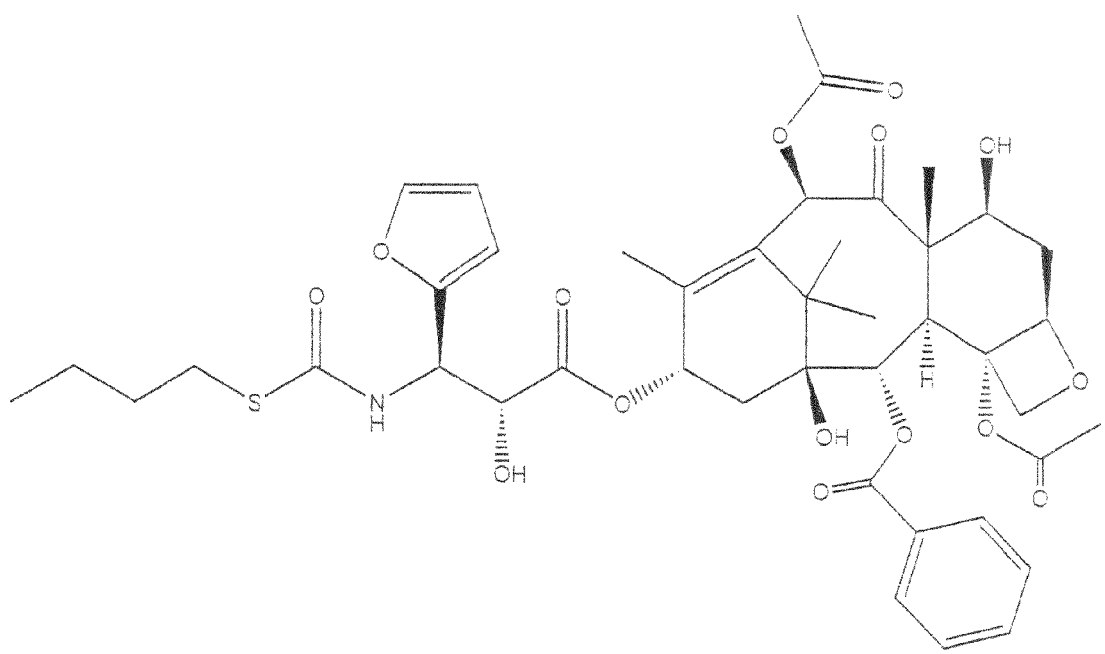
Figure 13:
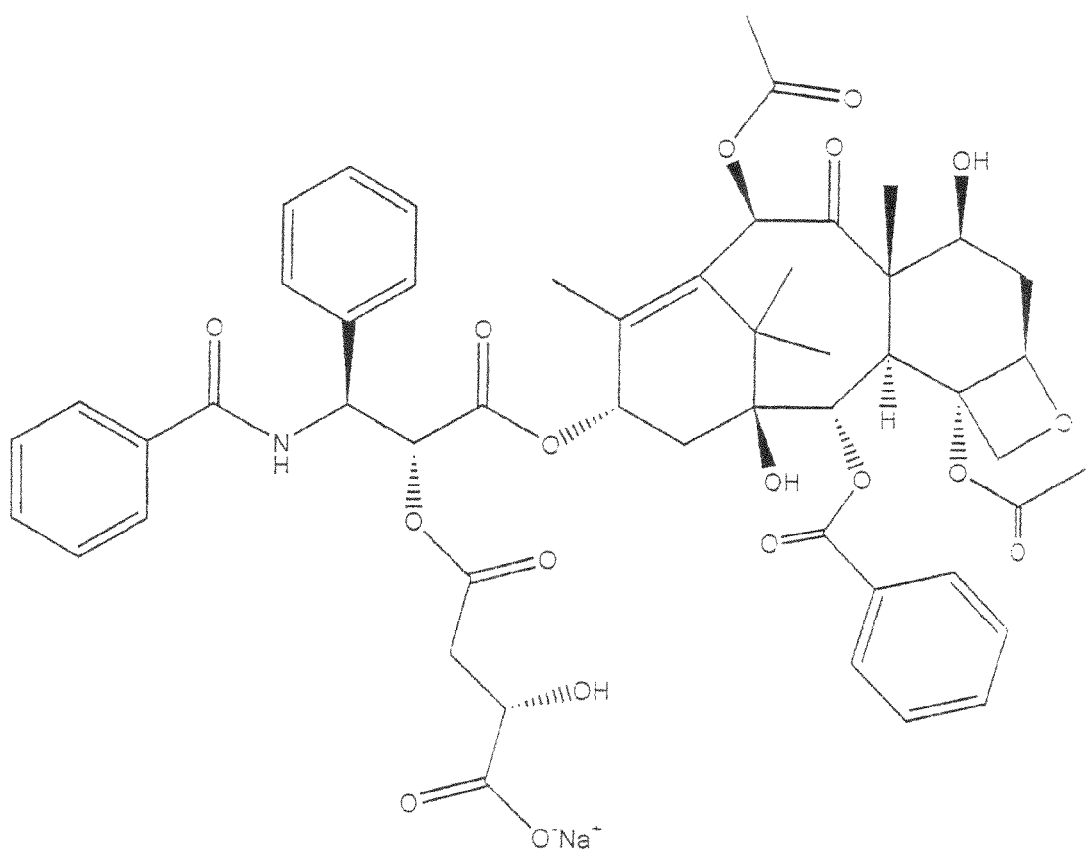
Figure 14:
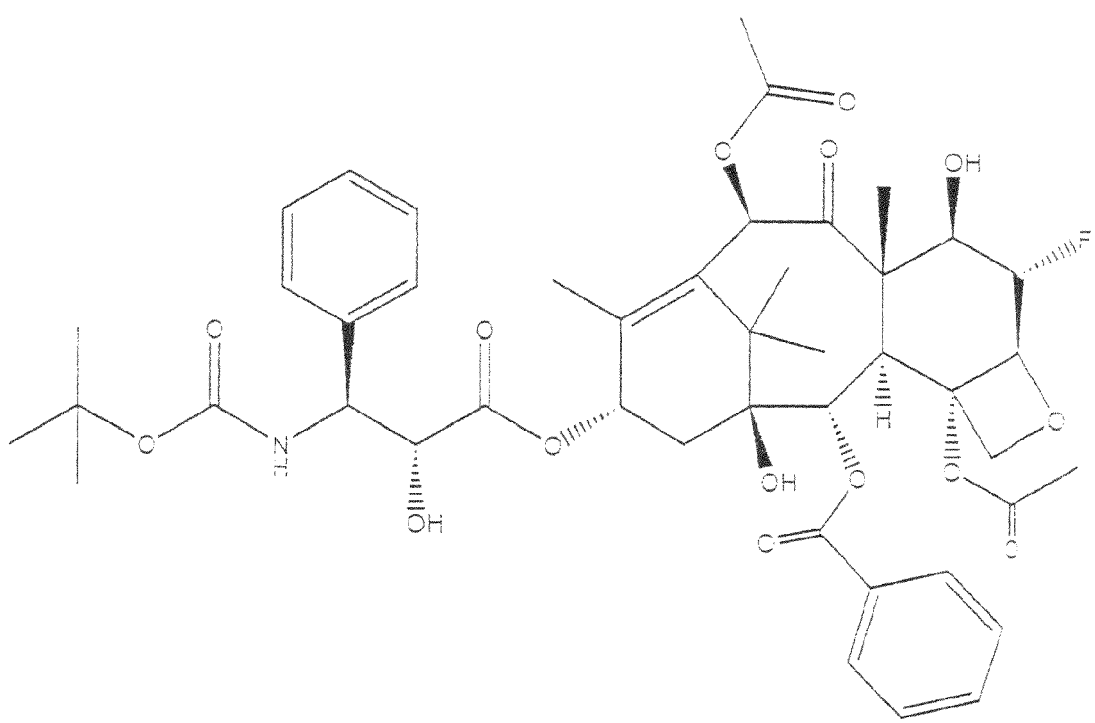
Figure 15:
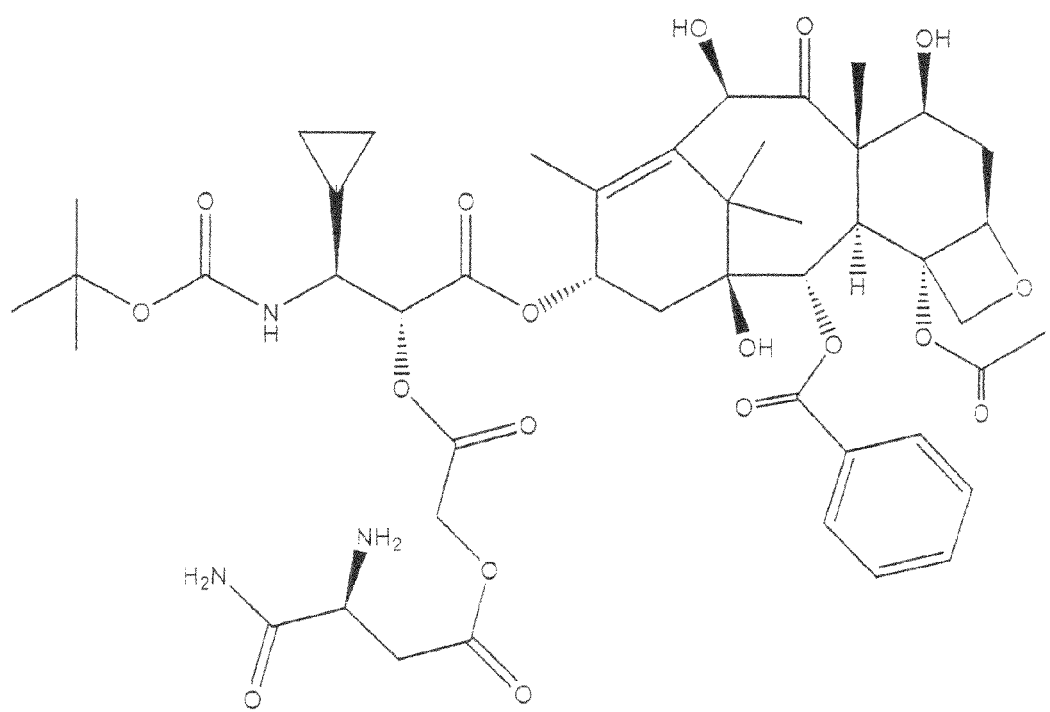
Figure 16:
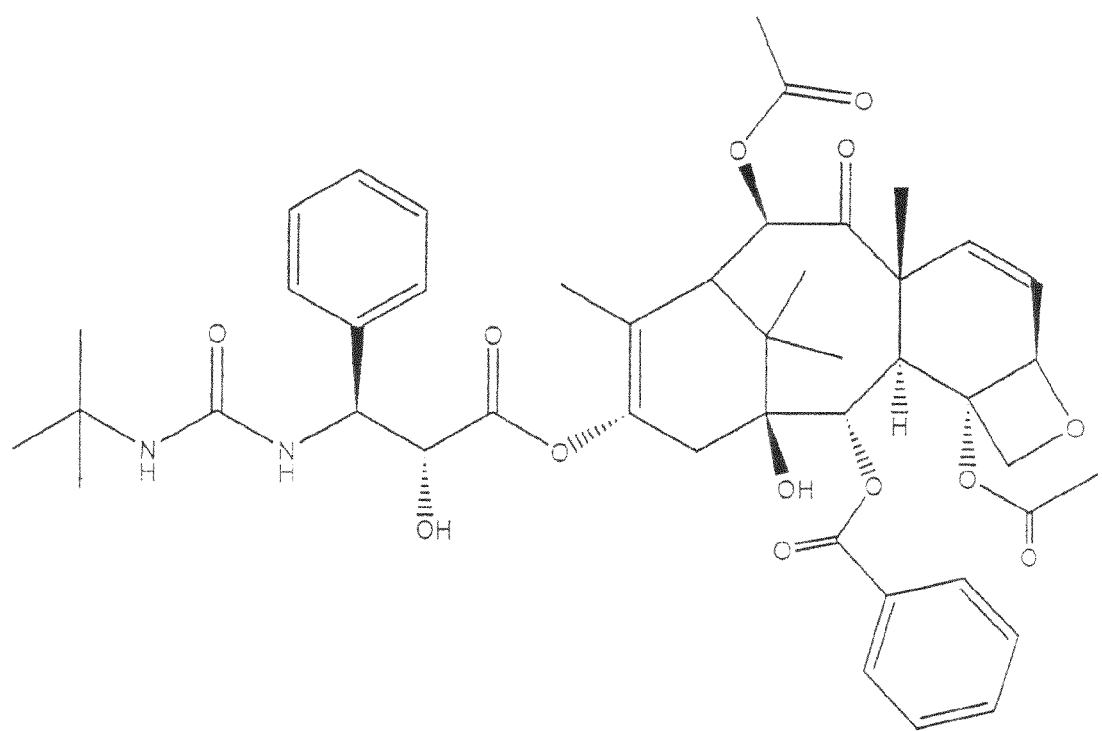
Figure 17:
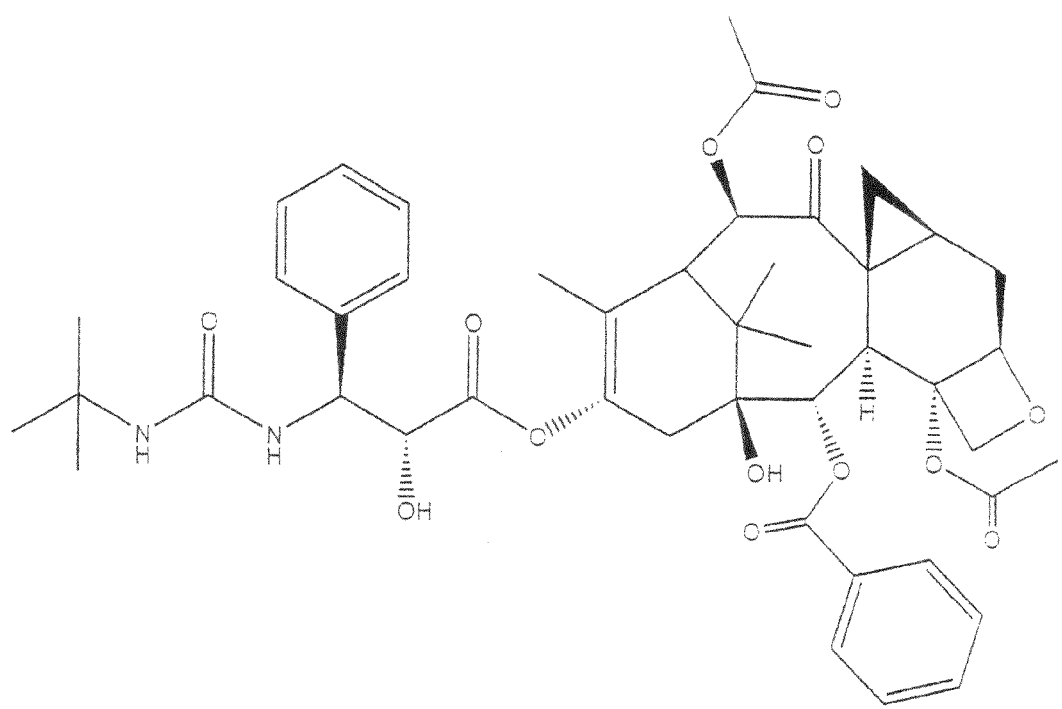
Figure 18:
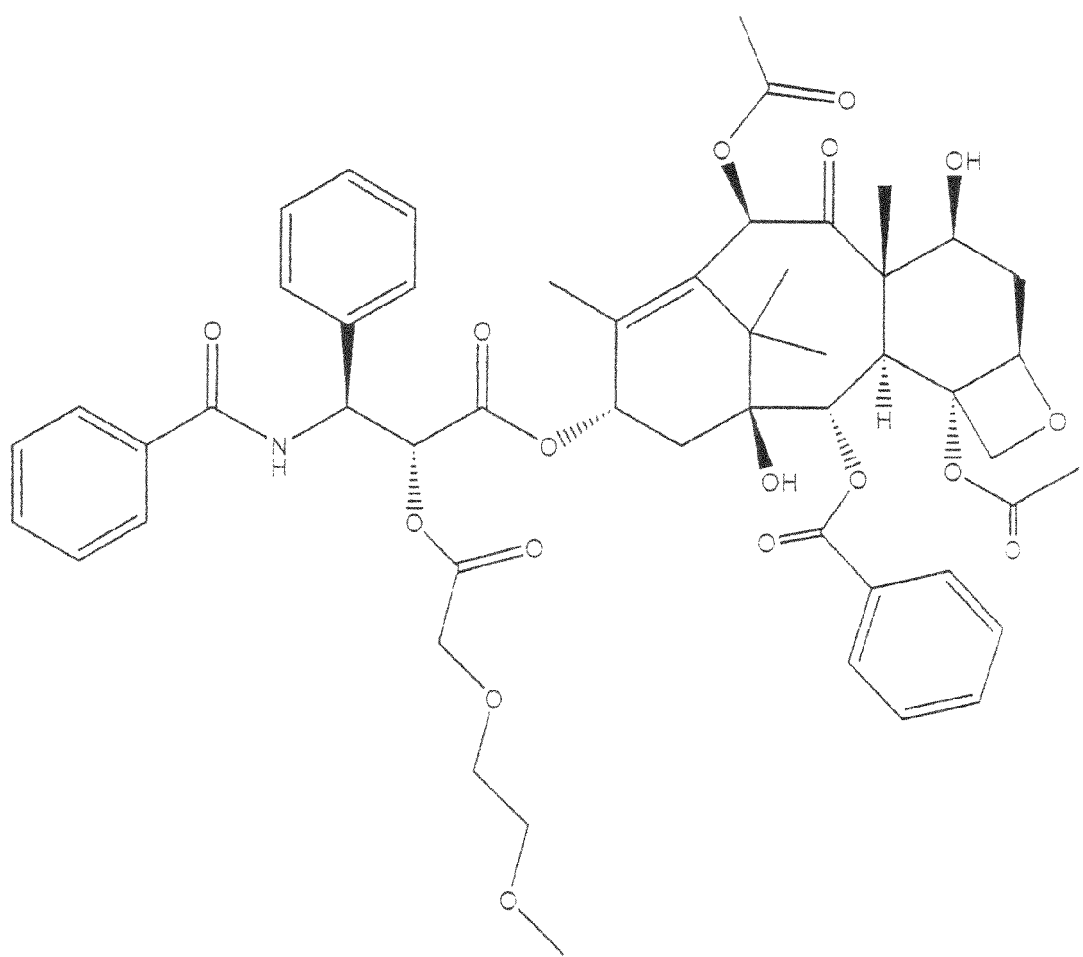
Figure 19:
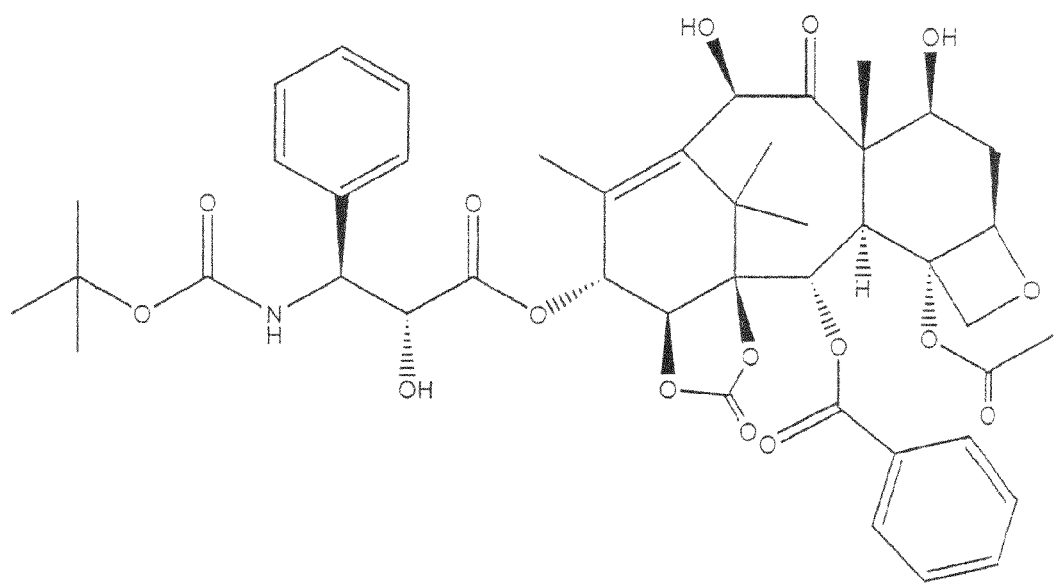
Figure 20:
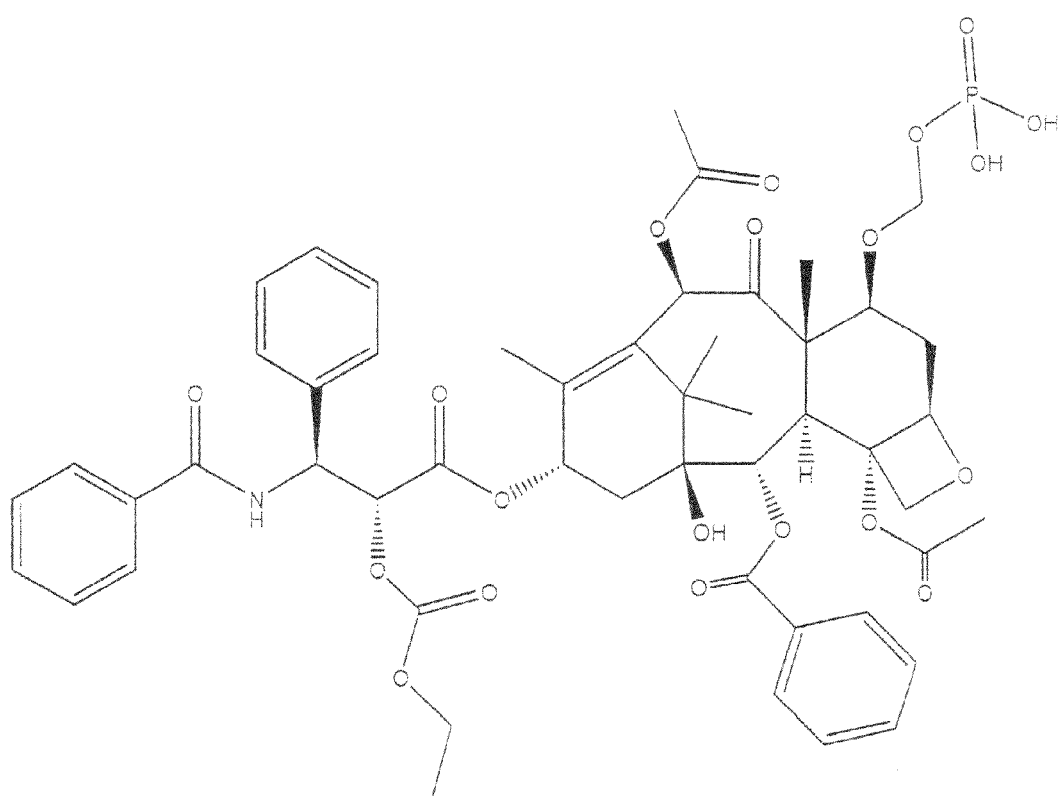
Figure 21:
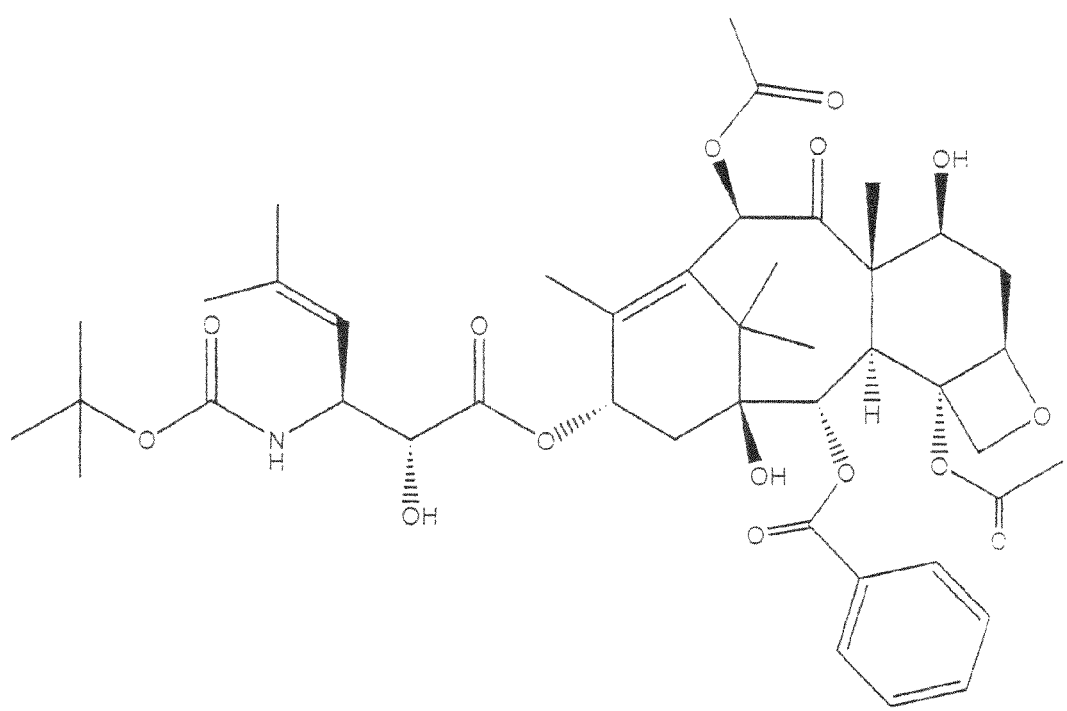
Figure 22:
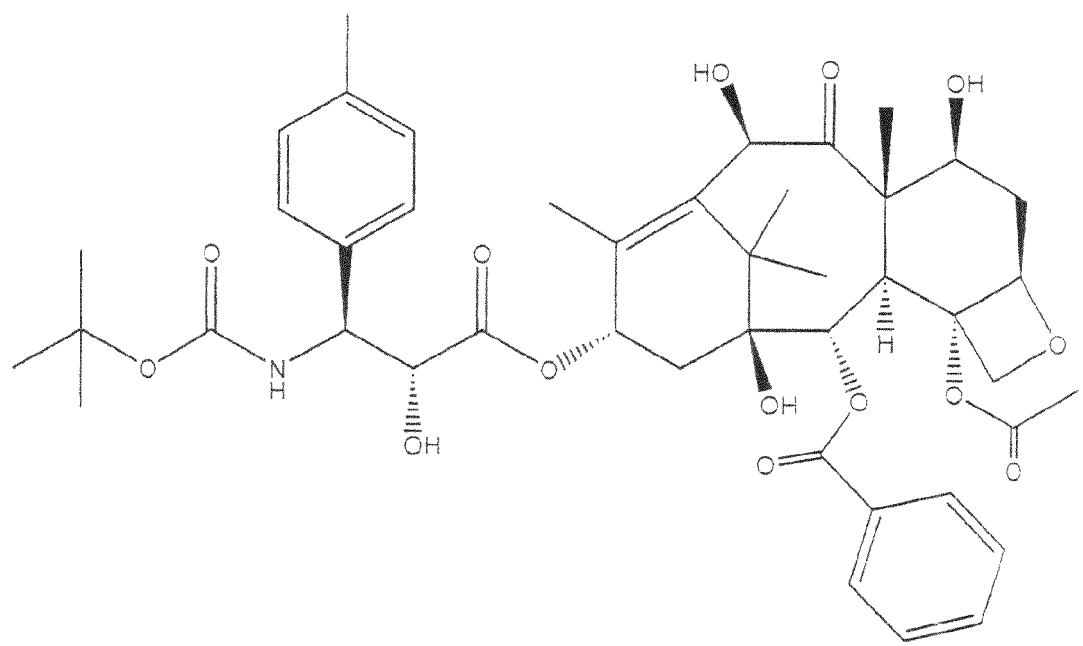
Figure 23:
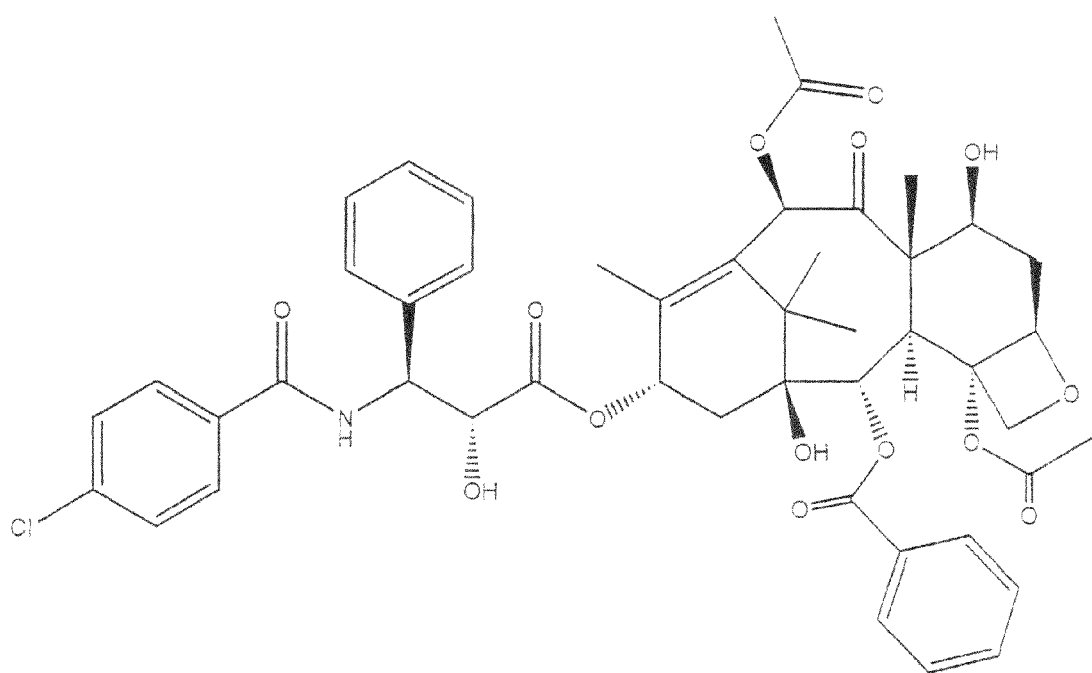

Paclitaxel, also referred to as "Taxol®", is a well-known anti-cancer drug which acts by enhancing and stabilizing microtubule formation. The structure of paclitaxel is shown in FIG. 1. Many analogs of paclitaxel are known, including paclitaxel, the structure of which is shown in FIG. 2. Docetaxol is also referred to as "Taxotere®". The structures of other paclitaxel analogs are shown in FIGS. 3-23. These compounds have the basic taxane skeleton as a common structure feature and have also been shown to have the ability to arrest cells in the G2-M phases due to stabilization of microtubules. Thus, it is apparent from FIGS. 3-23 that a wide variety of substituents can decorate the taxane skeleton without adversely affecting biological activity. It is also apparent that zero, one or both of the cyclohexane rings of a paclitaxel analog can have a double bond at the indicated positions. For clarity purposes, the basic taxane skeleton is shown below in Structural Formula (XXVI'):

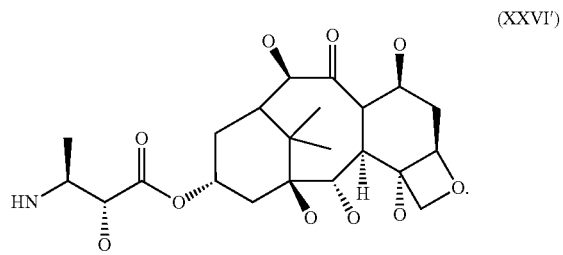
(XXVI')

Double bonds have been omitted from the cyclohexane rings in the taxane skeleton represented by Structural Formula (XXVI'). The basic taxane skeleton can include zero or one double bond in one or both cyclohexane rings, as indicated in FIGS. 3-23 and Structural Formulas (XXVII') and (XXVIII') below. A number of atoms have also been omitted from Structural Formula (XXVI') to indicate sites in which structural variation commonly occurs among paclitaxel analogs. For example, substitution on the taxane skeleton with simply an oxygen atom indicates that hydroxyl, acyl, alkoxy or another oxygen-bearing substituent is commonly found at the site. These and other substitutions on the taxane skeleton can be made without losing the ability to enhance and stabilize microtubule formation. Thus, the term "paclitaxel analog" is defined herein to mean a compound which has the basic taxane skeleton and which promotes microtubule formation. paclitaxel analogs may be formulated as a nanoparticle colloidal composition to improve the infusion time and to eliminate the need to deliver the drug with Cremophor which causes hypersensitivity reactions in some patients. An example of a paclitaxel analog formulated as a nanoparticle colloidal composition is Abraxane, which is a nanoparticle colloidal composition of protein-stabilized paclitaxel that is reconstituted in saline.

Typically, the paclitaxel analogs used herein are represented by Structural Formula (XXVII') or (XXVIII'):

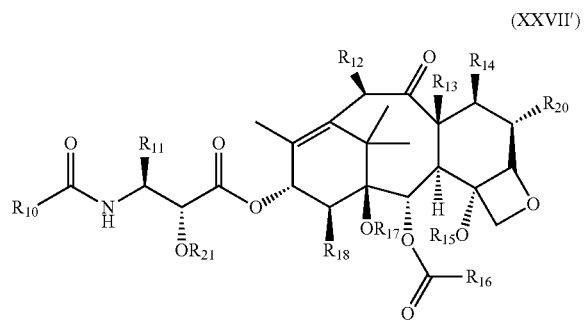
(XXVII')

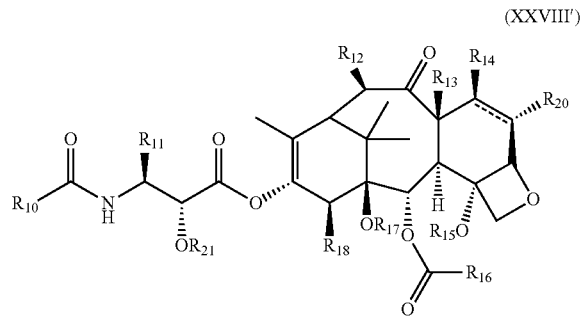
(XXVIII')

Wherein: $R_{10}$ is a lower alkyl group, a substituted lower alkyl group, a phenyl group, a substituted phenyl group, —$SR_{19}$, —$NHR_{19}$ or —$OR_{19}$.

$R_{11}$ is a lower alkyl group, a substituted lower alkyl group, an aryl group or a substituted aryl group.

$R_{12}$ is —H, —OH, lower alkyl, substituted lower alkyl, lower alkoxy, substituted lower alkoxy, —O—C(O)-(lower alkyl), —O—C(O)-(substituted lower alkyl), —O—CH$_2$—O-(lower alkyl) —S—CH$_2$—O-(lower alkyl).

$R_{13}$ is —H, —CH$_3$, or, taken together with $R_{14}$, —CH$_2$—.

$R_{14}$ is —H, —OH, lower alkoxy, —O—C(O)-(lower alkyl), substituted lower alkoxy, —O—C(O)-(substituted lower alkyl), —O—CH$_2$—O—P(O)(OH)$_2$, —O—CH$_2$—O-(lower alkyl), —O—CH$_2$—S-(lower alkyl) or, taken together with $R_{20}$, a double bond.

$R_{15}$—H, lower acyl, lower alkyl, substituted lower alkyl, alkoxymethyl, alkthiomethyl, —C(O)—O(lower alkyl), —C(O)—O(substituted lower alkyl), —C(O)—NH (lower alkyl) or —C(O)—NH (substituted lower alkyl).

$R_{16}$ is phenyl or substituted phenyl.

$R_{17}$ is —H, lower acyl, substituted lower acyl, lower alkyl, substituted, lower alkyl, (lower alkoxy)methyl or (lower alkyl)thiomethyl.

$R_{18}$—H, —CH$_3$ or, taken together with $R_{17}$ and the carbon atoms to which $R_{17}$ and $R_{18}$ are bonded, a five or six membered a non-aromatic heterocyclic ring.

$R_{19}$ is a lower alkyl group, a substituted lower alkyl group, a phenyl group, a substituted phenyl group.

$R_{20}$ is —H or a halogen.

$R_{21}$ is —H, lower alkyl, substituted lower alkyl, lower acyl or substituted lower acyl.

Preferably, the variables in Structural Formulas (XXVII') and (XXVIII') are defined as follows: $R_{10}$ is phenyl, tert-butoxy, —S—CH$_2$—CH—(CH$_3$)$_2$, —S—CH(CH$_3$)$_3$, —S—(CH$_2$)$_3$CH$_3$, —O—CH(CH$_3$)$_3$, —NH—CH(CH$_3$)$_3$, —CH═C(CH$_3$)$_2$ or para-chlorophenyl; $R_{11}$ is phenyl, (CH$_3$)$_2$ CHCH$_2$—, -2-furanyl, cyclopropyl or para-toluoyl; $R_{12}$ is —H, —OH, CH$_3$CO— or —(CH$_2$)$_2$—N-morpholino; $R_{13}$ is methyl, or, $R_{13}$ and $R_{14}$, taken together, are —CH$_2$—; $R_{14}$ is —H, —CH$_2$SCH$_3$ or —CH$_2$—O—P(O)(OH)$_2$; $R_{15}$ is CH$_3$CO—;

$R_{16}$ is phenyl; $R_{17}$—H, or, $R_{17}$ and $R_{18}$, taken together, are —O—CO—O—;

$R_{18}$ is —H; $R_{20}$ is —H or —F; and $R_{21}$ is —H, —C(O)—CHBr—(CH$_2$)$_{13}$—CH$_3$ or —C(O)—(CH$_2$)$_{14}$—CH$_3$; —C(O)—CH$_2$—CH(OH)—COOH, —C(O)—CH$_2$—O—C(O)—CH$_2$CH(NH$_2$)—CONH$_2$, —C(O)—CH$_2$—O—CH$_2$CH$_2$OCH$_3$ or —C(O)—O—C(O)—CH$_2$CH$_3$.

Figure 24:
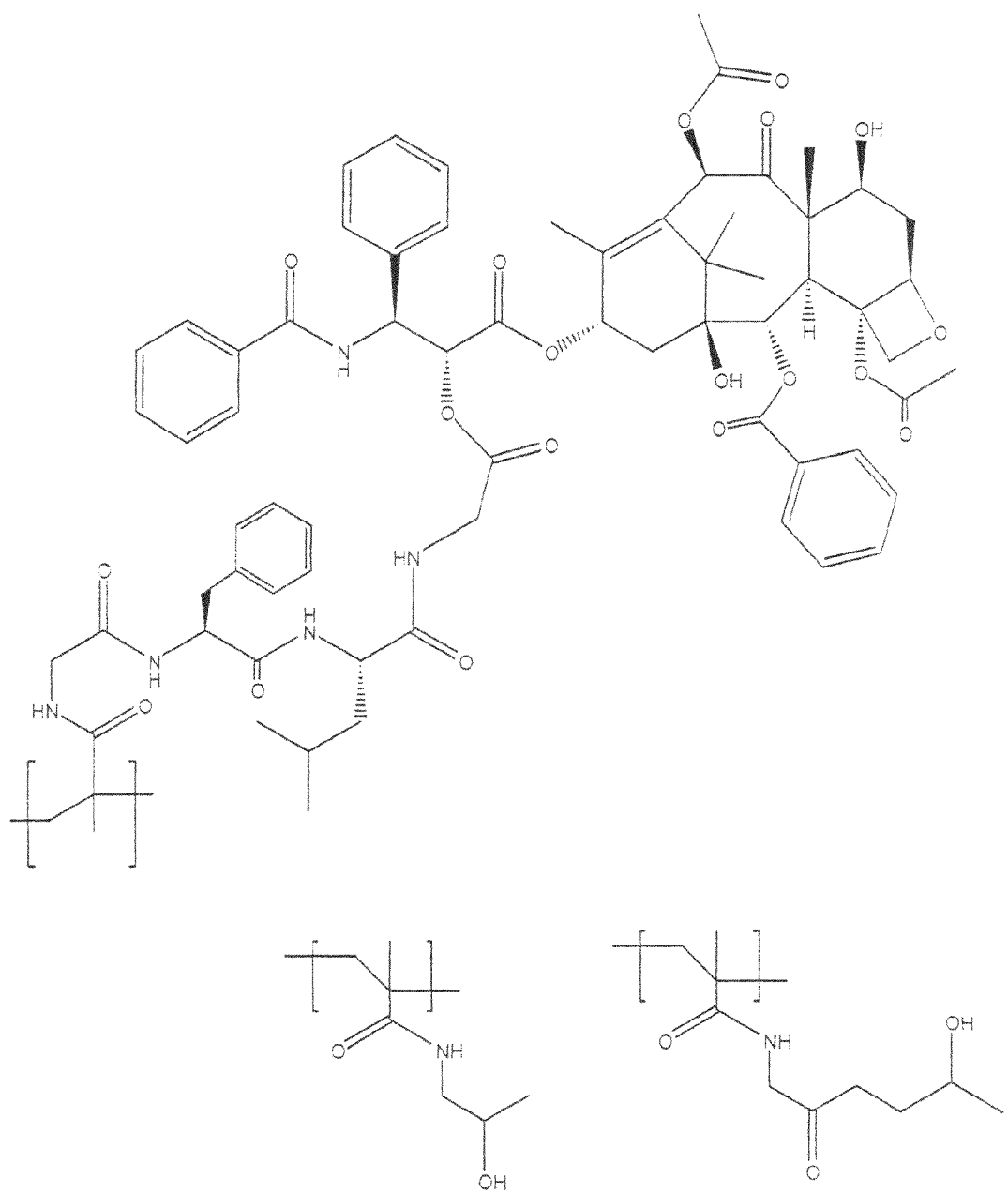
FIG. 24 is the structure of a polymer comprising a paclitaxel analog group pendent from the polymer backbone. The polymer is a terpolymer of the three monomer units shown.

A paclitaxel analog can also be bonded to or be pendent from a pharmaceutically acceptable polymer, such as a polyacrylamide. One example of a polymer of this type is shown in FIG. 24. The term "paclitaxel analog", as it is used herein, includes such polymers.

In some embodiments, paclitaxel analogs have a taxane skeleton represented by Structural Formula XXIX', wherein W is O, S, or NR. Paclitaxel analogs that have the taxane skeleton shown in Structural Formula XXIX can have various substituents attached to the taxane skeleton and can have a double bond in zero, one or both of the cyclohexane rings as shown, for example in FIGS. 3-23.

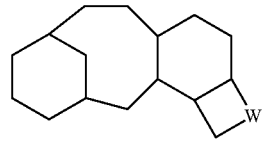

(XXIX')

Various paclitaxel analogs and paclitaxel formulations are described in Hennenfent, et al., *Annals of Oncology*, (2006) 17:735-749; Gradishar, *Expert Opin. Pharmacother*, (2006) 7(8):1041-53; Attard, et al., *Pathol Biol.*, (2006) 54(2):72-84; Straubinger, et al., *Methods Enzymol*, (2005) 391:97-117; Ten Tije, et al., *Clin Pharmacokinet*, (2003) 42(7):665-85; and Nuijen, et al., *Invest New Drugs*, (2001) 19(2):143-53, the entire teachings of which are incorporated herein by reference.

In some embodiments, the invention provides a method for treating or inhibiting angiogenesis in a subject in need thereof, comprising administering to the subject an effective amount of a compound of the invention. As used herein, the term "angiogenesis" refers to a fundamental process of generating new blood vessels in tissues or organs. Angiogenesis is involved with or associated with many diseases or conditions, including, but not limited to: cancer; ocular neovascular disease; age-related macular degeneration; diabetic retinopathy, retinopathy of prematurity; corneal graft rejection; neovascular glaucoma; retrolental fibroplasias; epidemic keratoconjunctivitis; Vitamin A deficiency; contact lens overwear; atopic keratitis; superior limbic keratitis; pterygium keratitis sicca; sjogrens; acne rosacea; warts; eczema; phylectenulosis; syphilis; Mycobacteria infections; lipid degeneration; chemical burns; bacterial ulcers; fungal ulcers; Herpes simplex infections; Herpes zoster infections; protozoan infections; Kaposi's sarcoma; Mooren's ulcer; Terrien's marginal degeneration; marginal keratolysis; rheumatoid arthritis; systemic lupus; polyarteritis; trauma; Wegener's sarcoidosis; scleritis; Stevens-Johnson disease; pemphigoid; radial keratotomy; corneal graph rejection; diabetic retinopathy; macular degeneration; sickle cell anemia; sarcoid; syphilis; pseudoxanthoma elasticum; Paget's disease; vein occlusion; artery occlusion; carotid obstructive disease; chronic uveitis/vitritis; mycobacterial infections; Lyme disease; systemic lupus erythematosis; retinopathy of prematurity; Eales' disease; Behcet's disease; infections causing a retinitis or choroiditis; presumed ocular histoplasmosis; Best's disease; myopia; optic pits; Stargardt's disease; pars planitis; chronic retinal detachment; hyperviscosity syndromes; toxoplasmosis; trauma and post-laser complications; diseases associated with rubeosis (neovasculariation of the angle); diseases caused by the abnormal proliferation of fibrovascular or fibrous tissue including all forms of proliferative vitreoretinopathy; rheumatoid arthritis; osteoarthritis; ulcerative colitis; Crohn's disease; Bartonellosis; atherosclerosis; Osler-Weber-Rendu disease; hereditary hemorrhagic telangiectasia; pulmonary hemangiomatosis; pre-eclampsia; endometriosis; fibrosis of the liver and of the kidney; developmental abnormalities (organogenesis); skin discolorations (e.g., hemangioma, nevus flammeus, or nevus simplex); wound healing; hypertrophic scars, i.e., keloids; wound granulation; vascular adhesions; cat scratch disease (Rochele ninalia quintosa); ulcers (*Helicobacter pylori*); keratoconjunctivitis; gingivitis; periodontal disease; epulis; cheitis; hepatitis; tonsillitis; obesity; rhinitis; laryngitis; tracheitis; bronchitis; bronchiolitis; pneumonia; interstitial pulmonary fibrosis; pulmonary edema; neurodermitis; thyroiditis; thyroid enlargement; endometriosis; glomerulonephritis; gastritis; inflammatory bone and cartilage destruction; thromboembolic disease; and Buerger's disease. Anti-angiogenesis can be demonstrated by any method known to those skilled in the art.

Anti-angiogenesis agents that can be co-administered with the compounds of the invention include Dalteparin, Suramin, ABT-510, Combretastatin A4 Phosphate, Lenalidomide, LY317615 (Enzastaurin), Soy Isoflavone (Genistein; Soy Protein Isolate), Thalidomide, AMG-706, Anti-VEGF Antibody (Bevacizumab; Avastin™), 171, Bay 43-9006 (Sorafenib tosylate), PI-88, PTK787/ZK 222584 (Vatalanib), SU11248 (Sunitinib malate), VEGF-Trap, XL184, ZD6474, ATN-161, EMD 121974 (Cilenigtide), Celecoxib, Angiostatin, Endostatin, Regranex, Apligraf, Paclitaxel, tetracyclines, clarithromycin, lasix, captopril, aspirin, Vitamin D3 analogs, retinoids, Imiquomod, Interferon alfa2a, Minocycline, copper peptide containing dressings, Lucentis™, ATG002, Pegaptanib Sodium, Tryptophanyl-tRNA synthetase, squalamine lactate, anecortave acetate, AdPEDF, AG-013958, JSM6427, TG100801, Veglin, ascorbic acid ethers (and their analogs), and Pamidronate.

A transition metal chelate, coordinate or complex of a compound of the invention can be prepared by reacting a compound of the invention, or a pharmaceutically acceptable salt thereof, with a transition metal salt. The transition metal salt can be any inorganic or organic salts of the transition metal cation. For example, chloride salt, nitrate salt, sulfate salt, acetate salt and the like can be reacted with a bis[thiohydrazide amide] derivative described herein, or a pharmaceutically acceptable salt thereof, to afford the compounds of the present invention. In one embodiment, the transition metal salt is a copper(II) salt, such as $CuCl_2$. In another embodiment, the transition metal salt is a nickel(II) salt, such as $NiCl_2 \cdot 6H_2O$. Transition metal chelates may also be formed in vivo.

The ratio of the compound and the transition metal cation source used is typically in the range of 0.5 to 2.0 or 0.8-1.2. In one embodiment, the ratio is about 1:1.

Solvents, such as methylene chloride, acetonitrile, acetone, alcohol, such as methanol, ethanol, tetrahydrofuran and water can be used in the reaction of the compound with the transition metal salts. In one embodiment, the solvent is ethanol.

The invention is further defined by reference to the following examples. It will be apparent to those skilled in the art that many modifications, both to materials and methods, may be practiced without departing from the purpose and interest of this invention. The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXEMPLIFICATION

Example 1

Preparation of Compounds of the Invention

Compounds of the invention can be prepared, for example, according to Scheme 1, shown below.

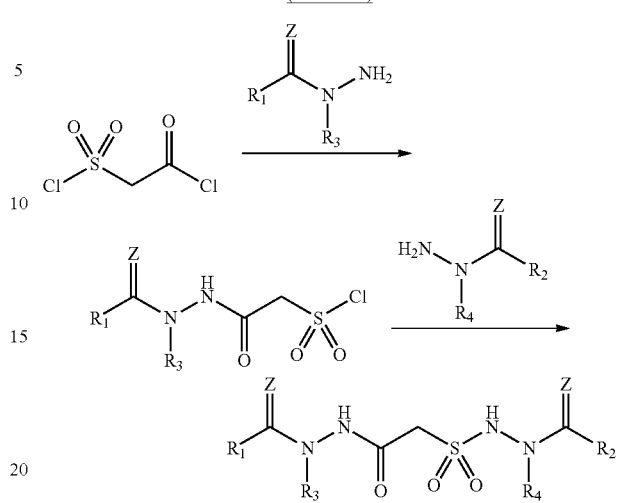

(Scheme 1)

N,N-diethyl-1-methyl-2-(2-(2-methyl-2-(phenylcarbonothioyl)hydrazinyl)-2-oxoethylsulfanyl)hydrazinecarbothioamide (Compound 68)

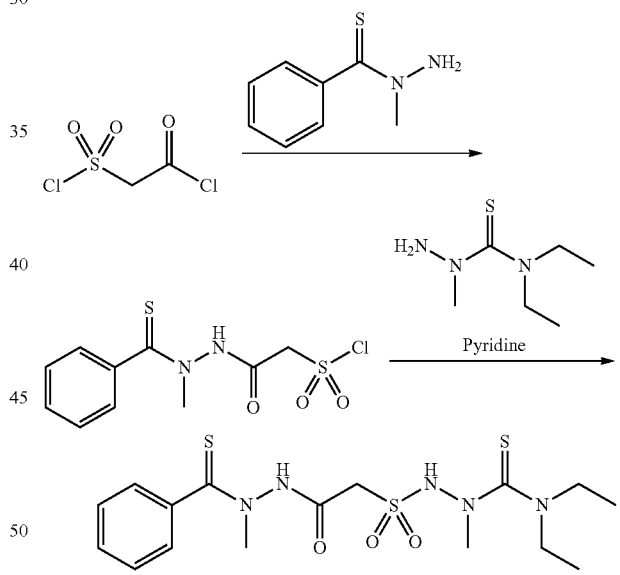

44 mg (0.25 mmol) 2-(chlorosulfonyl)acetyl chloride dissolved in 1 ml dry THF was treated with 42 mg (0.25 mmol) N-methylbenzothiohydrazide dissolved in 0.5 ml THF at 0° C. over 15 min. The reaction was stirred for 15 min and then checked by TLC if the thiohydrazide has completely reacted. Now 40 mg (0.25 mmol) N,N-diethyl-1-methylhydrazinecarbothioamide dissolved in 0.5 ml THF was added and the mixture stirred at 0° C. for 15 min. Then 60 µl (0.75 mmol) pyridine was added and the reaction allowed to warm up to r.t. overnight. The reaction was quenched with 5 ml water, the pH adjusted to 11 and extracted with 5 ml ethyl acetate. The pH was reduced to 4-5 and the aqueous phase extracted 2 times with 5 ml ethyl acetate. The latter extracts were dried over $MgSO_4$ and concentrated. If the purity was not satisfactory (<90%) it was purified on silica with DCM/MeOH (5-20%)/ NH₄OH (1%). ESMS ($C_{16}H_{25}N_5O_3S_3$): calc'd. 431.11. Found: 432.2 [M+H⁺].

HSP70 EC50: 63 nM

N'-methyl-2-(2-methyl-2-(phenylcarbonothioyl)hydrazinyl)-2-oxo-N'-(pyridine-2-carbonothioyl)ethanesulfonohydrazide (Compound 73)

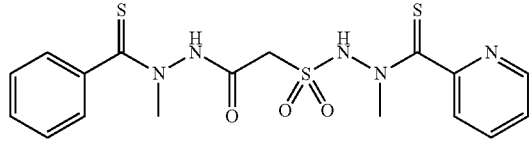 [SMILES: CN(NC(=O)CS(=O)(=O)NN(C)C(=S)c1ccccn1)C(=S)c1ccccc1]

¹H-NMR ($C_2D_6SO$): δ 3.55 (s, 3H), 3.70 (s, 3H), 3.7-3.9 (m, 2H), 7.2-7.5 (m, 9H), 7.8 (m, 1H). ESMS ($C_{17}H_{19}N_5O_3S_3$): calc'd 437.07. Found: 438.1 [M+H⁺].

N'-(cyclopropanecarbonothioyl)-N'-methyl-2-(2-methyl-2-(oxazole-5-carbonothioyl)hydrazinyl)-2-oxoethanesulfonohydrazide (Compound 74)

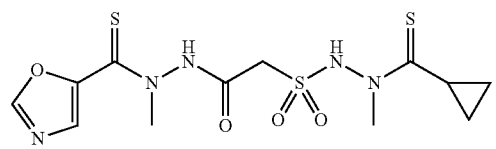 [SMILES: CN(NC(=O)CS(=O)(=O)NN(C)C(=S)C1CC1)C(=S)c1cnco1]

¹H-NMR ($C_2D_6SO$): δ 0.98 (m, 2H), 1.05 (m, 2H), 2.86 (m, 1H), 3.60 (s, 3H), 3.68 (s, 3H), 4.43 (s, 2H), 7.75 (s, 1H), 8.52 (s, 1H). ESMS ($C_{12}H_{17}N_5O_4S_3$): calc'd 391.04. Found: 392.1 [M+H⁺].

HSP70 EC50:301 nM

N'-butyl-2-(2-methyl-2-(phenylcarbonothioyl)hydrazinyl)-2-oxo-N'-(phenylcarbonothioyl)ethanesulfonohydrazide (Compound 75)

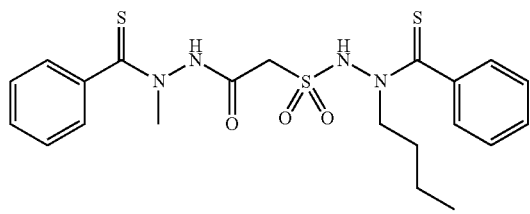 [SMILES: CCCCN(NS(=O)(=O)CC(=O)NN(C)C(=S)c1ccccc1)C(=S)c1ccccc1]

ESMS ($C_{21}H_{26}N_4O_3S_3$): calc'd 478.12. Found: 479.1 [M+H⁺].

HSP70 EC50: 810 nM

2-(2-(cyclopropanecarbonothioyl)-2-methylhydrazinyl)-N'-methyl-2-oxo-N'-(thiazole-5-carbonothioyl)ethanesulfonohydrazide (Compound 76)

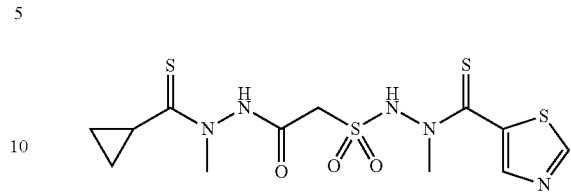

¹H-NMR ($C_2D_6SO$): δ 0.90 (m, 2H), 1.0 (m, 2H), 2.45 (m, 1H), 3.52 (s, 3H), 3.83 (s, 3H), 4.31 (s, 2H), 8.51 (s, 1H), 9.19 (s, 1H). ESMS ($C_{12}H_{17}N_5O_3S_4$): calc'd 407.02. Found: 408.1 [M+H⁺].

HSP70 EC50: 1178 nM

2-(2-(cyclopropanecarbonothioyl)-2-methylhydrazinyl)-N'-methyl-N'-(oxazole-5-carbonothioyl)-2-oxoethanesulfonohydrazide (Compound 77)

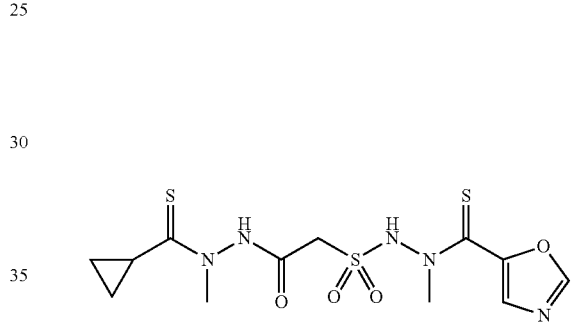

¹H-NMR ($C_2D_6SO$): δ 0.91 (m, 2H), 1.02 (m, 2H), 2.45 (m, 1H), 3.53 (s, 3H), 3.79 (s, 3H), 4.34 (s, 2H), 7.76 (s, 1H), 8.60 (s, 1H). ESMS ($C_{12}H_{17}N_5O_4S_3$): calc'd 391.04. Found: 392.1 [M+H⁺].

HSP70 EC50:967 nM

2-(2-ethyl-2-(pyridine-2-carbonothioyl)hydrazinyl)-N'-methyl-2-oxo-N'-(phenylcarbonothioyl)ethanesulfonohydrazide (Compound 78)

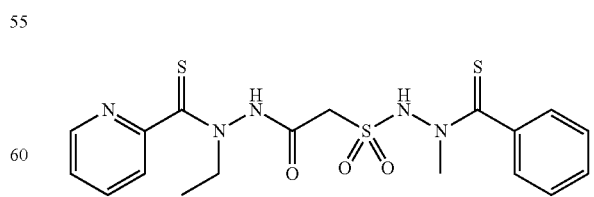

¹H-NMR ($C_2D_6SO$): δ 1.13 (t, ³J=7.1 Hz, 3H), 2.96 (m, 2H), 3.46 (s, 3H), 4.3 (m, 2H), 7.3-7.5 (m, 8H), 7.7 (m, 1H), 8.43 (m, 1H). ESMS ($C_{18}H_{21}N_5O_3S_3$): calc'd 451.08. Found: 452.1 [M+H⁺].

N,N-diethyl-1-methyl-2-(2-(2-methyl-2-(pyrazine-2-carbonothioyl)hydrazinyl)-2-oxoethylsulfonyl)hydrazinecarbothioamide (Compound 70)

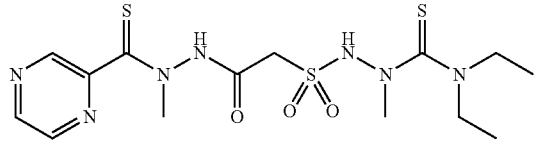 [SMILES: CCN(CC)C(=S)N(C)NS(=O)(=O)CC(=O)NN(C)C(=S)c1cnccn1]

¹H-NMR (CDCl₃): δ 1.26 (t, ³J=7.1 Hz, 6H), 2.88 (s, 3H), 3.6-3.9 (m, 9H), 8.45 (m, 1H), 8.58 (m, 1H), 8.98 (s, 1H). ESMS (C₁₄H₂₃N₇O₃S₃): calc'd 433.10. Found: 434.1 [M+H⁺].

HSP70 EC50: 127 nM 2-(2-(benzo[d][1,3]dioxole-5-carbonothioyl)-2-methylhydrazinyl)-N'-methyl-2-oxo-N'-(phenylcarbonothioyl)ethanesulfonohydrazide (Compound 46)

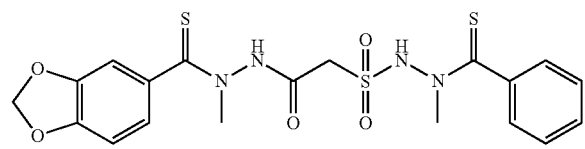 [SMILES: CN(NC(=O)CS(=O)(=O)NN(C)C(=S)c1ccccc1)C(=S)c1ccc2c(c1)OCO2]

¹H-NMR(C₂D₆SO): δ 3.33 (bs, 3H), 3.54 (bs, 3H), 3.74 (m, 2H), 6.02 (s, 2H), 6.75-7.0 (m, 3H), 7.2-7.5 (m, 5H). ESMS (C₁₉H₂₀N₄O₅S₃): calc'd 480.06. Found: 481.1 [M+H⁺].

HSP70 EC50: 63 nM

Ethyl 4-(1-methyl-2-(2-(2-methyl-2-(phenylcarbonothioyl)hydrazinyl)-2-oxoethylsulfonyl)hydrazinocarbonothioyl)furan-3-carboxylate (Compound 46)

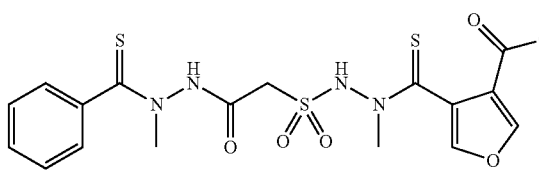

¹H-NMR (C₂D₆SO): δ 1.22 (m, 3H), 3.59 (s, 3H), 3.65 (s, 3H), 3.84 (bs, 2H), 4.18 (m, 2H), 7.2-7.5 (m, 5H), 7.81 (s, 1H), 8.28 (s, 1H). ESMS (C₁₉H₂₂N₄O₆S₃): calc'd 498.07. Found: 499.2 [M+H⁺].

HSP70 EC50: 529 nM

N,N-diethyl-1-methyl-2-(2-(2-methyl-2-(phenylcarbonothioyl)hydrazinylsulfonyl)acetyl)hydrazinecarbothioamide (Compound 69)

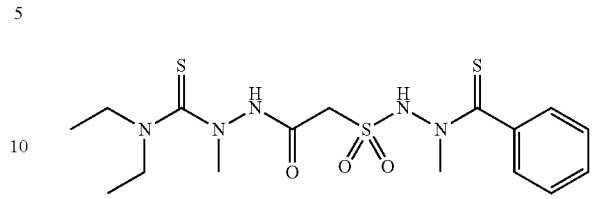

¹H-NMR (CD₃OD): δ 1.17 (m, 6H), 3.05-2.25 (m, 3H), 3.35-3.50 (m, 3 h), 3.55-3.75 (m, 4H), 3.88 (m, 2H), 3.2-3.5 (m, 5H). ESMS (C₁₆H₂₅N₅O₃S₃): calc'd 431.11. Found: 432.2 [M+H⁺].

HSP70 EC50: 85 nM

N,N-diethyl-1-methyl-2-(2-(2-methyl-2-(phenylcarbonothioyl)hydrazinyl)-2-oxoethylsulfonyl)hydrazinecarbothioamide (Compound 68)

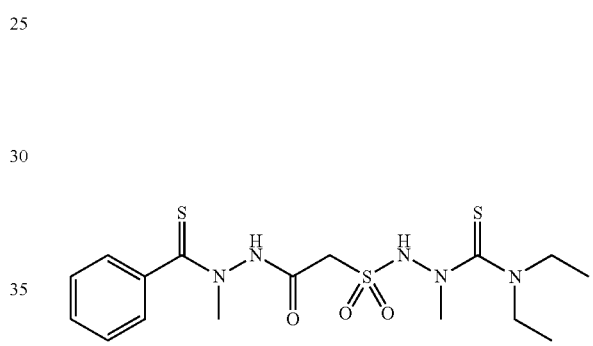

ESMS (C₁₆H₂₅N₅O₃S₃): calc'd 431.11. Found: 432.2 [M+H⁺].

HSP70 EC50: 63 nM

N'-methyl-2-(2-methyl-2-(pyrrolidine-1-carbonothioyl)hydrazinyl)-2-oxo-N'-(phenylcarbonothioyl)ethanesulfonohydrazide (Compound 53)

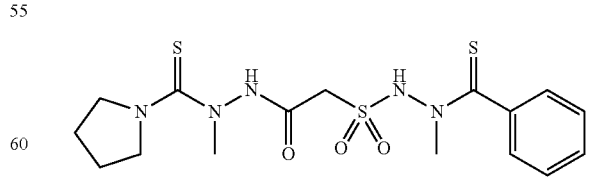

¹H-NMR (CDCl₃): δ 1.92 (m, 4H), 3.26 (m, 4H), 3.56 (s, 3H), 3.67 (s, 3H), 4.27 (bs, 2H), 7.3-7.5 (m, 5H). ESMS (C₁₆H₂₃N₅O₃S₃): calc'd 429.10. Found: 430.1 [M+H⁺].

HSP70 EC50: 102 nM

75

N'-methyl-2-(2-methyl-2-(piperidine-1-carbonothioyl)hydrazinyl)-2-oxo-N'-(phenylcarbonothioyl)ethanesulfonohydrazide (Compound 54)

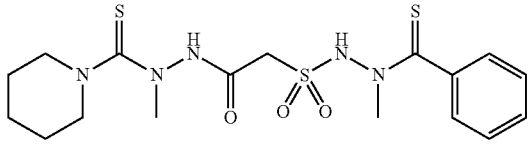 [SMILES: CN(NS(=O)(=O)CC(=O)NN(C)C(=S)N1CCCCC1)C(=S)c1ccccc1]

ESMS ($C_{17}H_{25}N_5O_3S_3$): calc'd 443.11. Found: 444.1 [M+H$^+$].
HSP70 EC50: 108 nM Methyl 1-methyl-2-(2-(2-methyl-2-(phenylcarbonothioyl)hydrazinyl)-2-oxoethylsulfonyl)hydrazinecarbodithioate (Compound 44)

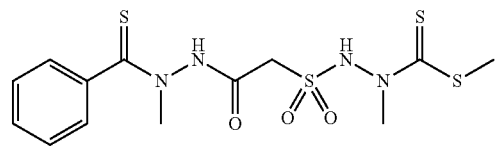 [SMILES: CSC(=S)N(C)NS(=O)(=O)CC(=O)NN(C)C(=S)c1ccccc1]

$^1$H-NMR (CDCl$_3$): δ 2.66 (s, 3H), 3.50 (s, 3H), 3.79 (s, 3H), 4.36 (bs, 2H), 7.3-7.5 (m, 5H). ESMS ($C_{13}H_{18}N_4O_3S_4$): calc'd 406.03. Found: 407.1 [M+H$^+$].
HSP70 EC50: 228 nM N'-methyl-2-(2-methyl-2-(phenylcarbonothioyl)hydrazinyl)-N'-(4-morpholinophenylcarbono-thioyl)-2-oxoethanesulfonohydrazide (Compound 43)

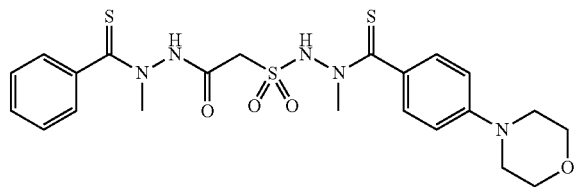 [SMILES: CN(NC(=O)CS(=O)(=O)NN(C)C(=S)c1ccc(N2CCOCC2)cc1)C(=S)c1ccccc1]

ESMS ($C_{22}H_{27}N_5O_4S_3$): calc'd 521.12. Found: 522.2 [M+H$^+$].
HSP70 EC50: 74 nM N'-(benzo[b]thiophene-3-carbonothioyl)-N'-methyl-2-(2-methyl-2-(phenylcarbonothioyl)hydrazinyl)-2-oxoethanesulfonohydrazide (Compound 59)

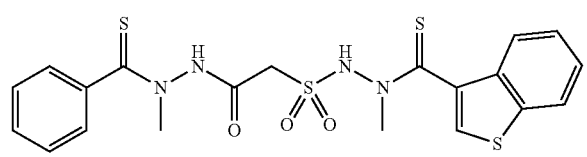 [SMILES: CN(NC(=O)CS(=O)(=O)NN(C)C(=S)c1csc2ccccc12)C(=S)c1ccccc1]

ESMS ($C_{20}H_{20}N_4O_3S_4$): calc'd 492.04. Found: 493.1 [M+H$^+$].
HSP70 EC50: 129 nM

76

N'-methyl-2-(2-methyl-2-(phenylcarbonothioyl)hydrazinyl)-2-oxo-N'-(piperidine-1-carbonothioyl)ethanesulfonohydrazide (Compound 52)

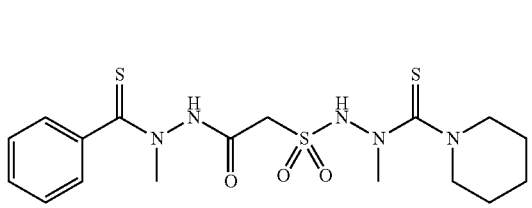 [SMILES: CN(NC(=O)CS(=O)(=O)NN(C)C(=S)N1CCCCC1)C(=S)c1ccccc1]

$^1$H-NMR (CDCl$_3$): δ 1.5-1.9 (m, 6H), 3.00 (m, 2H), 3.17 (m, 2H), 3.77 (m, 3H), 3.84 (m, 3H), 4.05 (m, 2H), 7.28-7.50 (m, 5H). ESMS ($C_{17}H_{25}N_5O_3S_3$): calc'd 443.11. Found: 444.1 [M+H$^+$].
HSP70 EC50: 87 nM N'-ethyl-2-(2-methyl-2-(phenylcarbonothioyl)hydrazinyl)-N-(morpholine-4-carbonothioyl)-2-oxoethanesulfonohydrazide (Compound 50):

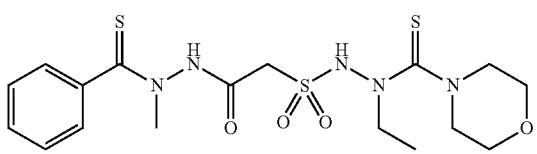 [SMILES: CCN(NS(=O)(=O)CC(=O)NN(C)C(=S)c1ccccc1)C(=S)N1CCOCC1]

ESMS ($C_{17}H_{25}N_5O_4S_3$): calc'd 459.11. Found: 460.1 [M+H$^+$].
HSP70 EC50: 114 nM N'-methyl-2-(2-methyl-2-(phenylcarbonothioyl)hydrazinyl)-2-oxo-N'-(pyrrolidine-1-carbonothioyl)ethanesulfonohydrazide (Compound 51)

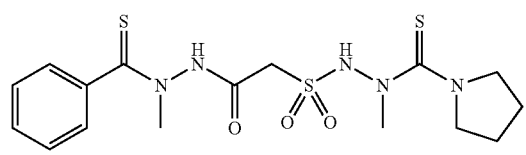 [SMILES: CN(NC(=O)CS(=O)(=O)NN(C)C(=S)N1CCCC1)C(=S)c1ccccc1]

ESMS ($C_{16}H_{23}N_5O_3S_3$): calc'd 429.10. Found: 430.1 [M+H$^+$].
HSP70 EC50: 57 nM

77

N'-methyl-2-(2-methyl-2-(phenylcarbonothioyl)hydrazinyl)-2-oxo-N'-(pyrazine-2-carbonothioyl)ethanesulfonohydrazide (Compound 9)

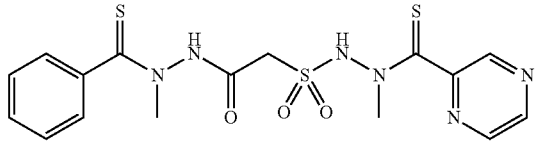 [SMILES: CN(NC(=O)CS(=O)(=O)NN(C)C(=S)c1cnccn1)C(=S)c1ccccc1]

ESMS (C$_{16}$H$_{18}$N$_6$O$_3$S$_3$): calc'd 438.06. Found: 439.1 [M+H$^+$].

HSP70 EC50: 971 nM

N'-(benzo[d][1,3]dioxole-5-carbonothioyl)-N'-methyl-2-(2-methyl-2-(phenylcarbonothioyl)hydrazinyl)-2-oxoethanesulfonohydrazide (Compound 42)

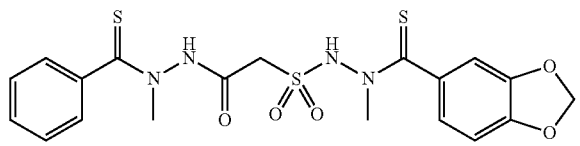 [SMILES: CN(NC(=O)CS(=O)(=O)NN(C)C(=S)c1ccc2c(c1)OCO2)C(=S)c1ccccc1]

$^1$H-NMR (CDCl$_3$): δ 3.50 (s, 3H), 3.65 (s, 3H), 4.36 (s, 2H), 6.03 (s, 2H), 6.81 (d, J=7.9 Hz, 1H), 6.9-7.1 (m, 2H), 7.3-7.5 (m 5H).

ESMS (C$_{19}$H$_{20}$N$_4$O$_5$S$_3$): calc'd 480.06. Found: 481.1 [M+H$^+$].

HSP70 EC50: 56 nM

N'-ethyl-2-(2-methyl-2-(phenylcarbonothioyl)hydrazinyl)-2-oxo-N'-(pyridine-2-carbonothioyl)ethanesulfonohydrazide (Compound 6)

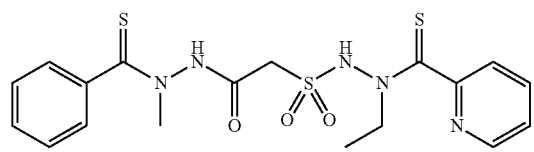 [SMILES: CCN(NS(=O)(=O)CC(=O)NN(C)C(=S)c1ccccc1)C(=S)c1ccccn1]

$^1$H-NMR(C$_2$D$_6$SO): δ 3.56 (s, 3H), 3.63 (s, 3H), 4.31 (bs, 2H), 7.2-7.5 (m, 9H).

ESMS (C$_{18}$H$_{21}$N$_5$O$_3$S$_3$): calc'd 451.08. Found: 452.1 [M+H$^+$].

HSP70 EC50: 25 nM

78

N'-methyl-2-(2-methyl-2-(thiophene-3-carbonothioyl)hydrazinyl)-2-oxo-N'-(phenylcarbonothioyl)ethanesulfonohydrazide (Compound 58)

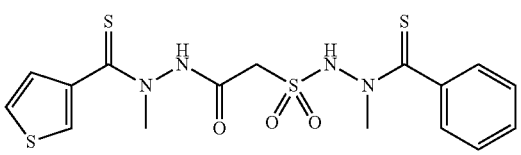 [SMILES: CN(NC(=O)CS(=O)(=O)NN(C)C(=S)c1ccccc1)C(=S)c1ccsc1]

$^1$H-NMR (CDCl$_3$): δ 3.64 (s, 3H), 3.75 (s, 3H), 3.88 (bs, 2H), 6.99 (m, 1H), 7.23-7.52 (m, 5H), 7.58 (s, 1H), 7.67 (m, 1H). ESMS (C$_{16}$H$_{18}$N$_4$O$_3$S$_4$): calc'd 442.03. Found: 443.0 [M+H$^+$].

HSP70 EC50: 77 nM

N'-methyl-2-(2-methyl-2-(phenylcarbonothioyl)hydrazinyl)-2-oxo-N'-(thiophene-3-carbonothioyl)ethanesulfonohydrazide (Compound 57)

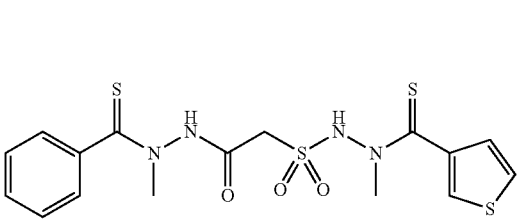 [SMILES: CN(NC(=O)CS(=O)(=O)NN(C)C(=S)c1ccsc1)C(=S)c1ccccc1]

$^1$H-NMR (CDCl$_3$): δ 3.59 (s, 3H), 3.62-3.91 (m, 5H), 7.22-7.28 (m, 6H), 7.43 (m, 2H). ESMS (C$_{16}$H$_{18}$N$_4$O$_3$S$_4$): calc'd 442.03. Found: 443.0 [M+H$^+$].

HSP70 EC50: 77 nM

N'-(3-fluorophenylcarbonothioyl)-2-(2-(3-fluorophenylcarbonothioyl)-2-methylhydrazinyl)-N'-methyl-2-oxoethanesulfonohydrazide (compound 1)

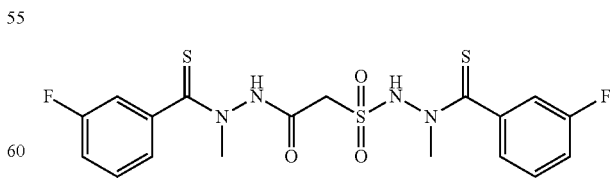

$^1$H-NMR (CDCl$_3$): δ 3.48 (s, 3H), 3.58 (s, 3H), 4.43 (bs, 2H), 9.9-7.3 (m, 6H), 7.38 (m, 2H). ESMS (C$_{18}$H$_{18}$F$_2$N$_4$O$_3$S$_3$): calc'd 472.05. Found: 473.0 [M+H$^+$].

HSP70 EC50: 60 nM

N'-(cyclopropanecarbonothioyl)-2-(2-(cyclopropanecarbonothioyl)-2-methylhydrazinyl)-N'-methyl-2-oxoethanesulfonohydrazide (Compound 28)

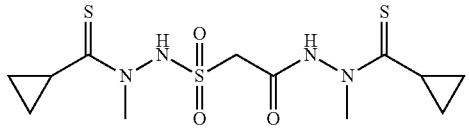 [SMILES: CN(NC(=O)CS(=O)(=O)NN(C)C(=S)C1CC1)C(=S)C1CC1]

$^1$H-NMR (DMSO-d$_6$) (ppm), δ 11.58 (s, 1H), 10.97 (s, 1H), 4.37 (s, 2H), 3.71 (s, 3H), 3.53 (s, 3H), 2.9-2.85 (m, 1H), 2.5-2.48 (m, 1H), 1.15-0.78 (m, 8H); ESMS calc'd for C$_{12}$H$_{20}$N$_4$O$_3$S$_3$: 364.07. Found: 365.1 (M+H)$^+$.

HSP70 EC50: 98 nM

N'-(furan-3-carbonothioyl)-2-(2-(furan-3-carbonothioyl)-2-methylhydrazinyl)-N'-methyl-2-oxoethanesulfonohydrazide (Compound 17):

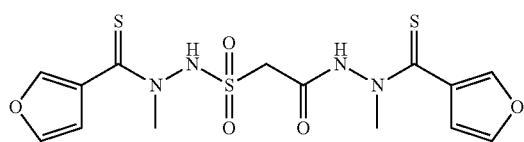 [SMILES: CN(NC(=O)CS(=O)(=O)NN(C)C(=S)c1ccoc1)C(=S)c1ccoc1]

$^1$H-NMR (DMSO-d$_6$) (ppm), δ 11.6 (s, 1H), 10.98 (s, 1H), 8.14 (s, 1H), 8.08 (s, 1H), 7.65 (s, 2H), 6.85 (s, 1H), 6.77 (s, 1H), 4.27 (s, 2H), 3.74 (s, 3H), 3.59 (s, 3H). ESMS calc'd for C$_{14}$H$_{16}$N$_4$O$_5$S$_3$: 416.03. Found: 416.2 (M+H)$^+$.

HSP70 EC50: 127 nM

N'-(furan-2-carbonothioyl)-2-(2-(furan-2-carbonothioyl)-2-methylhydrazinyl)-N'-methyl-2-oxoethanesulfonohydrazide (Compound 18)

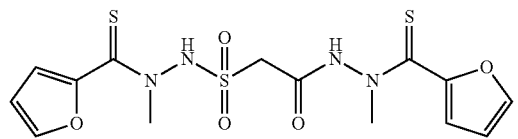 [SMILES: CN(NC(=O)CS(=O)(=O)NN(C)C(=S)c1ccco1)C(=S)c1ccco1]

$^1$H-NMR (DMSO-d$_6$) (ppm), δ 11.61 (s, 1H), 11.0 (s, 1H), 7.92 (s, 1H), 7.84 (s, 1H), 7.2 (s, 1H), 7.15 (s, 1H), 6.65 (s, 1H), 6.60 (s, 1H), 4.26 (s, 2H), 3.74 (s, 3H), 3.58 (s, 3H). ESMS calc'd for C$_{14}$H$_{16}$N$_4$O$_5$S$_3$: 416.03. Found: 416.2 (M+H)$^+$.

HSP70 EC50: 15 nM

N-(cyclopropanecarbonothioyl)-2-(2-(cyclopropanecarbonothioyl)-2-ethylhydrazinyl)-N'-ethyl-2-oxoethanesulfonohydrazide (Compound 29)

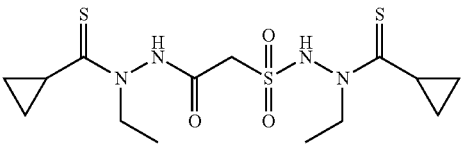 [SMILES: CCN(NC(=O)CS(=O)(=O)NN(CC)C(=S)C1CC1)C(=S)C1CC1]

$^1$H-NMR (DMSO-d$_6$) (ppm), δ 11.49 (s, 1H), 11.05 (s, 1H), 4.27 (s, 2H), 2.6 (m, 2H), 2.24 (m, 2H), 1.30-0.77 (m, 16H); ESMS calc'd for C$_{14}$H$_{24}$N$_4$O$_3$S$_3$: 392.10. Found: 393.2 (M+H)$^+$.

HSP70 EC50: 146 nM

N'-ethyl-2-(2-ethyl-2-(1-methylcyclopropanecarbonothioyl)hydrazinyl)-N'-(1-methylcyclopropanecarbonothioyl)-2-oxoethanesulfonohydrazide (Compound 30)

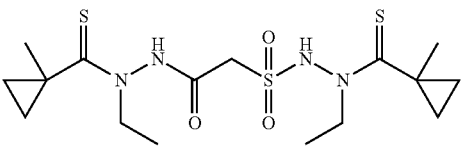 [SMILES: CCN(NC(=O)CS(=O)(=O)NN(CC)C(=S)C1(C)CC1)C(=S)C1(C)CC1]

$^1$H-NMR (DMSO-d$_6$) (ppm), δ 11.5 (s, 1H), 11.1 (s, 1H), 4.26 (s, 2H), 2.55 (m, 2H), 2.24 (m, 2H), 1.35-0.70 (m, 20H); ESMS calc'd for C$_{16}$H$_{28}$N$_4$O$_3$S$_3$: 420.13. Found: 421.2 (M+H)$^+$.

HSP70 EC50: 49 nM

2-(2-(cyclopropanecarbonothioyl)-2-methylhydrazinyl)-N'-methyl-2-oxo-N'-(phenylcarbonothioyl)ethanesulfonohydrazide (Compound 36)

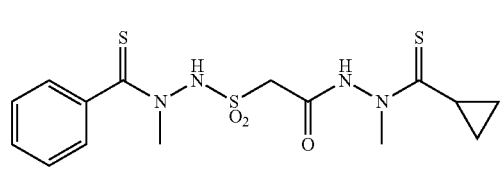 [SMILES: CN(NS(=O)(=O)CC(=O)NN(C)C(=S)C1CC1)C(=S)c1ccccc1]

$^1$H-NMR (CDCl$_3$) δ 10.3 (br, 1H), 9.2 (br, 1H), 7.5 (m, 5H), 4.5 (m, 2H), 3.5-3.8 (m, 6H), 2.4 (m, 1H), 1.6 (m, 4H) ppm; ESMS calc'd for C$_{15}$H$_{20}$N$_4$O$_3$S$_3$: 400.1. Found: 401.1 (M+H$^+$).

HSP70 EC50: 76 nM

81

N'-(cyclopropanecarbonothioyl)-N'-methyl-2-(2-methyl-2-(phenylcarbonothioyl)hydrazinyl)-2-oxoethanesulfonohydrazide (Compound 39)

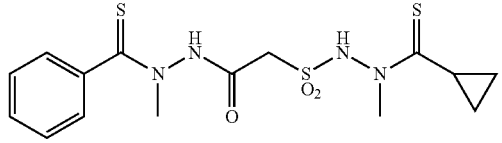 [SMILES: CN(NC(=O)CS(=O)(=O)NN(C)C(=S)C1CC1)C(=S)c1ccccc1]

¹H-NMR (CD₃OD) δ 7.4 (m, 5H), 5.0 (br, 2H), 3.6 (m, 6H), 3.4 (m, 2H), 2.8 (m, 1H), 1.6 (m, 4H) ppm; ESMS calc'd for C₁₅H₂₀N₄O₃S₃: 400.1. Found: 401.1 (M+
HSP70 EC50: 22 nM 2-(2-(cyclobutanecarbonothioyl)-2-methylhydrazinyl)-N'-methyl-2-oxo-N'-(phenylcarbonothioyl)ethanesulfonohydrazide (Compound 40)

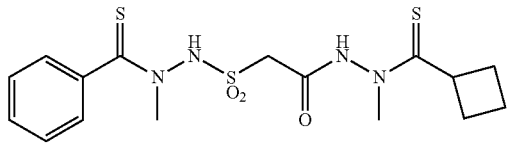 [SMILES: CN(NS(=O)(=O)CC(=O)NN(C)C(=S)C1CCC1)C(=S)c1ccccc1]

ESMS calc'd for C₁₆H₂₂N₄O₃S₃: 414.1. Found: 415.1 (M+H⁺).
HSP70 EC50: 1115 nM

N'-(cyclopropanecarbonothioyl)-N'-methyl-2-(2-methyl-2-(thiazole-5-carbonothioyl)hydrazinyl)-2-oxoethanesulfonohydrazide (Compound 79)

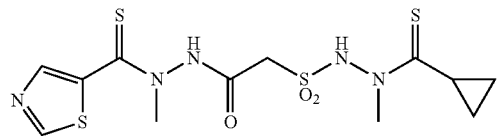

¹H-NMR (CDCl₃) δ 9.8 (br, 2H), 8.80 (s, 1H), 8.15 (s, 1H), 4.2 (m, 2H), 3.85 (s, 3H), 3.75 (s, 3H), 2.1 (m, 1H), 1.6 (m, 4H) ppm; ESMS calc'd for C₁₂H₁₇N₅O₃S₄: 407.0. Found: 408.1 (M+H⁺).

N'-(2-fluorophenylcarbonothioyl)-N'-methyl-2-(2-methyl-2-(phenylcarbonothioyl)hydrazinyl)-2-oxoethanesulfonohydrazide (Compound 80)

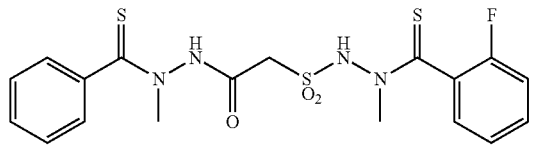 [SMILES: CN(NC(=O)CS(=O)(=O)NN(C)C(=S)c1ccccc1F)C(=S)c1ccccc1]

¹H-NMR (CDCl₃) δ 10.2 (br, 1H), 9.9 (br, 1H), 7.2-7.5 (m, 9H), 4.5 (m, 2H), 3.3-3.6 (m, 6H) ppm; ESMS calc'd for C₁₈H₁₉FN₄O₃S₃: 454.1. Found: 455.1 (M+H⁺).
HSP70 EC50: 139 nM

82

N'-methyl-2-(2-methyl-2-(2-(trifluoromethyl)phenylcarbonothioyl)hydrazinyl)-2-oxo-N'-(phenylcarbonothioyl)ethanesulfonohydrazide (Compound 81)

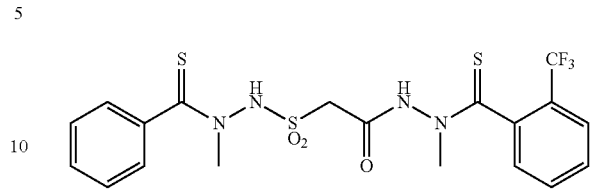

¹H-NMR (Acetone-d₆) δ 10.5 (br, 2H), 7.3-7.8 (m, 9H), 3.0-3.8 (m, 8H) ppm; ESMS calc'd for C₁₉H₁₉F₃N₄O₃S₃: 504.1. Found: 505.1 (M+H⁺).
HSP70 EC50: 354 nM 2-(2-(2-fluorophenylcarbonothioyl)-2-methylhydrazinyl)-N'-methyl-2-oxo-N'-(phenylcarbonothioyl)ethanesulfonohydrazide (Compound 82)

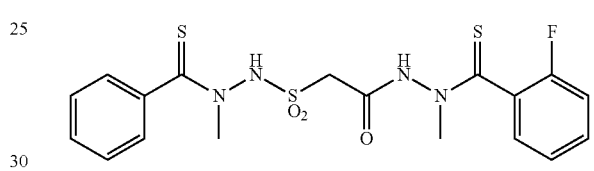

¹H-NMR (Acetone-d₆) δ 10.5 (br, 2H), 7.0-7.8 (m, 9H), 3.3-4.2 (m, 8H) ppm; ESMS calc'd for C₁₈H₁₉FN₄O₃S₃: 454.1. Found: 455.1 (M+H⁺).
HSP70 EC50: 173 nM N'-(cyclobutanecarbonothioyl)-2-(2-(cyclobutanecarbonothioyl)-2-methylhydrazinyl)-N'-methyl-2-oxoethanesulfonohydrazide (Compound 32)

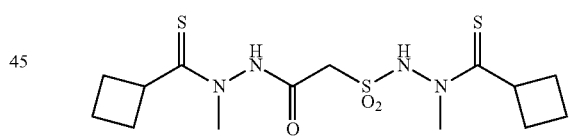

ESMS calc'd for C₁₄H₂₄N₄O₃S₃: 392.1. Found: 393.1 (M+H⁺).
HSP70 EC50: 958 nM

N'-methyl-2-(2-methyl-2-(pyridine-3-carbonothioyl)hydrazinyl)-2-oxo-N'-(phenylcarbonothioyl)ethanesulfonohydrazide (Compound 13)

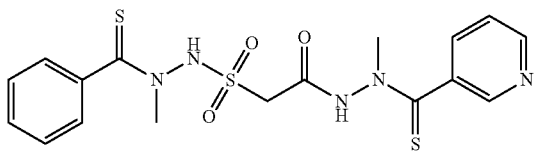 [SMILES: CN(NC(=O)CS(=O)(=O)NN(C)C(=S)c1ccccc1)C(=S)c1cccnc1]

$^1$H-NMR (CD$_3$OD) δ 10.0 (br, 2H), 8.5 (d, 2H, J=5), 7.762 (d, 1H, J=5), 7.3-7.6 (m, 6H), 3.4-3.8 (m, 8H) ppm; ESMS calc'd for C$_{17}$H$_{19}$N$_5$O$_3$S$_3$: 437.1. Found: 438.1 (M+H$^+$).

HSP70 EC50: 202 nM

N'-methyl-2-(2-methyl-2-(phenylcarbonothioyl)hydrazinyl)-2-oxo-N'-(pyridine-3-carbonothioyl)ethanesulfonohydrazide (Compound 10)

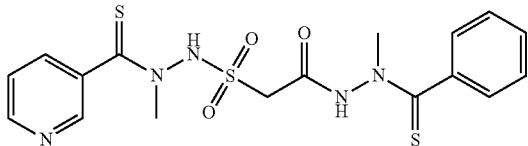 [SMILES: CN(NC(=O)CS(=O)(=O)NN(C)C(=S)c1cccnc1)C(=S)c1ccccc1]

$^1$H-NMR (DMSO-d$_6$) δ 11.4 (br, 1H), 10.8 (br, 1H), 9.48 (s, 2H), 7.7 (d, 1H, J=7), 7.3-7.6 (m, 6H), 3.89 (s, 2H), 3.71 (s, 3H), 3.59 (s, 3H) ppm; ESMS calc'd for C$_{17}$H$_{19}$N$_5$O$_3$S$_3$: 437.1. Found: 438.1 (M+H$^+$).

HSP70 EC50: 180 nM

N'-methyl-2-(2-methyl-2-(pyridine-4-carbonothioyl)hydrazinyl)-2-oxo-N'-(phenylcarbonothioyl)ethanesulfonohydrazide (compound II)

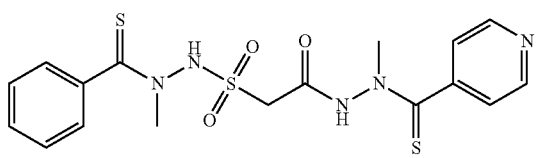 [SMILES: CN(NC(=O)CS(=O)(=O)NN(C)C(=S)c1ccccc1)C(=S)c1ccncc1]

$^1$H-NMR (DMSO-d$_6$) δ 11.4 (br, 1H), 10.7 (br, 1H), 8.5 (d, 2H, J=4), 7.4 (m, 5H), 7.2 (d, 2H, J=4), 35-4.2 (m, 8H) ppm; ESMS calc'd for C$_{17}$H$_{19}$N$_5$O$_3$S$_3$: 437.1. Found: 438.1 (M+H$^+$).

HSP70 EC50: 1029 nM

N'-(cyclopropanecarbonothioyl)-N'-methyl-2-(2-methyl-2-(6-(trifluoromethyl)pyridine-3-carbonothioyl)hydrazinyl)-2-oxoethanesulfonohydrazide (Compound 83)

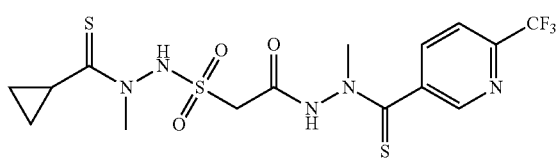 [SMILES: CN(NC(=O)CS(=O)(=O)NN(C)C(=S)C1CC1)C(=S)c1ccc(C(F)(F)F)nc1]

$^1$H-NMR (CD$_3$OD) δ 11.0 (br, 2H), 8.61 (s, 1H), 7.9 (d, 1H, J=11), 7.7 (d, 1H, J=11), 3.74 (s, 3H), 3.71 (s, 3H), 3.3 (m, 2H), 2.8 (m, 1H), 1.0 (m, 4H) ppm; ESMS calc'd for C$_{15}$H$_{18}$F$_3$N$_5$O$_3$S$_3$: 469.1. Found: 470.1 (M+H$^+$).

N'-(cyclopropanecarbonothioyl)-N'-methyl-2-(2-methyl-2-(6-(trifluoromethyl)pyridine-2-carbonothioyl)hydrazinyl)-2-oxoethanesulfonohydrazide (Compound 84)

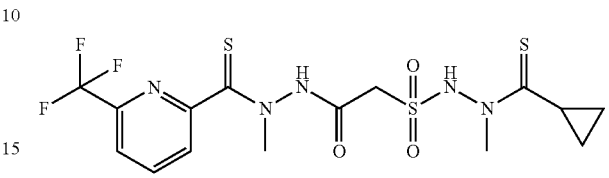

$^1$H-NMR (CD$_3$OD) δ 11.0 (br, 2H), 8.0 (t, 1H, J=10), 7.8 (d, 2H, J=10), 3.74 (s, 3H), 3.70 (s, 3H), 3.3 (m, 2H), 2.8 (m, 1H), 1.0 (m, 4H) ppm; ESMS calc'd for C$_{15}$H$_{18}$F$_3$N$_5$O$_3$S$_3$: 469.1. Found: 470.1 (M+H$^+$).

HSP70 EC50: 144 nM 2-(2-methyl-2-(phenylcarbonothioyl)hydrazinylsulfonyl)-N-(2-thioxopiperidin-1-yl)acetamide (Compound 66)

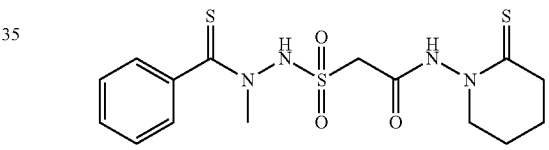

$^1$H NMR (400 MHz, CDCl$_3$) δ (ppm), 10.60-10-42 (m, 2H), 7.48-7.25 (m, 5H), 4.48-1.66 (m, 13H); ESMS calc'd for C$_{15}$H$_{20}$N$_4$O$_3$S$_3$: 400.1. Found: 401.1 (M+H)$^+$.

HSP70 EC50: 48 nM 2-(2-(2-methoxyethanethiol)-2-methylhydrazinyl)-N'-methyl-2-oxo-N'-(phenylcarbonothioyl)ethanesulfonohydrazide (Compound 85)

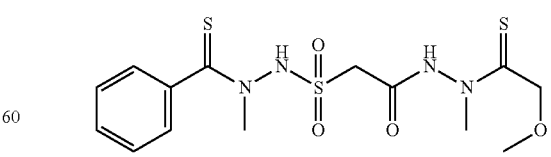

$^1$H NMR (400 MHz, CD$_3$OD) δ (ppm), 10.67-9.72 (m, 2H), 7.61-7.23 (m, 5H), 4.58-3.41 (m, 13H); ESMS calc'd for C$_{14}$H$_{20}$N$_4$O$_4$S$_3$: 404.1. Found: 405.1 (M+H)$^+$.

HSP70 EC50: 60 nM

2-(2-ethanethioyl-2-methylhydrazinyl)-N'-methyl-2-oxo-N'-(phenylcarbonothioyl)ethanesulfonohydrazide (Compound 86)

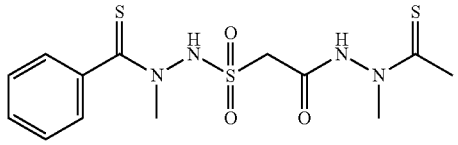 [SMILES: CC(=S)N(C)NC(=O)CS(=O)(=O)NN(C)C(=S)c1ccccc1]

$^1$H NMR (400 MHz, CD$_3$OD) δ (ppm), 10.57-9.22 (m, 2H), 7.63-7.23 (m, 5H), 4.58-2.51 (m, 11H); ESMS calc'd for C$_{13}$H$_{18}$N$_4$O$_3$S$_3$: 374.1. Found: 375.1 (M+H)$^+$.

HSP70 EC50: 21 nM

2-(2-(2-(diethylcarbamothioyl)-2-methylhydrazinyl)-2-oxoethylsulfonyl)-N,N-diethyl-1-methylhydrazinecarbothioamide (Compound 20)

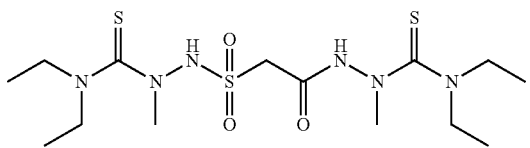 [SMILES: CCN(CC)C(=S)N(C)NC(=O)CS(=O)(=O)NN(C)C(=S)N(CC)CC]

$^1$H-NMR (DMSO-d$_6$) (ppm), δ 10.6 (s, 1H), 9.67 (s 1H), 3.99 (s, 2H), 3.51 (q, 8H), 3.1-3.06 (m, 3H), 1.12-1.10 (m, 12H); ESMS calc'd for C$_{14}$H$_{30}$N$_6$O$_3$S$_3$: 426.15. Found: 427.2 (M+H)$^+$.

HSP70 EC50: 85 nM

2-(2-(2-(cyclopropanecarbonothioyl)-2-methylhydrazinyl)-2-oxoethylsulfonyl)-N,N-diethyl-1-methylhydrazinecarbothioamide (Compound 31)

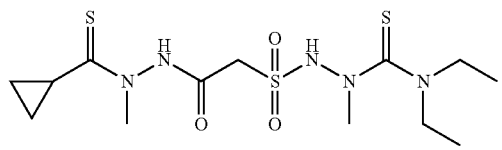 [SMILES: CCN(CC)C(=S)N(C)NS(=O)(=O)CC(=O)NN(C)C(=S)C1CC1]

$^1$H-NMR (DMSO-d$_6$) (ppm), δ 11.4 (s, 1H), 9.48 (s 1H), 4.08 (s, 1H), 3.74-3.62 (m, 4H), 3.52 (s, 3H), 3.08 (s, 3H), 1.18 (t, 6H), 1.02-0.83 (m, 4H); ESMS calc'd for C$_{13}$H$_{25}$N$_5$O$_3$S$_3$: 395.11. Found: 396.2 (M+H)$^+$.

HSP70 EC50: 174 nM

O-ethyl 2-(2-(2-(cyclopropanecarbonothioyl)-2-methylhydrazinyl)-2-oxoethylsulfonyl)-1-methylhydrazinecarbothioate (Compound 33)

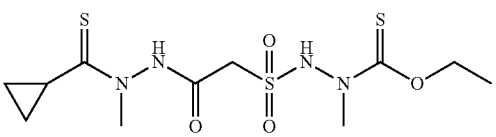 [SMILES: CCOC(=S)N(C)NS(=O)(=O)CC(=O)NN(C)C(=S)C1CC1]

$^1$H-NMR (DMSO-d$_6$) (ppm), δ 11.46 (s, 1H), 10.67 (s 1H), 4.45 (m, 2H), 4.19 (s, 2H), 3.56 (s, 6H), 2.45 (m, 2H), 1.35 (t, 3H), 1.02-0.85 (m, 4H); ESMS calc'd for C$_{11}$H$_{20}$N$_4$O$_4$S$_3$: 368.06. Found: 369.1 (M+H)$^+$.

HSP70 EC50: 143 nM

2-(2-(cyclopropanecarbonothioyl)-2-methylhydrazinyl)-N'-ethyl-2-oxo-N'-(pyrazine-2-carbonothioyl)ethanesulfonohydrazide (Compound 35)

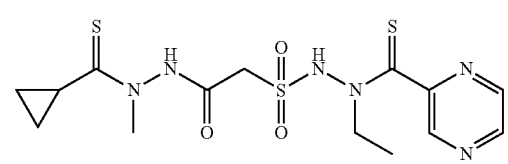 [SMILES: CCN(NS(=O)(=O)CC(=O)NN(C)C(=S)C1CC1)C(=S)c1cnccn1]

$^1$H-NMR (DMSO-d$_6$) (ppm), δ 11.52 (s, 1H), 11.3 (s 1H), 8.9-8.5 (m, 3H), 4.20 (s, 2H), 3.50-3.4 (m, 5H), 2.45 (m, 1H), 1.37-0.75 (m, 7H); ESMS calc'd for C$_{14}$H$_{20}$N$_6$O$_3$S$_3$: 416.08. Found: 416.2 (M+H)$^+$.

HSP70 EC50: 1023 nM

2-(2-(cyclopropanecarbonothioyl)-2-methylhydrazinyl)-N'-methyl-2-oxo-N'-(pyrrolidine-1-carbonothioyl)ethanesulfonohydrazide (Compound 37)

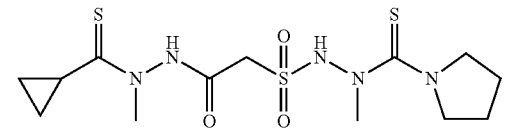 [SMILES: CN(NC(=O)CS(=O)(=O)NN(C)C(=S)N1CCCC1)C(=S)C1CC1]

$^1$H-NMR (DMSO-d$_6$) (ppm), δ 11.48 (s, 1H), 9.81 (s 1H), 4.12 (s, 2H), 3.62-3.54 (m, 4H), 3.51 (s, 3H), 3.25 (s, 3H), 1.93-1.79 (m, 4H), 1.04-0.84 (m, 5H); ESMS calc'd for C$_{13}$H$_{23}$N$_5$O$_3$S$_3$: 393.10. Found: 394.2 (M+H)$^+$.

HSP70 EC50: 93 nM methyl 2-(2-(2-(cyclopropanecarbonothioyl)-2-methylhydrazinyl)-2-oxoethylsulfonyl)-1-methylhydrazinecarbodithioate (Compound 37)

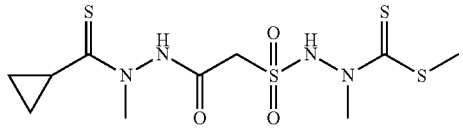 [SMILES: CSC(=S)N(C)NS(=O)(=O)CC(=O)NN(C)C(=S)C1CC1]

$^1$H-NMR (DMSO-d$_6$) (ppm), δ 11.53 (s, 1H), 10.92 (s 1H), 4.37 (m, 2H), 3.7 (s, 3H), 3.52 (s, 3H), 2.45 (s, 3H), 1.07-0.83 (m, 5H); ESMS calc'd for C$_{10}$H$_{18}$N$_4$O$_3$S$_4$: 370.03. Found: 371.1 (M+H)$^+$.

HSP70 EC50: 369 nM

N'-(cyclopropanecarbonothioyl)-3-(2-(cyclopropanecarbonothioyl)-2-methylhydrazinyl)-1-(dimethylamino)-N'-methyl-3-oxoprop-1-ene-2-sulfonohydrazide (Compound 88) and 1-amino-N'-(cyclopropanecarbonothioyl)-3-(2-(cyclopropanecarbonothioyl)-2-methylhydrazinyl)-N'-methyl-3-oxoprop-1-ene-2-sulfonohydrazide (Compound 87)

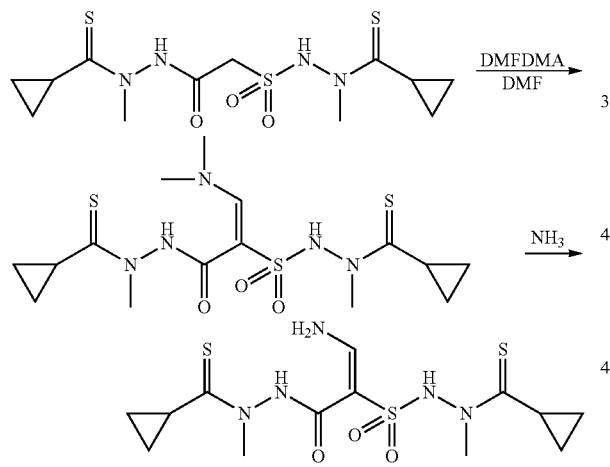

To the solution of compound 28 (2 mmol, 728 mg) in 5 mL of DMF was added N,N-dimethylformamide dimethyl acetal (3 mmol, 357 mg). The reaction was stirred at room temperature for 20 minutes, heated to 60° C. for 1 hour. The solvent was removed under reduced pressure and the residue was purified by the column chromatography on silica gel to give the title compound as a mixture of cis/trans isomers.

To a solution of compound 88 (0.1 mmol, 41.9 mg) in 5 mL of THF was added 0.2 mL of 30% ammonia in MeOH. The reaction mixture was stirred at room temperature for 3 hours. After the completion of the reaction, the reaction mixture was diluted with CH$_2$Cl$_2$ and organic phase was washed with water and brine, dried (Na$_2$SO$_4$), filtered, and concentrated. The residue was purified by the column chromatography on silica gel to give product compound 87 as a mixture of cis/trans isomers.

N'-(cyclopropanecarbonothioyl)-3-(2-(cyclopropanecarbonothioyl)-2-methylhydrazinyl)-1-(dimethylamino)-N'-methyl-3-oxoprop-1-ene-2-sulfonohydrazide (Compound 88)

HSP70 EC50: 209 nM

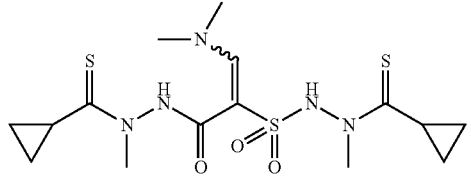 [SMILES: CN(C)C=C(C(=O)NN(C)C(=S)C1CC1)S(=O)(=O)NN(C)C(=S)C1CC1]

ESMS calc'd for C$_{15}$H$_{25}$N$_5$O$_3$S$_3$ 419.11. Found: 420.2 (M+H)$^+$ $^1$H NMR (400 MHz, CDCl$_3$) δ 9.89-7.41 (m), 3.82-3.00 (m, 12H), 1.37-0.86 (m, 10H),

1-amino-N'-(cyclopropanecarbonothioyl)-3-(2-(cyclopropanecarbonothioyl)-2-methyl-hydrazinyl)-N'-methyl-3-oxoprop-1-ene-2-sulfonohydrazide (Compound 87)

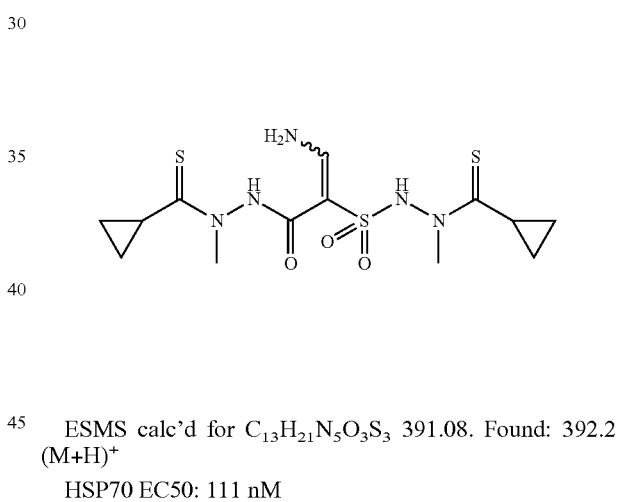

ESMS calc'd for C$_{13}$H$_{21}$N$_5$O$_3$S$_3$ 391.08. Found: 392.2 (M+H)$^+$

HSP70 EC50: 111 nM

N'-(cyclopropanecarbonothioyl)-3-(2-(cyclopropanecarbonothioyl)-2-methylhydrazinyl)-N'-methyl-1-(methylamino)-3-oxoprop-1-ene-2-sulfonohydrazide (Compound 89)

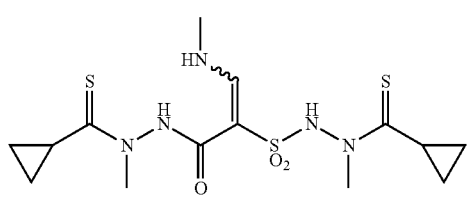

ESMS calc'd for C$_{14}$H$_{23}$N$_5$O$_3$S$_3$: 405.10. Found: 406.1

HSP70 EC50: 201 nM

N'-(cyclopropanecarbonothioyl)-3-(2-(cyclopropanecarbonothioyl)-2-methylhydrazinyl)-1-(cyclopropylamino)-N'-methyl-3-oxoprop-1-ene-2-sulfonohydrazide (Compound 90)

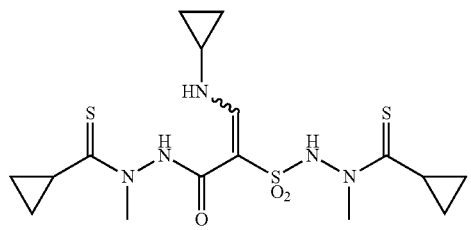 [SMILES: CN(NC(=O)C(=CNC1CC1)S(=O)(=O)NN(C)C(=S)C1CC1)C(=S)C1CC1]

ESMS calc'd for $C_{16}H_{25}N_5O_3S_3$: 431.11. Found: 432.2
HSP70 EC50: 227 nM N'-(cyclopropanecarbonothioyl)-3-(2-(cyclopropanecarbonothioyl)-2-methylhydrazinyl)-1-(isopropylamino)-N'-methyl-3-oxoprop-1-ene-2-sulfonohydrazide (Compound 91)

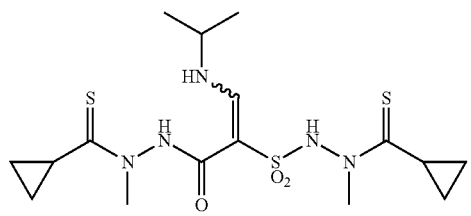 [SMILES: CC(C)NC=C(C(=O)NN(C)C(=S)C1CC1)S(=O)(=O)NN(C)C(=S)C1CC1]

ESMS calc'd for $C_{16}H_{27}N_5O_3S_3$: 433.13. Found: 434.2 $(M+H)^+$
HSP70 EC50: 229 nM Example 2

Hsp70 Activity Essay

Each well was plated with MDA435 cells using DMEM 10% FBS Phenol-red free medium 2.5 k/well and incubated in a 37° C./5% $CO_2$ incubator for a minimum of 6 hours to obtain good cell adherence.

Dilutions of each test compound were prepared in DMSO and DMEM 10% FBS Phenol-red free medium. The final concentration in each well was 1250 nM, 125 nM, 12.5 nM or 1.25 nM of test compound and 0.25% DMSO. 0.25% DMSO was used as a negative control. Lysis buffer (any lysis buffer suitable for use in the Assay Designs kit, e.g., such as that described in the kit instructions) was then added (amount used is one quarter of the volume already present in each plate) and the mixtures were then shaken for 10 minutes.

150 µL of "Can Get Signal" Immunoreaction Enhancer Solution (Solution 1 for primary antibody, TOYOBO, Catalogue No. NKB-101) were added to each of a series of ELISA plates. The ELISA plates were obtained from the HSP70 ELISA Kit (catalogue number EKS-700B) purchased from Assay Designs (Ann Arbor, Mich.). After the cells were lysed, 50 µL of lysate were taken from each well and added to an ELISA plate, resulting in a 4 fold dilution of the lysate (50 µL of lysate and 150 µL of Can Get Signal solution). The plates were covered with adhesive tape and incubated overnight at 4° C.;

In the morning, the liquid was aspirated from all wells and 400 µL of Washing Buffer made from 20× concentrate provided in the ELISA Kit and distilled water were added and then removed by aspiration. The addition of Washing Buffer and aspiration was repeated four times. After the fourth wash, the plate were inverted to a paper towel and carefully patted dry. 100 µL of HSP70 antibody provided in ELISA Kit were added to each well. Each well was covered with adhesive tape and incubated for one hour at room temperature. Washing Buffer was then added followed by removal with aspiration. The addition of Washing Buffer and aspiration was repeated four times, after which the plates were inverted and patted dry. 100 µL of HSP70 conjugate (provided in the ELISA Kit) were added to the wells. Each well was then covered with adhesive tape and incubated for one hour at room temperature. Washing Buffer was then added followed by removal with aspiration. The addition of Washing Buffer and aspiration was repeated four times, after which the plates were inverted and patted dry.

100 µL of the TMB Substrate (obtained from the ELISA Kit) were added to the wells (color development was visible in 1 minute). The wells were incubated until saturated color development (usually 5-15 minutes). Stop Solution 2 (provided in the ELISA Kit) was added in the same order TMB Substrate was added. The OD450 was then obtained using a plate reader. The EC50 for the compounds was calculated using $N^{t1},N^{t3}$-dimethyl-$N^{t1},N^{t3}$-di(phenylcarbonothioyl)malonohydrazide on the same plate as a control (concentration that increases HSP70 to 50% of maximum increase by $N^{t1}$, $N^{t3}$-dimethyl-$N^{t1},N^{t3}$-di(phenylcarbonothioyl)malonohydrazide). The EC50 for each of the compounds tested is shown in example 1.

Examples 3-7

Heat shock proteins (Hsp) are induced under a variety of stress conditions and bind to other proteins to prevent their denaturation. Hsps can protect the cell from apoptotic death. Agents that induce the production of Hsp70 can have protective activity against a wide range of insults, and may have particular utility in neurological disorders. The neuroprotectant activity of Hsp70 inducing compounds of the invention can be assessed in a variety of animal neurological disease models. Specifically, animal models of stroke, amyotrophic lateral sclerosis, Huntington's disease, Parkinson's disease, and Alzheimer's disease are appropriate settings for testing efficacy. Some example animal models are provided below.

Example 3

Cerebral Ischemia (Stroke)

The benefit of the disclosed treatment with Hsp70 inducing compounds of the invention can be assessed in rodent models of stroke. For example the stroke model described in Longa, et al. (Longa, E. Z., Weinstein, P. R., Carlson, S., and Cummins, R. (1989) Reversible middle cerebral artery occlusion without craniotomy in rats. *Stroke* 20:84-91) can be utilized.

Rats are anesthetized with ketamine, and then infarction is induced by extracranial vascular occlusion. A 4-0 nylon intraluminal suture is placed into the cervical internal carotid artery and is advanced intracranially to block blood flow into the middle cerebral artery. Collateral blood flow is reduced by interrupting all branches of the external carotid artery and all extracranial branches of the internal carotid artery. A compounds of the invention can be dosed just prior to or just after induction of the infarction. The dose may be, for example, 10 to 100 mg/kg body weight administered once per week, three times per week, or daily by any conventional mode of administration, e.g., orally or intravenously. Neurologic deficit, mortality, gross pathology (infarction size), and histochemical staining can be analyzed to assess efficacy of the compounds. Since this is a very acute model, and death is often observed by three days after infarction, the modeling may consist of only a single administration of drug.

Example 4

Familial Amyotrophic Lateral Sclerosis (ALS)

The efficacy of compounds of the invention in the treatment of ALS can be modeled using the SOD1 transgenic mouse model (Gurney, M. E., Pu, H., Chiu, A. Y., Dal Canto, M. C., Polchow, C. Y., Alexander, D. D., Caliendo, J., Hentati, A., Kwon, Y. W., and Deng, H. X. (1994) Motor neuron degeneration in mice that express a human CuZn superoxide dismutase mutation. *Science* 264:1772-1775). Mutations of human CuZn superoxide dismutase (SOD) are found in patients with familial ALS. Expression of the human SOD gene containing a substitution of glycine-to-alanine at amino acid 93 leads to motor neuron disease in transgenic mice. As a result of motor neuron loss from the spinal cord, the mice became paralyzed and die by 5 to 6 months of age.

To test the efficacy of the Hsp70 inducing compounds of the invention, transgenic mice having the SOD1 mutation (SOD1$^{G93A}$) are treated with the compounds, and the effect on disease is monitored. The symptoms are clinically apparent in these animals at 2.5 to 3 months of age. Compounds can be dosed starting at this time. The dose may be, for example, 10 to 100 mg/kg body weight administered once per week or three times per week by the oral or intravenous route. Endpoints include functional impairment of motor function as well as histological changes. The latter endpoints include histopathology of brain and spinal cord assessing degeneration of motor neurons and the appearance of neurofilament-rich inclusions in spinal motor neurons. If long-term administration is performed, the impact on mouse survival can be assessed.

Example 5

Huntington's Disease (HD)

A transgenic mouse model of HD exists, allowing the testing of Hsp70 inducing compounds of the invention for efficacy in this disease setting (Mangiarini, L., Sathasivam, K., Seller, M., Cozens, B., Harper, A., Hetherington, C., Lawton, M., Trottier, Y., Lehrach, H., Davies, S. W., and Bates, G. P. (1996) Exon 1 of the HD gene with an expanded CAG repeat is sufficient to cause a progressive neurological phenotype in transgenic mice. *Cell* 87:493-506; Carter, R. J., Lione, L. A., Humby, T., Mangiarini, L., Mahal, A., Bates, G. P., Dunnett, S. B., and Morton, A. J. (1999) Characterization of progressive motor deficits in mice transgenic for the human Huntington's disease mutation. *J. Neuroscience* 19:3248-3257). HD is caused by a CAG/polyglutamine repeat expansion. These transgenic mice (R6/2 transgenics) have the 5' end of the human HD gene with (CAG)115-(CAG)150 repeat expansions. The mice exhibit progressive neurological pathologies similar to HD, including abnormal and involuntary movements, tremors, and epileptic seizures.

These transgenic mice show overt behavioral changes at approximately 8 weeks of age. As early as 5 to 6 weeks of age, they display more subtle deficiencies in motor skills. Hsp70-inducing compounds of the invention can be administered by intravenous or oral administration at doses of 10-100 mg per kg of body weight starting at various times (for example, at 5 to 6 weeks of age). Compounds can be given on multiple different dosing schedules (e.g., once per week versus three times per week). Performance on one or more rodent motor tests such as swimming tank, beam walking, rotarod apparatus, and footprint test (see Carter, et al., 1999) can be performed to assess the activity of the compounds in preventing loss of neurological function in HD mice.

Example 6

Parkinson's Disease (PD)

There are two widely employed models of PD in which disease is induced by chemical treatment. These are the 6-OHDA (Zigmond, M. J. and Stricker, E. M. (1984) Parkinson's disease: studies with an animal model. *Life Sci.* 35:5-18; Sauer, H. and Oertel, W. H. (1994) Progressive degeneration of nigrostriatal dopamine neurons following intrastriatal terminal lesions with 6-hydroxydopamine: a combined retrograde tracing and immunocytochemical study in the rat. *Neuroscience* 59:401-415) and the MPTP (Langston, J. W., Form, L. S., Rebert, C. S., and Irwin, I. (1984) Selective nigral toxicity after systemic administration of 1-methyl-4-phenyl-1,2,5,6-tetrahydropyrine (MPTP) in the squirrel monkey. *Brain Res.* 292:390-4) models. An example of a test of Hsp70 inducing compounds of the invention using the 6-OHDA is described.

Young adult male rats are injected with Fluoro-Gold (FG) by stereotactic injection into the striatum in the brain in order to facilitate visualization of the neurons in the substantia nigra, the site of PD. Under anesthesia, 0.2 μl of a 4% solution of FG is administered by stereotactic injection (1 mm anterior from bregma, 3 mm lateral, and 4.5 mm ventral from dura into both striata). One week after FG injection, the rats receive a stereotactic injection of 6-OHDA (20 μg dissolved in 4 μl saline; Sigma) into the striatum on one side of the brain, at the same coordinates as the FG injection. Hsp70 inducing compounds of the invention can be administered by intravenous or oral administration at doses of 10-100 mg per kg of body weight. The compounds can be given at the time of 6-OHDA injection or some time (2-4 weeks, for example) subsequent to 6-OHDA treatment. Rats are sacrificed 8 and 16 weeks after 6-OHDA injection. The endpoints of this model are 1) behavioral changes as monitored in-life at various times by assessment of turning (rotational) behavior using classical neurological read-out, and 2) the brain is removed after sacrifice, thin sections are made using a cryostat, and immunohistochemistry is performed as described in Zigmond and Stricker (1984). Efficacy of the Hsp70 inducing compounds of the invention is demonstrated by a decrease in rotational behavior as well as a reduction in the loss of nigral dopaminergic neurons.

Example 7

Alzheimer's Disease (AD)

There are several transgenic mouse models of AD. One such model that is widely used to test the efficacy of drugs in AD was described by Holcomb, et al. (Holcomb, L., Gordon, M. N., McGowan, E., Yu, X., Benkovic, S., Jantzen, P., Wright, K., Saad, I., Mueller, R., Morgan, D., Sanders, S., Zehr, C., O'Campo, K., Hardy, J., Prada, C. M., Eckman, C., Younkin, S., Hsiao, K., and Duff, K. (1998) Accelerated Alzheimer-type phenotype in transgenic mice carrying both mutant amyloid precursor protein and presenilin 1 transgenes. *Nature Medicine* 4:97-100). This model contains two different genes associated with AD. One is a mutation in the amyloid precursor protein (APP). The mutant APP (K670N, M671L) transgenic line, Tg2576, has elevated amyloid beta-protein levels at an early age, and, later, develops extracellular AD-type A beta deposits in the brain. The other gene is a mutated presenilin-1 (PSI) gene. The doubly transgenic progeny from a cross between Tg2576 and the PS1 mutant PS1M146L transgenic line develop large numbers of fibrillar A beta deposits in cerebral cortex and hippocampus far earlier than their singly transgenic Tg2576 mice.

Hsp70 inducing compounds of the invention can be dosed in mice at various times. The age of mice at the start of drug dosing may be varied. For example, a treatment starting time may be at 3 months of age, a time at which the brain deposits are first detectable. The dose may be, for example, 10 to 100 mg/kg body weight administered once per week or three times per week by the oral or intravenous route. The effect of drug treatment can be assessed by measuring AD-type deposits in the brain as well as by assessing function of the mice in a maze test.

Example 8

Measurement of Heat Shock Protein 70 (Hsp70)

Plasma Hsp70 can be measured by a sandwich ELISA kit (Stressgen Bioreagents Victoria, British Columbia, CANADA) according to a modified protocol in house. In brief, Hsp70 in plasma specimens and serial concentrations of Hsp70 standard are captured onto 96-well plate on which anti-Hsp70 antibody was coated. Then captured Hsp70 is detected with a biotinylated anti-Hsp70 antibody followed by incubation with europium-conjugated streptavidin. After each incubation unbound materials are removed by washing. Finally, antibody-Hsp70 complex was measured by time resolved fluorometry of europium. Concentration of Hsp70 is calculated from a standard curve.

Example 9

Inhibition of HUVEC Cell Migration

To examine if the compounds of the invention affect endothelial cell function, an in vitro human umbilical vein endothelial cell (HUVEC) migration assay is performed in the presence of a compound of the invention. HUVEC cells (passage number 4) are cultured on 12-well plates and time-lapse imaging is performed with the live cell imaging system on an inverted microscope supplied with 6-7% $CO_2$. The temperature is kept at 37° C. Images are taken every 30 minutes using the 2× objective for up to 106 hr or every 60 seconds using the 20× objective for 30 min. Confluent HUVEC cultures are scraped similarly to make a blank area, followed by culturing in HUVEC medium for 15 hr without treatment. The migration areas, which are imaged as time-lapse sequences for each well, are used as a basis to standardize/correct migration rates. Then, migration of cells under different treatments is imaged at the same time to generate time-lapse image sequences for each well. Time-lapse movies are further analyzed by measuring areas that are covered by migrating cells. During experiments, HUVEC cells are activated by the presence of VEGF and basic FGF. Compounds of the invention (e.g. 100 nM and 1 μM) are expected to completely block migration of HUVEC cells to the blank area, indicating that compounds of the invention possesses potent inhibitory effect on the migration of activated HUVEC cell in vitro induced by VEGF and basic FGF.

It is also possible to track HUVEC behavior during above treatments. It is expected that HUVEC cells will begin to shrink after 24 hr treatment with compounds of the invention.

Example 10

Enhanced VE-Cadherin Junctions of HUVEC Cells

An immunofluorescence study is performed by using anti-VE-cadherin antibodies to examine VE-cadherin junctions between HUVEC cells. HUVEC cells are treated with DMSO or a compound of the invention (e.g. 10, 100 and 1000 nM) for 24 hrs and fixed for immunostaining. DMSO concentration is 1:100 for all treatments. To boost the immunofluorescence signal, cells are stained with a mixture of 2 polyclonal anti-human VE-cadherin Abs followed by staining with a mixture of fluorescent secondary antibodies. It is expected that with compounds of the invention, VE-cadherin staining will be extremely strong in cell-cell junction regions, but not the non-contacted regions compared to that in DMSO treated cultures. Compounds of the invention are expected to enhance the assembly of cell-cell junctions of activated human endothelial cells, likely through induction of the accumulation of VE-cadherin molecules at the junctions. This effect could result in limited motility of the cells and reducing permeability of the endothelium, thus contributing to the cell migration inhibition and the potential anti-angiogenesis effect of compounds of the invention.

While this invention has been particularly shown and described with references to example embodiments thereof, it will be understood by those skilled in the art that various changes in form and details may be made therein without departing from the scope of the invention encompassed by the appended claims.

What is claimed is:

1. A compound represented by the following structural formula:

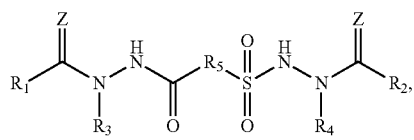

or a pharmaceutically acceptable salt or a transition metal chelate, coordinate or complex thereof or a transition metal chelate, coordinate or complex of a deprotonated form of the compound, wherein:
each Z is S;
$R_1$ and $R_2$ are different and are each selected from the group consisting of an optionally substituted alkyl; an optionally substituted alkenyl; an optionally substituted alkynyl; an optionally substituted cycloalkyl; an optionally substituted cycloalkenyl; an optionally substituted heterocyclic group wherein the heterocyclic group is bonded to the thiocarbonyl carbon via a carbon-carbon linkage; an optionally substituted phenyl; an optionally substituted bicyclic aryl; an optionally substituted five to seven-membered monocyclic heteroaryl; an optionally substituted nine to fourteen-membered bicyclic heteroaryl wherein the heteroaryl group is bonded to the thiocarbonyl carbon via a carbon-carbon linkage; —NR$_{12}$R$_{13}$; —OR$_{14}$; —SR$_{14}$ and —S(O)$_p$R$_{15}$;

R$_3$ and R$_4$ are each independently selected from the group consisting of hydrogen, an optionally substituted alkyl, an optionally substituted alkenyl, an optionally substituted alkynyl, an optionally substituted cycloalkyl, an optionally substituted cycloalkenyl, an optionally substituted heterocyclic group, and an optionally substituted five to six-membered aryl or heteroaryl group; or R$_1$ and R$_3$ and/or R$_2$ and R$_4$, taken together with the atoms to which they are attached, form an optionally substituted heterocyclic group or an optionally substituted heteroaryl group;

R$_5$ is —CR$_6$R$_7$—, —C(=CHR$_8$)— or —C(=NR$_8$)—;

R$_6$ and R$_7$ are both —H or an optionally substituted lower alkyl;

R$_8$ is selected from the group consisting of —OH, an alkyl, an alkenyl, an alkynyl, an alkoxy, an alkenoxy, an alkynoxy, a hydroxyalkyl, a hydroxyalkenyl, a hydroxyalkynyl, a haloalkyl, a haloalkenyl, a haloalkynyl, an optionally substituted phenyl, an optionally substituted bicyclic aryl, an optionally substituted five to six-membered monocyclic heteroaryl, an optionally substituted nine to fourteen-membered bicyclic heteroaryl, an optionally substituted cycloalkyl or an optionally substituted heterocyclic group; —NR$_{10}$R$_{11}$, and —COR$_9$;

R$_9$ is an optionally substituted phenyl, an optionally substituted bicyclic aryl, an optionally substituted five or six-membered monocyclic heteroaryl, an optionally substituted nine to fourteen-membered bicyclic heteroaryl, an optionally substituted alkyl, an optionally substituted cycloalkyl or an optionally substituted heterocyclic group;

R$_{10}$ and R$_{11}$ are each independently selected from the group consisting of —H, —OH, amino, (di)alkylamino, an alkyl, an alkenyl, an alkynyl, an alkoxy, an alkenoxy, an alkynoxy, a hydroxyalkyl, a hydroxyalkenyl, a hydroxyalkynyl, a haloalkyl, a haloalkenyl, a haloalkynyl, an optionally substituted phenyl, an optionally substituted bicyclic aryl, an optionally substituted five to six-membered monocyclic heteroaryl, an optionally substituted nine to fourteen-membered bicyclic heteroaryl, an optionally substituted cycloalkyl or an optionally substituted heterocyclic group and —COR$_9$, or R$_{10}$ and R$_{11}$, taken together with the nitrogen atom to which they are attached, form a five to six-membered heteroaryl group;

R$_{12}$, R$_{13}$ and R$_{14}$ are each independently —H, an optionally substituted alkyl, an optionally substituted phenyl or an optionally substituted benzyl, or R$_{12}$ and R$_{13}$, taken together with the nitrogen atom to which they are attached, form an optionally substituted heterocyclic group or an optionally substituted heteroaryl group;

R$_{15}$ is an optionally substituted alkyl, an optionally substituted aryl or an optionally substituted heteroaryl; and p is 1 or 2;

provided that when R$_3$ and R$_4$ are both methyl, then R$_1$ and R$_2$ are not both unsubstituted phenyl.

2. The compound of claim 1, wherein the compound is represented by the following structural formula:

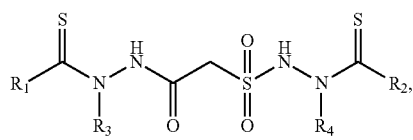

or a pharmaceutically acceptable salt or a transition metal chelate, coordinate or complex of the compound or a transition metal chelate, coordinate or complex of a deprotonated form of the compound.

3. The compound of claim 1, wherein the compound is represented by the following structural formula:

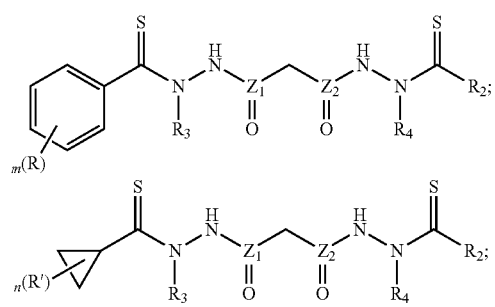

or a pharmaceutically acceptable salt or a transition metal chelate, coordinate or complex of the compound or a transition metal chelate, coordinate or complex of a deprotonated form of the compound, wherein:

Z$_1$ is C and Z$_2$ is S=O;

R for each occurrence is independently selected from the group consisting of —H, —OH, —Br, —Cl, —I, —F, —R$^a$, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NH-CONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHN(R$^a$R$^b$), —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, heterocyclic group, benzyl group and aryl group;

R' is —H, —OH, —Br, —Cl, —I, —F, —R$^a$, —OR$^a$ or —O—COR$^a$;

R$^a$-R$^d$ are each independently a lower alkyl, a lower haloalkyl, a lower alkoxy, a lower hydroxyalkyl, benzyl, aryl, or, —NR$^a$R$^d$, taken together, can also form an optionally substituted heterocyclic group;

R$_2$ is selected from the group consisting of pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl, wherein each of the pyrrolidinyl, pyrazinyl, pyridinyl, dioxolopyridinyl, benzothiophenyl, benzodioxolyl, thiophenyl, furanyl, morpholinyl, piperidinyl, cyclopropyl, cyclobutyl, cyclopentyl, cyclohexyl and (methyl)cyclopropyl represented by $R_2$ is optionally substituted;

$R_3$ and $R_4$ are each independently —H, an optionally substituted lower alkyl, an optionally substituted alkenyl, an optionally substituted alkynyl, an optionally substituted cycloalkyl, an optionally substituted phenyl or an optionally substituted benzyl m is 1, 2, 3, 4, or 5; and n is 1, 2, 3, 4 or 5.

4. The compound of claim 1, wherein the compound is represented by the following structural formula:

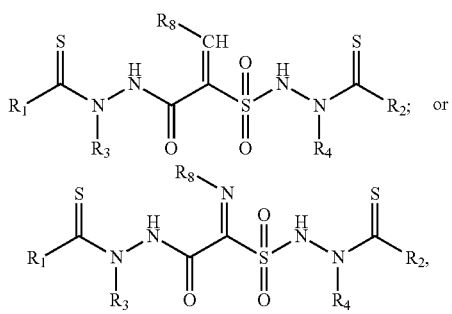

or a pharmaceutically acceptable salt or a transition metal chelate, coordinate or complex of the compound or a transition metal chelate, coordinate or complex of a deprotonated form of the compound.

5. The compound of claim 1, wherein one of $R_1$ and $R_2$ is —$NR_{12}R_{13}$, —$OR_{14}$, —$SR_{14}$ and —$S(O)_pR_{15}$; and the other one of $R_1$ and $R_2$ is selected from the group consisting of an optionally substituted alkyl, an optionally substituted alkenyl, an optionally substituted alkynyl; an optionally substituted cycloalkyl, an optionally substituted cycloalkenyl, an optionally substituted heterocyclic group wherein the heterocyclic group is bonded to the thiocarbonyl carbon via a carbon-carbon linkage, an optionally substituted phenyl, an optionally substituted bicyclic aryl, an optionally substituted five to seven-membered monocyclic heteroaryl, an optionally substituted nine to fourteen-membered bicyclic heteroaryl wherein the heteroaryl group is bonded to the thiocarbonyl carbon via a carbon-carbon linkage, —$NR_{12}R_{13}$, —$OR_{14}$, —$SR_{14}$ and —$S(O)_pR_{15}$.

6. The compound of claim 5, wherein the compound is represented by the following structural formula:

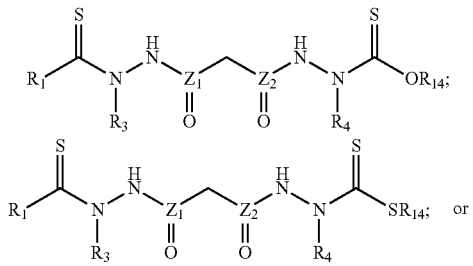

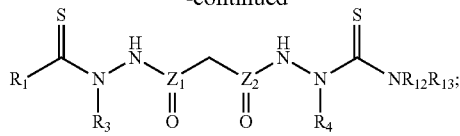

or a pharmaceutically acceptable salt or a transition metal chelate, coordinate or complex of the compound or a transition metal chelate, coordinate or complex of a deprotonated form of the compound, wherein:

$Z_1$ is C and $Z_2$ is S=O;

$R_1$ is selected from the group consisting of an optionally substituted alkyl, an optionally substituted alkenyl, an optionally substituted alkynyl; an optionally substituted cycloalkyl, an optionally substituted cycloalkenyl, an optionally substituted heterocyclic group wherein the heterocyclic group is bonded to the thiocarbonyl carbon via a carbon-carbon linkage, an optionally substituted phenyl, an optionally substituted bicyclic aryl, an optionally substituted five to seven-membered monocyclic heteroaryl, an optionally substituted nine to fourteen-membered bicyclic heteroaryl wherein the heteroaryl group is bonded to the thiocarbonyl carbon via a carbon-carbon linkage, —$NR_{12}R_{13}$, —$OR_{14}$, —$SR_{14}$ and —$S(O)_pR_{15}$; and $R_{12}$, $R_{13}$ and $R_{14}$ are each independently —H, an optionally substituted lower alkyl, an optionally substituted phenyl or an optionally substituted benzyl, or $R_{12}$ and $R_{13}$, taken together with the nitrogen atom to which they are attached, form an optionally substituted five to six-membered heterocyclic group or an optionally substituted five to six-membered heteroaryl group, wherein the alkyl represented by $R_{12}$, $R_{13}$ and $R_{14}$ is optionally substituted with —OH, —Br, —Cl, —I, —F, —$R^a$, —$OR^a$ or —$COOR^a$, and the phenyl and benzyl represented by $R_{12}$, $R_{13}$ and $R_{14}$ and the heterocyclic and heteroaryl group represented by —$NR_{12}R_{13}$ are optionally substituted with —OH, —Br, —Cl, —I, —F, —$R^a$, —$OR^a$, —$COOR^a$, —CN, —$NO_2$, morpholinyl, piperidinyl, and pyrrolidinyl, wherein $R^a$ is a lower alkyl or a lower haloalkyl.

7. The compound of claim 6, wherein the compound is represented by the following structural formula:

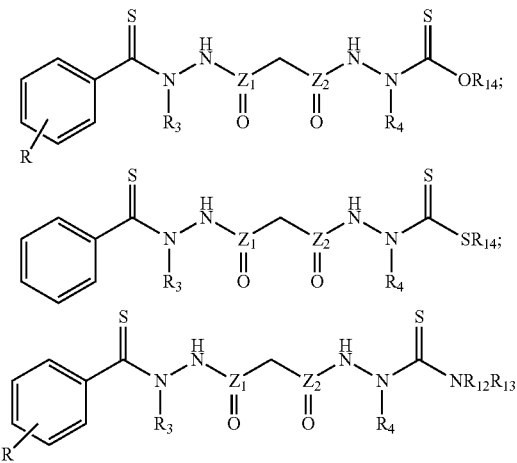

-continued

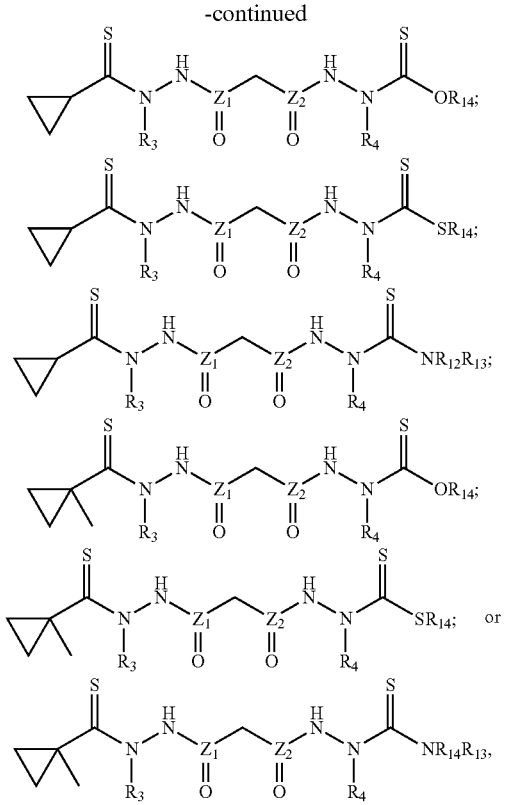

or a pharmaceutically acceptable salt or a transition metal chelate, coordinate or complex of the compound or a transition metal chelate, coordinate or complex of a deprotonated form of the compound, wherein R for each occurrence is independently selected from the group consisting of —H, —OH, —Br, —Cl, —I, —F, —$R^a$, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—$N(R^aR^b)$, —$NR^d$—C(=NH)—$NH_2$, —$NR^d$—C(=NH)—$NHR^a$, —$NR^d$—C(=NH)—$N(R^aR^b)$, —$NR^d$—C(=$NR^c$)—$NH_2$, —$NR^d$—C(=$NR^c$)—$NHR^a$, —$NR^d$—C(=$NR^c$)—$N(R^aR^b)$, —$NHNH_2$, —$NHNHR^a$, —$NHN(R^aR^b)$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —$S(O)R^a$, —$S(O)_2R^a$, heterocyclic group, benzyl group and aryl group;

$R_1$ is selected from the group consisting of phenyl, pyrrolidinyl, pyrazinyl, pyridinyl, dioxolopyridinyl, benzothiophenyl, benzodioxolyl, thiophenyl, furanyl, morpholinyl, piperidinyl, oxazole, isoxazole, thiazole, isothiazole, imidazole, cyclopropyl, cyclobutyl, cyclopentyl, cyclohexyl, and (methyl)cyclopropyl, wherein each of the phenyl, pyrrolidinyl, pyrazinyl, pyridinyl, dioxolopyridinyl, benzothiophenyl, benzodioxolyl, thiophenyl, furanyl, morpholinyl, piperidinyl, cyclopropyl, cyclobutyl, cyclopentyl, cyclohexyl and (methyl)cyclopropyl represented by $R_1$ is optionally substituted;

$R_3$ and $R_4$ are each independently —H, an optionally substituted lower alkyl, an optionally substituted alkenyl, an optionally substituted alkynyl, an optionally substituted cycloalkyl, an optionally substituted phenyl or an optionally substituted benzyl; and $R^b$-$R^d$ are each independently a lower alkyl, a lower haloalkyl, a lower alkoxy, a lower hydroxyalkyl, benzyl, aryl, or, —$NR^aR^d$, taken together, can also form an optionally substituted heterocyclic group.

8. The compound of claim 4, wherein the compound is represented by the following structural formula:

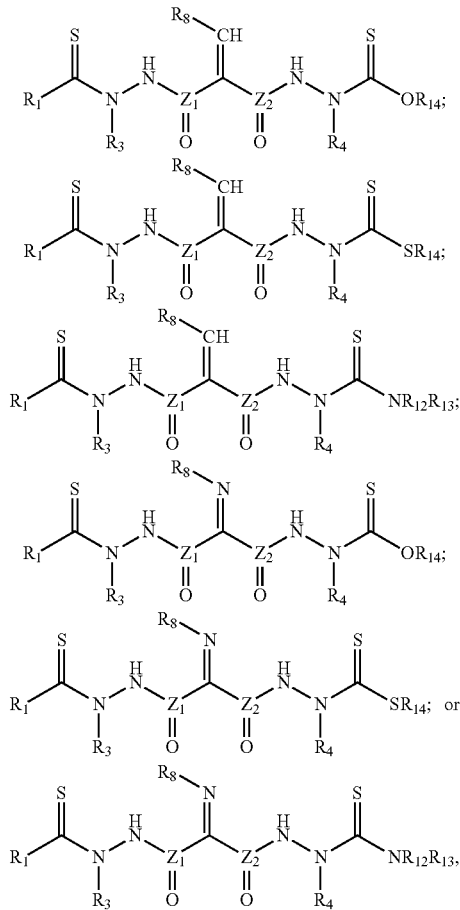

or a pharmaceutically acceptable salt or a transition metal chelate, coordinate or complex of the compound or a transition metal chelate, coordinate or complex of a deprotonated form of the compound, wherein:

$Z_1$ is C and $Z_2$ is S=O; and $R_1$ is selected from the group consisting of an optionally substituted alkyl, an optionally substituted alkenyl, an optionally substituted alkynyl; an optionally substituted cycloalkyl, an optionally substituted cycloalkenyl, an optionally substituted heterocyclic group wherein the heterocyclic group is bonded to the thiocarbonyl carbon via a carbon-carbon linkage, an optionally substituted phenyl, an optionally substituted bicyclic aryl, an optionally substituted five to seven-membered monocyclic heteroaryl, an optionally substituted nine to fourteen-membered bicyclic heteroaryl wherein the heteroaryl group is bonded to the thiocarbonyl carbon via a carbon-carbon linkage, —NR$_{12}$R$_{13}$, —OR$_{14}$, —SR$_{14}$ and —S(O)$_p$R$_{15}$.

9. The compound of claim 1, wherein the compound is represented by the following structural formula:

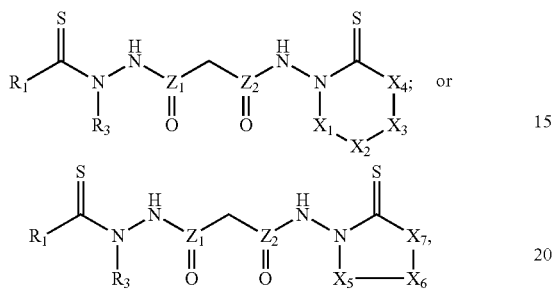

or a pharmaceutically acceptable salt or a transition metal chelate, coordinate or complex of the compound or a transition metal chelate, coordinate or complex of a deprotonated form of the compound, wherein:

Z$_1$ is C and Z$_2$ is S=O;

X$_1$, X$_2$, X$_3$ and X$_4$ are each independently selected from the group consisting of =CR$_{16}$—, —CR$_{17}$R$_{18}$—, =N—, —NR$_{19}$—, —O— and —S—; or X$_3$ and X$_4$, or X$_2$ and X$_3$, or X$_1$ and X$_2$, taken together form a fused aromatic ring optionally containing one or two heteroatoms and the fused aromatic ring is optionally substituted;

X$_5$, X$_6$ and X$_7$ are each independently selected from the group consisting of =CR$_{16}$—, —CR$_{17}$R$_{18}$—, =N—, —NR$_{19}$—, —O— and —S—; or X$_6$ and X$_7$, or X$_5$ and X$_6$, taken together to form a fused aromatic ring optionally containing one or two heteroatoms and the fused aromatic ring is optionally substituted;

R$_1$ is selected from the group consisting of an optionally substituted alkyl, an optionally substituted alkenyl, an optionally substituted alkynyl; an optionally substituted cycloalkyl, an optionally substituted cycloalkenyl, an optionally substituted heterocyclic group wherein the heterocyclic group is bonded to the thiocarbonyl carbon via a carbon-carbon linkage, an optionally substituted phenyl, an optionally substituted bicyclic aryl, an optionally substituted five to seven-membered monocyclic heteroaryl, an optionally substituted nine to fourteen-membered bicyclic heteroaryl wherein the heteroaryl group is bonded to the thiocarbonyl carbon via a carbon-carbon linkage, —NR$_{12}$R$_{13}$, —OR$_{14}$, —SR$_{14}$ and —S(O)$_p$R$_{15}$, or R$_1$ and R$_3$, taken together with the atoms to which they are attached, form an optionally substituted heterocyclic group or an optionally substituted heteroaryl group;

R$_{12}$, R$_{13}$ and R$_{14}$ are each independently —H, (C$_1$-C$_4$)alkyl, (C$_1$-C$_4$)haloalkyl, or phenyl optionally substituted with —OH, —Br, —Cl, —I, —F, —R$^a$, —OR$^a$, —COOR$^a$, —CN, —NO$_2$, morpholinyl, piperidinyl or pyrrolidinyl; or R$_{12}$ and R$_{13}$ taken together with the nitrogen to which they are attached form a heterocyclic group or a heteroaryl group selected from the group consisting of pyrrolidinyl, piperidinyl, morpholinyl, pyridinyl, pyrazinyl and imidazolyl, each of which is optionally substituted with —OH, —Br, —Cl, —I, —F, —R$^a$, —OR$^a$, —C(O)OR$^a$, —CN and —NO$_2$, wherein R$^a$ is a lower alkyl or a lower haloalkyl; and R$_{16}$, R$_{17}$, R$_{18}$ and R$_{19}$ are each independently selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclic group, an optionally substituted aryl, an optionally substituted heteroaryl, —OH, —Br, —Cl, —I, —F, —OR$^a$, —O—COR$^a$, —COR$^a$, —CN, —NO$_2$, —COOH, —SO$_3$H, —NH$_2$, —NHR$^a$, —N(R$^a$R$^b$), —COOR$^a$, —CHO, —CONH$_2$, —CONHR$^a$, —CON(R$^a$R$^b$), —NHCOR$^a$, —NRCOR$^a$, —NHCONH$_2$, —NHCONR$^a$H, —NHCON(R$^a$R$^b$), —NR$^c$CONH$_2$, —NR$^c$CONR$^a$H, —NR$^c$CON(R$^a$R$^b$), —C(=NH)—NH$_2$, —C(=NH)—NHR$^a$, —C(=NH)—N(R$^a$R$^b$), —C(=NR$^c$)—NH$_2$, —C(=NR$^c$)—NHR$^a$, —C(=NR$^c$)—N(R$^a$R$^b$), —NH—C(=NH)—NH$_2$, —NH—C(=NH)—NHR$^a$, —NH—C(=NH)—N(R$^a$R$^b$), —NH—C(=NR$^c$)—NH$_2$, —NH—C(=NR$^c$)—NHR$^a$, —NH—C(=NR$^c$)—N(R$^a$R$^b$), —NR$^d$—C(=NH)—NH$_2$, —NR$^d$—C(=NH)—NHR$^a$, —NR$^d$—C(=NH)—N(R$^a$R$^b$), —NR$^d$—C(=NR$^c$)—NH$_2$, —NR$^d$—C(=NR$^c$)—NHR$^a$, —NR$^d$—C(=NR$^c$)—N(R$^a$R$^b$), —NHNH$_2$, —NHNHR$^a$, —NHN(R$^a$R$^b$), —SO$_2$NH$_2$, —SO$_2$NHR$^a$, —SO$_2$NR$^a$R$^b$, —CH=CHR$^a$, —CH=CR$^a$R$^b$, —CR$^c$=CR$^a$R$^b$, —CR$^c$=CHR$^a$, —CR$^c$=CR$^a$R$^b$, —CCR$^a$, —SH, —SR$^a$, —S(O)R$^a$, —S(O)$_2$R$^a$, wherein R$^a$-R$^d$ are each independently a lower alkyl, a lower haloalkyl, benzyl, aryl, or, —NR$^a$R$^d$, taken together, can also form an optionally substituted heterocyclic group.

10. The compound of claim 9, wherein the compound is selected from the group consisting of:

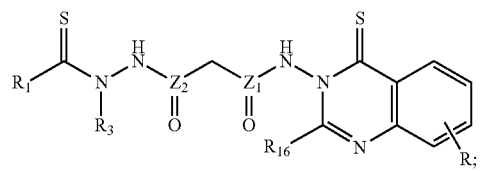

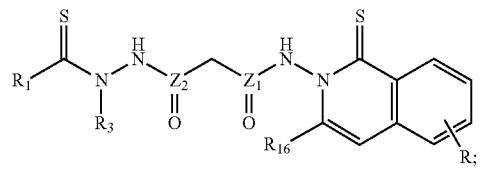

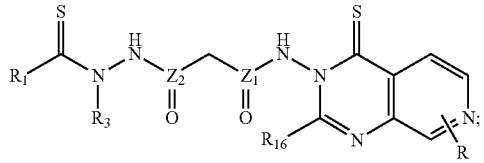

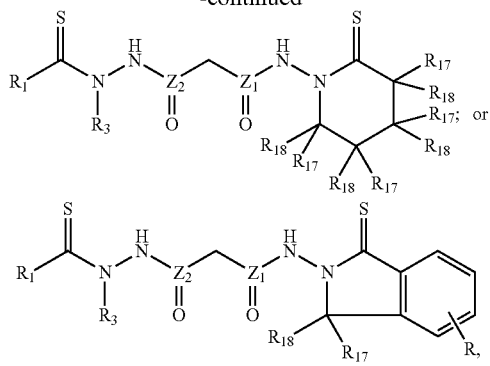

or a pharmaceutically acceptable salt or a transition metal chelate, coordinate or complex of the compound or a transition metal chelate, coordinate or complex of a deprotonated form of the compound, wherein:

R for each occurrence is independently selected from the group consisting of —H, —OH, —Br, —Cl, —I, —F, —$R^a$, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —NH-$CONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —$C(=NR^c)$—$NH_2$, —$C(=NR^c)$—$NHR^a$, —$C(=NR^c)$—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—$N(R^aR^b)$, —$NR^d$—C(=NH)—$NH_2$, —$NR^d$—C(=NH)—$NHR^a$, —$NR^d$—C(=NH)—$N(R^aR^b)$, —$NR^d$—C(=$NR^c$)—$NH_2$, —$NR^d$—C(=$NR^c$)—$NHR^a$, —$NR^d$—C(=$NR^c$)—$N(R^aR^b)$, —$NHNH_2$, —$NHNHR^a$, —$NHN(R^aR^b)$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —S(O)$R^a$, —S(O)$_2R^a$, heterocyclic group, benzyl group and aryl group.

11. The compound of claim 10, wherein the compound is represented by the following structural formula:

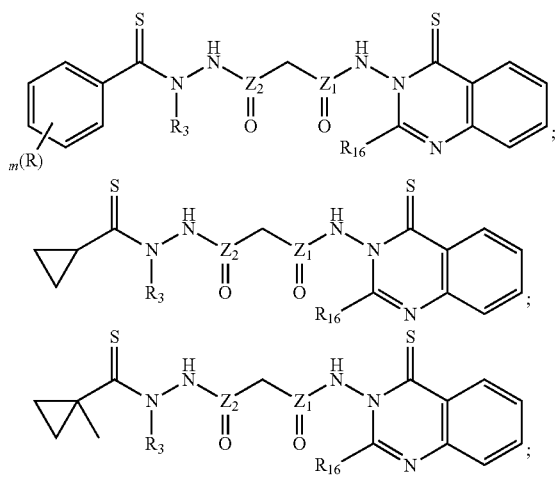

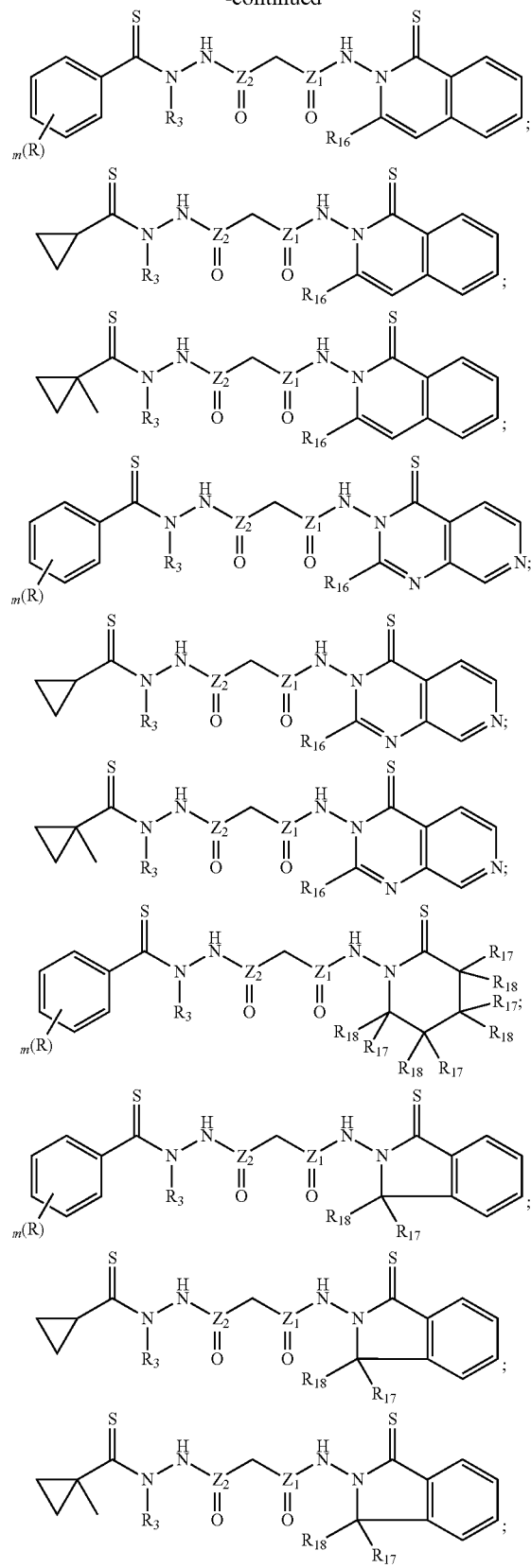

or a pharmaceutically acceptable salt or a transition metal chelate, coordinate or complex of the compound or a transition metal chelate, coordinate or complex of a deprotonated form of the compound, wherein:

R for each occurrence is independently selected from the group consisting of —H, —OH, —Br, —Cl, —I, —F, —$R^a$, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —NHCONH$_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —$C(=NR^c)$—$NH_2$, —$C(=NR^c)$—$NHR^a$, —$C(=NR^c)$—$N(R^aR^b)$, —NH—C(=NH)—$NH_2$, —NH—C(=NH)—$NHR^a$, —NH—C(=NH)—$N(R^aR^b)$, —NH—$C(=NR^c)$—$NH_2$, —NH—$C(=NR^c)$—$NHR^a$, —NH—$C(=NR^c)$—$N(R^aR^b)$, —$NR^d$—C(=NH)—$NH_2$, —$NR^d$—C(=NH)—$NHR^a$, —$NR^d$—C(=NH)—$N(R^aR^b)$, —$NR^d$—$C(=NR^c)$—$NH_2$, —$NR^d$—$C(=NR^c)$—$NHR^a$, —$NR^d$—$C(=NR^c)$—$N(R^aR^b)$, —$NHNH_2$, —$NHNHR^a$, —$NHN(R^aR^b)$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —$S(O)R^a$, —$S(O)_2R^a$, heterocyclic group, benzyl group and aryl group;

$R^a$-$R^d$ are each independently a lower alkyl, a lower haloalkyl, a lower alkoxy, a lower hydroxyalkyl, benzyl, aryl, or, —$NR^aR^d$, taken together, can also form an optionally substituted heterocyclic group; and m is 1, 2, 3, 4, or 5.

12. The compound of claim 4, wherein the compound is represented by the following structural formula:

[chemical structure]

[chemical structure]

[chemical structure]

[chemical structure]

or a pharmaceutically acceptable salt or a transition metal chelate, coordinate or complex of the compound or a transition metal chelate, coordinate or complex of a deprotonated form of the compound, wherein:

$Z_1$ is C and $Z_2$ is S=O;

$X_1$, $X_2$, $X_3$ and $X_4$ are each independently selected from the group consisting of =$CR_{16}$—, —$CR_{17}R_{18}$—, =N— and —$NR_{19}$—; or $X_3$ and $X_4$, or $X_2$ and $X_3$, or $X_1$ and $X_2$, taken together form a fused aromatic ring optionally containing one or two heteroatoms and the fused aromatic ring is optionally substituted;

$X_5$, $X_6$ and $X_7$ are each independently selected from the group consisting of =$CR_{16}$—, —$CR_{17}R_{18}$—, =N— and —$NR_{19}$—; or $X_6$ and $X_7$, or $X_5$ and $X_6$, taken together to form a fused aromatic ring optionally containing one or two heteroatoms and the fused aromatic ring is optionally substituted;

$R_1$ is selected from the group consisting of an optionally substituted alkyl, an optionally substituted alkenyl, an optionally substituted alkynyl; an optionally substituted cycloalkyl, an optionally substituted cycloalkenyl, an optionally substituted heterocyclic group wherein the heterocyclic group is bonded to the thiocarbonyl carbon via a carbon-carbon linkage, an optionally substituted phenyl, an optionally substituted bicyclic aryl, an optionally substituted five to seven-membered monocyclic heteroaryl, an optionally substituted nine to fourteen-membered bicyclic heteroaryl wherein the heteroaryl group is bonded to the thiocarbonyl carbon via a carbon-carbon linkage, —$NR_{12}R_{13}$, —$OR_{14}$, —$SR_{14}$ and —$S(O)_pR_{15}$, or $R_1$ and $R_3$, taken together with the atoms to which they are attached, form an optionally substituted heterocyclic group or an optionally substituted heteroaryl group; and $R_{16}$, $R_{17}$, $R_{18}$ and $R_{19}$ are each independently selected from the group consisting of —H, an optionally substituted alkyl, an optionally substituted alkenyl, an optionally substituted alkynyl, an optionally substituted cycloalkyl, an optionally substituted cycloalkenyl, an optionally substituted heterocyclic group, an optionally substituted aryl, an optionally substituted heteroaryl, —OH, —Br, —Cl, —I, —F, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —$NHCONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —$C(=NR^c)$—$NH_2$, —$C(=NR^c)$—$NHR^a$, —$C(=NR^c)$—$N(R^aR^b)$, —NH—C(=NH)—$NH_2$, —NH—C(=NH)—$NHR^a$, —NH—C(=NH)—$N(R^aR^b)$, —NH—$C(=NR^c)$—$NH_2$, —NH—$C(=NR^c)$—$NHR^a$, —NH—$C(=NR^c)$—$N(R^aR^b)$, —$NR^d$—C(=NH)—$NH_2$, —$NR^d$—C(=NH)—$NHR^a$, —$NR^d$—C(=NH)—$N(R^aR^b)$, —$NR^d$—$C(=NR^c)$—$NH_2$, —$NR^d$—$C(=NR^c)$—$NHR^a$, —$NR^d$—$C(=NR^c)$—$N(R^aR^b)$, —$NHNH_2$, —$NHNHR^a$, —$NHN(R^aR^b)$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —$S(O)R^a$, —$S(O)_2R^a$, wherein $R^a$-$R^d$ are each independently a lower alkyl, a lower haloalkyl, benzyl, aryl, or, —$NR^aR^d$, taken together, can also form an optionally substituted heterocyclic group.

13. The compound of claim 12, wherein the compound is represented by the following structural formula:

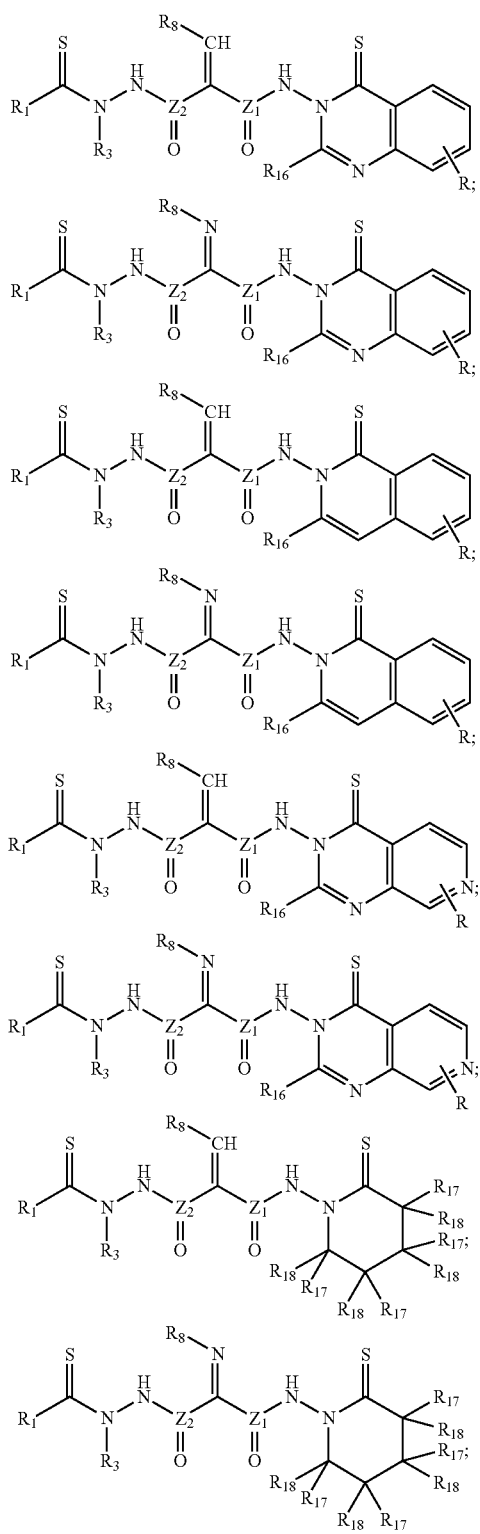

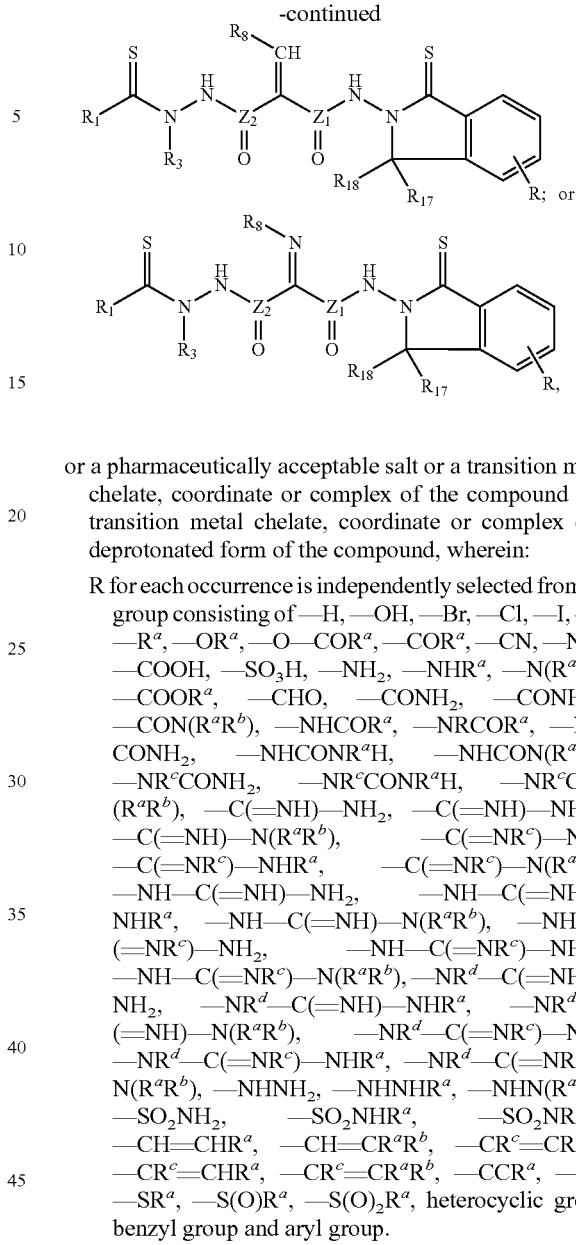

or a pharmaceutically acceptable salt or a transition metal chelate, coordinate or complex of the compound or a transition metal chelate, coordinate or complex of a deprotonated form of the compound, wherein:

R for each occurrence is independently selected from the group consisting of —H, —OH, —Br, —Cl, —I, —F, —$R^a$, —$OR^a$, —O—$COR^a$, —$COR^a$, —CN, —$NO_2$, —COOH, —$SO_3H$, —$NH_2$, —$NHR^a$, —$N(R^aR^b)$, —$COOR^a$, —CHO, —$CONH_2$, —$CONHR^a$, —$CON(R^aR^b)$, —$NHCOR^a$, —$NRCOR^a$, —NH-$CONH_2$, —$NHCONR^aH$, —$NHCON(R^aR^b)$, —$NR^cCONH_2$, —$NR^cCONR^aH$, —$NR^cCON(R^aR^b)$, —C(=NH)—$NH_2$, —C(=NH)—$NHR^a$, —C(=NH)—$N(R^aR^b)$, —C(=$NR^c$)—$NH_2$, —C(=$NR^c$)—$NHR^a$, —C(=$NR^c$)—$N(R^aR^b)$, —NH—C(=NH)—$NH_2$, —NH—C(=NH)—$NHR^a$, —NH—C(=NH)—$N(R^aR^b)$, —NH—C(=$NR^c$)—$NH_2$, —NH—C(=$NR^c$)—$NHR^a$, —NH—C(=$NR^c$)—$N(R^aR^b)$, —$NR^d$—C(=NH)—$NH_2$, —$NR^d$—C(=NH)—$NHR^a$, —$NR^d$—C(=NH)—$N(R^aR^b)$, —$NR^d$—C(=$NR^c$)—$NH_2$, —$NR^d$—C(=$NR^c$)—$NHR^a$, —$NR^d$—C(=$NR^c$)—$N(R^aR^b)$, —$NHNH_2$, —$NHNHR^a$, —$NHN(R^aR^b)$, —$SO_2NH_2$, —$SO_2NHR^a$, —$SO_2NR^aR^b$, —CH=$CHR^a$, —CH=$CR^aR^b$, —$CR^c$=$CR^aR^b$, —$CR^c$=$CHR^a$, —$CR^c$=$CR^aR^b$, —$CCR^a$, —SH, —$SR^a$, —$S(O)R^a$, —$S(O)_2R^a$, heterocyclic group, benzyl group and aryl group.

14. A pharmaceutical composition comprising a compound of claim 1 and a pharmaceutically acceptable carrier or diluent.

15. A method of treating a subject with cancer comprising administering to the subject an effective amount of a compound of claim 1, wherein the cancer is responsive to Hsp70 induction.

* * * * *